US009745380B2

(12) United States Patent
Govindan et al.

(10) Patent No.: US 9,745,380 B2
(45) Date of Patent: **\*Aug. 29, 2017**

(54) RS7 ANTIBODIES

(75) Inventors: Serengulam Govindan, Summit, NJ (US); Zhengxing Qu, Warren, NJ (US); Hans Hansen, Picayune, MS (US); David M. Goldenberg, Mendham, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 1284 days.

This patent is subject to a terminal disclaimer.

(21) Appl. No.: 11/868,290

(22) Filed: Oct. 5, 2007

(65) Prior Publication Data

US 2008/0131363 A1    Jun. 5, 2008

Related U.S. Application Data

(62) Division of application No. 11/745,896, filed on May 8, 2007, now Pat. No. 7,517,964, which is a division of application No. 10/377,121, filed on Mar. 3, 2003, now Pat. No. 7,238,785.

(60) Provisional application No. 60/360,229, filed on Mar. 1, 2002.

(51) Int. Cl.

| A61K 39/395 | (2006.01) |
|---|---|
| C07K 16/30 | (2006.01) |
| A61K 38/16 | (2006.01) |
| A61K 38/18 | (2006.01) |
| A61K 38/19 | (2006.01) |
| A61K 38/21 | (2006.01) |
| A61K 45/06 | (2006.01) |
| A61K 47/48 | (2006.01) |
| A61K 51/10 | (2006.01) |
| C07K 16/28 | (2006.01) |
| A61K 39/00 | (2006.01) |

(52) U.S. Cl.
CPC ............ C07K 16/30 (2013.01); A61K 38/164 (2013.01); A61K 38/168 (2013.01); A61K 38/1816 (2013.01); A61K 38/19 (2013.01); A61K 38/21 (2013.01); A61K 45/06 (2013.01); A61K 47/48592 (2013.01); A61K 51/1054 (2013.01); C07K 16/28 (2013.01); A61K 2039/505 (2013.01); C07K 2317/24 (2013.01); C07K 2317/56 (2013.01); C07K 2317/94 (2013.01)

(58) Field of Classification Search
CPC .................. C07K 16/30; A61K 39/395; A61K 39/39558; A61K 2039/505
See application file for complete search history.

(56) References Cited

U.S. PATENT DOCUMENTS

| 5,185,254 | A | | 2/1993 | Linnenbach |
|---|---|---|---|---|
| 5,530,101 | A | * | 6/1996 | Queen .................... C07K 16/00 424/133.1 |
| 5,840,854 | A | * | 11/1998 | Hellstrom et al. ......... 530/387.7 |
| 6,180,377 | B1 | | 1/2001 | Morgan et al. |
| 6,558,669 | B1 | | 5/2003 | Govindan et al. |
| 6,653,104 | B2 | | 11/2003 | Goldenberg |
| 6,824,780 | B1 | * | 11/2004 | Devaux et al. |
| 7,288,249 | B2 | * | 10/2007 | Carter .............. A61K 39/39541 424/130.1 |
| 7,420,040 | B2 | | 9/2008 | Young et al. |
| 7,420,041 | B2 | | 9/2008 | Young et al. |
| 8,309,094 | B2 | | 11/2012 | Gerber et al. |
| 8,574,575 | B2 | * | 11/2013 | Govindan et al. ......... 424/133.1 |
| 8,586,049 | B2 | | 11/2013 | Gerber et al. |
| 8,715,662 | B2 | | 5/2014 | Alberti |
| 8,871,908 | B2 | | 10/2014 | Liu et al. |
| 2002/0006379 | A1 | | 1/2002 | Hansen et al. |
| 2007/0202043 | A1 | | 8/2007 | Young et al. |
| 2007/0202113 | A1 | | 8/2007 | Young et al. |
| 2008/0213267 | A1 | | 9/2008 | Young et al. |

(Continued)

FOREIGN PATENT DOCUMENTS

| DE | 100 34 607 | 2/2002 |
|---|---|---|
| WO | 9714796 | 4/1997 |

(Continued)

OTHER PUBLICATIONS

Bendig M. M. Methods: A Companion to Methods in Enzymology, 8:83-93, 1995.*

(Continued)

*Primary Examiner* — Laura B Goddard
*Assistant Examiner* — Meera Natarajan
(74) *Attorney, Agent, or Firm* — Richard A. Nakashima

(57) ABSTRACT

This invention relates to monovalent and multivalent, monospecific binding proteins and to multivalent, multispecific binding proteins. One embodiment of these binding proteins has one or more binding sites where each binding site binds with a target antigen or an epitope on a target antigen. Another embodiment of these binding proteins has two or more binding sites where each binding site has affinity towards different epitopes on a target antigen or has affinity towards either a target antigen or a hapten. The present invention further relates to recombinant vectors useful for the expression of these functional binding proteins in a host. More specifically, the present invention relates to the tumor-associated antigen binding protein designated RS7, and other EGP-1 binding-proteins. The invention further relates to humanized, human and chimeric RS7 antigen binding proteins, and the use of such binding proteins in diagnosis and therapy.

5 Claims, 15 Drawing Sheets

(56) References Cited

U.S. PATENT DOCUMENTS

| | | |
|---|---|---|
| 2008/0305104 A1 | 12/2008 | Young et al. |
| 2009/0142263 A1 | 6/2009 | Young et al. |
| 2009/0191118 A1 | 7/2009 | Young et al. |
| 2012/0052076 A1 | 3/2012 | Alberti |
| 2012/0237518 A1 | 9/2012 | Yamaguchi et al. |
| 2013/0089872 A1 | 4/2013 | Nakamura et al. |
| 2013/0122020 A1 | 5/2013 | Liu et al. |
| 2013/0344509 A1 | 12/2013 | Nakamura et al. |
| 2014/0120035 A1* | 5/2014 | Govindan et al. ........... 424/1.49 |
| 2014/0357844 A1 | 12/2014 | Liu et al. |
| 2016/0257746 A1 | 9/2016 | Liu et al. |
| 2016/0333110 A1 | 11/2016 | Nakamura et al. |

FOREIGN PATENT DOCUMENTS

| | | |
|---|---|---|
| WO | 98/12227 | 3/1998 |
| WO | 98/42378 | 10/1998 |
| WO | WO00/02587 A1 * | 1/2000 |
| WO | 00/69914 | 11/2000 |
| WO | 2010089782 | 8/2010 |

OTHER PUBLICATIONS

Ripani et al. International Journal of Cancer, 76(5):671-676, May 29, 1998.*

El Sewedy et al. International Journal of Cancer, 75(2):324-330, 1998.*

Nakashima et al., Int. J. Cancer 2004; 112:1029-35.*

Trerotola et al., Biochem Biophys Acta 2010; 1805:119-120.*

Phillip et al., J Clin Oncol. 2010; 28:3605-10, Abstract Only.*

XP-001154527—Zhengxing Qu et al., "Humanization of IMMU31, an alpha-fetoprotein-specific antibody," Clin. Cancer Res. vol. 5, No. 10, pp. 3094s-3100s (Oct. 1999).

XP-000999121—Lisa B. Shih et al., "In Vitro and In vivo Reactivity of an Internalizing Antibody, RS7, With Human Breast Cancer," Cancer Res (Supppl.) vol. 55, No. 10, pp. 5857s-5863s (Dec. 1995).

XP-002207879—Reinhilde Schoonjans et al., "FAB Chains as an Efficient Heterodimerization Scaffold for the Production of Recombinant Bispecific and Trispecific Antibody Derivatives," J. Immunol., vol. 165, No. 12, pp. 7050-7057 (Dec. 2000).

XP-000616008—S.O. Leung et al., "Chimerization of LL2, a Rapidly Internalizaing Antibody Specific for B Cell Lymphoma," Hybridoma vol. 13, No. 6, pp. 469-476 (Dec. 1994).

XP-001154183—Rhona Stein et al., "Therapy of a Breast Cancer Xenograft Using Humanized RS7 Labeled with Residualizing Iodine," Proceedings of the American Association for Cancer Research Annual Meeting, Mar. 2002, vol. 43, pp. 88-89 (Abstract).

Morrison et al., Proc. Natl. Acad. Sci., USA 81:6851-6855 (Nov. 1984).

Paul, William E., (ed.), Fundamental Immunology, 3rd Edition, p. 242 (1993).

Stein, R. et al., Cancer 73(3 Suppl):816-823 (Feb. 1, 1994).

Basu, A. et al., Int. J. Cnacer 62(4):472-479 (Aug. 9, 1995).

Stein, R. et al., Cancer Res. 55(14):3132-3139 (Jul. 15, 1995).

Shih, L.B. et al., J. Nucl. Med. 35(5):899-908 (May 1994).

Stein, R. et al., Int. J. Cancer 55(6):938-946 (Dec. 2, 1993).

Stein, R. et al., Int. J. Cancer Suppl. 8:98-102 (1994).

Stein, R. et al., Cancer Res. 50(4):1330-1336 (Feb. 15, 1990).

Rudikoff et al., Proc. Natl. Acad. Sci. USA 79(6):1979-1983 (1982).

Stein et al., "Radioimmunotherapy of a human lung cancer xenograft with monoclonal antibody RS7: evaluation of (177)Lu and comparison of its efficacy with that of (90)Y and residualizing (131)I", J Nucl Med. Jun. 2001;42(6):967-74.

Stein et al., "Improved iodine radiolabels for monoclonal antibody therapy", Cancer Res. Jan. 1, 2003;63(1):111-8.

Stein et al., "Successful therapy of a human lung cancer xenograft using MAb RS7 labeled with residualizing radioiodine", Crit Rev Oncol Hematol. Jul.-Aug. 2001;39(1-2):173-80.

Stein et al., "Targeting human cancer xenografts with monoclonal antibodies labeled using radioiodinated, diethylenetriaminepentaacetic acid-appended peptides", Clin Cancer Res. Oct. 1999;5(10 Suppl):3079s-3087s.

Stein et al., "Advantage of yttrium-90-labeled over iodine-131-labeled monoclonal antibodies in the treatment of a human lung carcinoma xenograft", Cancer. Dec. 15, 1997;80(12 Suppl):2636-41.

Cardillo et al., "Sacituzumab Govitecan (IMMU-132), an Anti-Trop-2/SN-38 Antibody-Drug Conjugate: Characterization and Efficacy in Pancreatic, Gastric, and Other Cancers", Bioconjug Chem. May 20, 2015;26(5):919-31, Epub May 8, 2015.

Goldenberg et al., "Trop-2 is a novel target for solid cancer therapy with sacituzumab govitecan (IMMU-132), an antibody-drug conjugate (ADC)", Oncotarget. Jun. 18, 2015. [Epub ahead of print].

Sharkey et al., "Enhanced Delivery of SN-38 to Human Tumor Xenografts with an Anti-Trop-2-SN-38 Antibody Conjugate (Sacituzumab Govitecan)", Clin Cancer Res. Jun. 23, 2015. pii: clincanres.0670.2015. [Epub ahead of print].

Starodub et al., "First-in-Human Trial of a Novel Anti-Trop-2 Antibody-SN-38 Conjugate, Sacituzumab Govitecan, for the Treatment of Diverse Metastatic Solid Tumors", Clin Cancer Res. May 5, 2015. [Epub ahead of print].

Baeuerle et al., "EpCAM (CD326) finding its role in cancer", Br J Cancer. Feb. 12, 2007;96(3):417-23.

Lipinski et al., "Human trophoblast cell-surface antigens defined by monoclonal antibodies", Proc Natl Acad Sci U S A. Aug. 1981;78(8):5147-50.

Bardia et al., "Safety and efficacy of anti-Trop-2 antibody drug conjugate, sacituzumab govitecan (IMMU-132), in heavily pre-treated patients with TNBC", Poster presented at San Antonio Breast Cancer Symposium, Dec. 10, 2015, San Antonio, TX.

Bardia et al., "Safety and tumor responses of the anti-Trop-2 antibody drug conjugate, sacituzumab govitecan (IMMU-132), in refractory, metastatic, triple-negative breast cancer (TNBC): An ongoing Phase II trial", Poster presented at AACR-NCI-EORTC International Conference: Molecular Targets and Cancer Therapeutics, Nov. 8, 2015, Boston, MA.

Basu et al., "The epithelial/carcinoma antigen EGP-1, recognized by monoclonal antibody RS7-3G11, is phosphorylated on serine 303", Int J Cancer. Aug. 9, 1995;62(4):472-9.

Basu et al., "Epithelial glycoprotein EGP-1 recognized by MAb RS7-3G11 is phosphorylated on serine 303", Proc. Amer. Assoc. Cancer Res. 36: 439 (Abstr. #2621), 1995.

Camidge et al., "Therapy of Advanced Metastatic Lung Cancers with an Anti-Trop-2-SN-38 Antibody-Drug Conjugate, IMMU-132: Interim Phase II Clinical Results", Oral presentation at 16th World Conference on Lung Cancer (WCLC), Sep. 7, 2015, Denver, CO.

Cardillo et al., "A novel immunotoxin comprising quadruple RNase tethered to an internalizing anti-TROP-2 humanized MAb shows potent cytotoxicity against diverse solid tumors in vitro", Proc. Amer. Assoc. Cancer Res. Annual Meeting, 51:1296 (Abstr. #5346), 2010.

Cardillo et al., "Combining an anti-Trop-2 antibody-SN-38 conjugate (sacituzumab govitecan) with microtubule inhibitors (paclitaxel and eribulin mesylate) or PARP inhibitor (olaparib) significantly improves therapeutic outcome in experimental triple-negative breast cancer (TNBC)", Mol Cancer Ther 2015;14(12 Suppl 2):Abstract nr C166.

Cardillo et al., "Synthetic lethality in TNBC mediated by an anti-Trop-2 antibody-drug conjugate, sacituzumab govitecan (IMMU-132), when combined with paclitaxel or the PARP inhibitor, olaparib", Poster presented at San Antonio Breast Cancer Symposium, Dec. 10, 2015, San Antonio, TX.

Chang et al., "In vitro and in vivo evaluation of a novel recombinant immunotoxin of ranpirnase fused to a humanized anti-EGP-1 antobody, HRS7, for the potential treatment of prostate and lung cancers", Proc. Amer. Assoc. Cancer Res. Annual Meeting, 48: (Abstr. #4795), 2007.

Goldenberg et al., Tolerability in mice, monkeys, and rabbits of new antibody (MAb)-drug (SN-38) immunoconjugates. Proc. Amer. Assoc. Cancer Res. 102nd Annual Meeting, 52: 865 (Abstr. #3619), 2011.

(56) References Cited

OTHER PUBLICATIONS

Goldenberg et al., "SN-38 antibody-drug conjugates as a novel platform for solid cancer therapy: preclinical science", American Association for Cancer Research (AACR) 2014 Annual Meeting, Abstr. #2904, Apr. 7, 2014.
Goldenberg et al., "Characterization of an anti-Trop-2-SN-38 antibody-drug conjugate (IMMU-132) with potent activity against solid cancers", American Society of Clinical Oncology (ASCO) 50th Annual Meeting. J Clin Oncol 32:5s, 2014 (suppl; abstr #3107), 2014.
Goldenberg et al., "IMMU-132, a potential new antibody-drug conjugate (ADC) for the treatment of triple-negative breast cancer (TNBC): Preclinical and initial clinical results", Poster P5-19-08 presented at San Antonio Breast Cancer Symposium, Dec. 9-13, 2014.
Govindan et al., "Optimal cleavable linker for antibody-SN-38 conjugates for cancer therapy: Impact of linker's stability on efficacy", Proc. Amer. Assoc. Cancer Res. 103rd Annual Meeting, 53: 611 (Abstr. #2526), 2012.
Govindan et al., "Preclinical therapy of breast cancer with a radioiodinated humanized anti-EGP-1 monoclonal antibody: advantage of a residualizing iodine radiolabel", Breast Cancer Res Treat Mar. 2004;84(2):173-82.
Govindan et al., "Conjugation of SN-38 to an anti-EGP-1 MAB, HRS7, via a cleavable linker shows selective therapeutic activity in a preclinical model of non-small cell lung cancer (NSCLC)", Proc. Eleventh Conf. on Cancer Therapy, Cancer Biotherapy & Radiopharmaceuticals, 21(4):401 (Abstr. #56), 2006.
Govindan et al., "Therapy of human colonic and lung cancer xenografts with SN-38 conjugates of anti-CEACAM5 and anti-EGP-1 humanized monoclonal antibodies", Proc. AACR Molecular Targets and Cancer Therapeutics, 347-348 (Abstr. #C287), 2007.
Govindan et al., "Efficacious therapies of two human pancreatic cancer xenografts and an aggressive human lymphoma xenograft with redesigned antibody-SN-38 conjugates", Proc. Amer. Assoc. Cancer Res. Annual Meeting, 51:591 (Abstr. #2438), 2010.
Liu et al., "Novel immunoRNases comprising multiple copies of ranpimase display potent cytotoxicity in human breast cancer cell lines expressing Trop-2", Proc. Amer. Assoc. Cancer Res. 103rd Annual Meeting, 53: 1124 (Abstr. #4636), 2012.
Ocean et al., "Interim results of IMMU-132 (sacituzumab govitecan), an anti-trop-2 antibody-drug conjugate (ADC) in patients with metastatic gastrointestinal (GI) cancers", Poster presented at ESMO's 17th World Congress on Gastrointestinal Cancer, Jul. 4, 2015.
Picozzi et al., "IMMU-132, a new antibody-drug conjugate (ADC), evaluated in patients with advanced, metastatic, pancreatic ductal adenocarcinoma (mPC): Results of a Phase I/II trial", Poster presented at American Association for Cancer Research (AACR) Special Conference on Pancreatic Cancer:Innovations in Research and Treatment, Abstr. #B99, May 18-21, 2014.
Shih et al., "Radioimmunodetection and radioimmunotherapy of xenografted human breast cancer with monoclonal antibody RS7", J. Immunother. 16: 169 (Abstr. #85), 1994.
Starodub et al., "Advanced solid cancer therapy with a novel antibody-drug conjugate (ADC), sacituzumab govitecan (IMMU-132): key preclinical and clinical results", Abstract CT236. Presented at American Association for Cancer Research (AACR) 2015 Annual Meeting, Philadelphia, PA, Apr. 20, 2015.
Starodub et al., "Safety, efficacy, and pharmacokinetics of a new humanized anti-Trop-2 antibody-SN-38 conjugate (IMMU-132) for the treatment of diverse epithelial cancers: Phase I clinical experience", AACR-NCI-EORTC International Conference on Molecular Targets and Cancer Therapeutics Meeting. (Abstr. #C67), Oct. 22, 2013.
Starodub et al., "SN-38 antibody-drug conjugate (ADC) targeting Trop-2, IMMU-132, as a novel platform for the therapy of diverse metastatic solid cancers: Initial clinical results", American Association for Cancer Research (AACR) 2014 Annual Meeting, Abstr. #CT206, Apr. 7, 2014.
Starodub et al., "Therapy of gastrointestinal malignancies with an anti-Trop-2-SN-38 antibody drug conjugate (ADC) (sacituzumab govitecan): Phase I/II clinical experience", 2015 American Society of Clinical Oncology (ASCO) Annual Meeting, J Clin Oncol 33, 2015 (suppl; abstr 3546), Board 38, Jun. 1, 2015.
Stein et al., "Therapy of a breast cancer xenograft using humanized RS7 labeled with residualizing iodine", Proc. Amer. Assoc. Cancer Res. 43: 88 (Abstr. #443), 2002.
Stein et al., "Radioimmunotherapy of lung cancer with MAb RS7-3G11", Proc. Amer. Assoc. Cancer Res. 33: 318 (Abstr. #1897), 1992.
Stein et al., "Radioimmunotherapy with MAb RS7-3G11 in an animal model", Antib. Immunoconj. Radiopharm. 5: 358 (Abstr. #100), 1992.
Stein et al., "Specificity and properties of MAb RS7-3G11 and the antigen defined by this pancarcinoma monoclonal antibody", Int J Cancer. Dec. 2, 1993;55(6):938-46.
Stein et al., "Comparative biodistribution and radioimmunotherapy of monoclonal antibody RS7 and its F(ab')2 in nude mice bearing human tumor xenografts", Cancer. Feb. 1, 1994;73(3 Suppl):816-23.
Stein et al., "Murine monoclonal antibodies raised against human non-small cell carcinoma of the lung: specificity and tumor targeting", Cancer Res. Feb. 15, 1990;50(4):1330-6.
Stein et al., "Effects of radiolabeling monoclonal antibodies with a residualizing iodine radiolabel on the accretion of radioisotope in tumors", Cancer Res. Jul. 15, 1995;55(14):3132-9.
Stein et al., "Successful therapy of a human lung cancer xenograft using MAb RS7 labeled with residualizing radioiodine", Rev Oncol Hematol. Jul.-Aug. 2001;39(1-2):173-80.
Stein et al., "Assessment of combined radioimmunotherapy and chemotherapy for treatment of medullary thyroid cancer", Clin Cancer Res. 5(10 Suppl):3199s-206s, 1999.
Stein et al., Characterization of the epithelial/carcinoma antigen recognized by MAb RS7. Proc. Amer. Assoc. Cancer Res. 35: 501 (Abstr. #2986), 1994.
Stein et al., A novel tumor-associated antigen defined by MAb RS7-3G11: Characterization and internalization properties. Proc. Amer. Assoc. Cancer Res. 33: 341, 1992.
Stein et al., "Characterization of cluster 13: the epithelial/carcinoma antigen recognized by MAb RS7", Int J Cancer Suppl. 1994;8:98-102.
Stein et al., "Targeting and therapy of human non small cell carcinoma of the lung xenografts using 131 I labeled monoclonal antibody RS7 3G11", Proc. Amer. Assoc. Cancer Res. 32: 260, 1991.
Van Rij et al., "Imaging of prostate cancer with immuno-PET and immuno-SPECT using a radiolabeled anti-EGP-1 monoclonal antibody", J Nucl Med. 52(10):1601-7, 2011.
Van Rij et al., "Pretargeting of prostate cancer with an internalizing anti-EGP-1 x anti-HSG bispecific antibody", Annual Congress of the European Association of Nuclear Medicine, Birmingham, UK, Eur J Nucl Med Mol Imaging 38 (Suppl 2):S212 (Abstr. #OP582), 2011.
Vanama et al., Construction, characterization, and mammalian expression of an immunotoxin consisting of ranpimase (Rap) fused to a humanized anti-EGP-1 antibody, hRS7, as a potential therapeutic for prostate cancer. Proc. Amer. Assoc. Cancer Res., 96th Annual Meeting, 160 (Abstr. #679), 2005.
Alberti et al., "Biochemical characterization of Trop-2, a cell surface molecule expressed by human carcinomas: formal proof that the monoclonal antibodies T16 and MOv-16 recognize Trop-2", Hybridoma. Oct. 1992;11(5):539-45.
Bignotti et al., "Trop-2 protein overexpression is an independent marker for predicting disease recurrence in endometrioid endometrial carcinoma", BMC Clin Pathol. Nov. 14, 2012;12:22.
Chang et al., "Ranpimase (frog RNase) targeted with a humanized, internalizing, anti-Trop-2 antibody has potent cytotoxicity against diverse epithelial cancer cells", Mol Cancer Ther. Aug. 2010;9(8):2276-86.
Chen et al., "Increased expression of Trop2 correlates with poor survival in extranodal N/KT cell lymphoma, nasal type", Virchows Arch. Nov. 2013;463(5):713-9.

(56) References Cited

OTHER PUBLICATIONS

Cubas et al., "Trop2: a possible therapeutic target for late stage epithelial carcinomas", Biochim Biophys Acta. Dec. 2009;1796(2):309-14.

Fang et al., "Different effects of ERβ and TROP2 expression in Chinese patients with early-stage colon cancer", Tumour Biol. Dec. 2012;33(6):2227-35.

Farivar et al., "Nano-drug Delivery of Apoptosis Activator 2 to AGS Cells by Liposomes Conjugated with Anti-TROP2 Antibody", N Am J Med Sci. Nov. 2012;4(11):582-5.

Friedman et al., "BR96 sFv-PE40, a potent single-chain immunotoxin that selectively kills carcinoma cells", Cancer Res. Jan. 15, 1993;53(2):334-9.

Kapoor, S., "TROP2 expression and its evolving role in tumor pathogenesis in systemic tumors", Tumour Biol. Jun. 2013;34(3):1967-8.

Lin et al., "Significantly upregulated TACSTD2 and Cyclin D1 correlate with poor prognosis of invasive ductal breast cancer", Exp Mol Pathol. Feb. 2013;94(1):73-8.

Lin et al., "A novel human Fab antibody for Trop2 inhibits breast cancer growth in vitro and in vivo", Int J Cancer. Mar. 1, 2014;134(5):1239-49.

Liu et al., "Overexpression of TROP2 predicts poor prognosis of patients with cervical cancer and promotes the proliferation and invasion of cervical cancer cells by regulating ERK signaling pathway", PLoS One. Sep. 27, 2013;8(9):e75864.

Liu et al., "Trop-2-targeting tetrakis-ranpirnase has potent antitumor activity against triple-negative breast cancer", Mol Cancer. Mar. 10, 2014;13:53.

Ning et al., "TROP2 correlates with microvessel density and poor prognosis in hilar cholangiocarcinoma", J Gastrointest Surg. Feb. 2013;17(2):360-8.

Ning et al., "TROP2 expression and its correlation with tumor proliferation and angiogenesis in human gliomas", Neurol Sci. Oct. 2013;34(10):1745-50.

Pak et al., "Significance of EpCAM and TROP2 expression in non-small cell lung cancer", World J Surg Oncol. Apr. 6, 2012;10:53.

Sapra et al., "Long-term tumor regression induced by an antibody-drug conjugate that targets 5T4, an oncofetal antigen expressed on tumor-initiating cells", Mol Cancer Ther. Jan. 2013;12(1):38-47.

Shor et al., "Enhanced Antitumor Activity of an Anti-5T4 Antibody-Drug Conjugate in Combination with PI3K/mTOR inhibitors or Taxanes", Clin Cancer Res. Jan. 15, 2016;22(2):383-94.

Shvartsur et al., "Trop2 and its overexpression in cancers: regulation and clinical/therapeutic implications", Genes Cancer. Mar. 2015;6(3-4):84-105.

Stepan et al., "Expression of Trop2 cell surface glycoprotein in normal and tumor tissues: potential implications as a cancer therapeutic target", J Histochem Cytochem. Jul. 2011;59(7):701-10.

Stoyanova et al., "Regulated proteolysis of Trop2 drives epithelial hyperplasia and stem cell self-renewal via β-catenin signaling", Genes Dev. Oct. 15, 2012;26(20):2271-85.

Tsukahara et al., "TROP2 expressed in the trunk of the ureteric duct regulates branching morphogenesis during kidney development", PLoS One. 2011;6(12):e28607.

Varughese et al., "Cervical carcinomas overexpress human trophoblast cell-surface marker (Trop-2) and are highly sensitive to immunotherapy with hRS7, a humanized monoclonal anti-Trop-2 antibody", Am J Obstet Gynecol. Dec. 2011;205(6):567.e1-7.

Vidmar et al., "Biochemical and preliminary X-ray characterization of the tumor-associated calcium signal transducer 2 (Trop2) ectodomain", Protein Expr Purif. Sep. 2013;91(1):69-76.

Wang et al., "Identification of Trop-2 as an oncogene and an attractive therapeutic target in colon cancers", Mol Cancer Ther. Feb. 2008;7(2):280-5.

Wang et al., "Loss of Trop2 promotes carcinogenesis and features of epithelial to mesenchymal transition in squamous cell carcinoma", Mol Cancer Res. Dec. 2011;9(12):1686-95.

Wu et al., "Potential therapeutic target and independent prognostic marker of TROP2 in laryngeal squamous cell carcinoma", Head Neck. Oct. 2013;35(10):1373-8.

Creative Biolabs, "Anti-Trop-2 (clone 7E6)-AcLys-VC-PABC-MMAD", Datasheet, Retrieved from WWW [http://www.creativebiolabs.net/pdf/ADC-347CL.pdf].

Strop et al., "RN927C, a Site-Specific Trop-2 Antibody-Drug Conjugate (ADC) with Enhanced Stability, Is Highly Efficacious in Preclinical Solid Tumor Models", Mol Cancer Ther. Nov. 2016;15(11):2698-2708.

\* cited by examiner

RS7Vk

```
GACATTCAGCTGACCCAGTCTCCACAAATTCATGTCCACATCAGTAGGAGACAGGGTCAGCAGGATGTGAGT           90
 1                           10                          20                30
 D  I  Q  L  T  Q  S  H  K  F  M  S  T  S  V  G  D  R  V  S  I  T  C  K  A  S  Q  D  V  S
                                                                              L1

ATTGCTGTAGCCTGGTATCAACAGAAACCAGGACAATCTCCTAAACTACTGATTTACTCGGCATCCTACCGGTACACTGGAGTCCCTGAT        180
                        40                          50                          60
 I  A  V  A  W  Y  Q  Q  K  P  G  Q  S  P  K  L  L  I  Y  S  A  S  Y  R  Y  T  G  V  P  D
    L1                                                L2

CGCTTCACTGGCAGTGGGATCTGGGACGGATTTCACTTTCACCATCAGCAGTGTGCAGGCTGAAGACCTGGCAGTTTATTACTGTCAGCAA        270
                    70                          80                          90
 R  F  T  G  S  G  S  G  T  D  F  T  F  T  I  S  S  V  Q  A  E  D  L  A  V  Y  Y  C  Q  Q

CATTATATTACTCCGCTCACGTTCGGTGCTGGGACCAAGCTGGAGCTGAAACGG           324
                    100                         108
 H  Y  I  T  P  L  T  F  G  A  G  T  K  L  E  L  K  R
        L3
```

```
GTGAAGCTGCAGGAGTCAGGACCTGAGCTGAAGAAGCCTGGAGAGACAGTCAAGATCTCCTGCAAGGCTTCTGGATATACCTTCACAAAC    90
 1                      10                      20                        30
 V  K  L  Q  E  S  G  P  E  L  K  K  P  G  E  T  V  K  I  S  C  K  A  S  G  Y  T  F  T  N
TATGGAATGAACTGGGTGAAGCAGGCTCCAGGAAAGGGTTTAAAGTGGATGGGCTGGATAAACACCTACACTGGAGAGCCAACATATACT   180
              40                      50        52                         60
 Y  G  M  N  W  V  K  Q  A  P  G  K  G  L  K  W  M  G  W  I  N  T  Y  T  G  E  P  T  Y  T
           H1                                                A
                                                                         H2
GATGACTTCAAGGGACGGTTTGCCTTCTCTTTGGAAACCTCTGCCACCACTGCCTATTTGCAGATCAACAACCTCAAAAGTGAGGACATG   270
                   70                      80     82                      90
 D  D  F  K  G  R  F  A  F  S  L  E  T  S  A  T  T  A  Y  L  Q  I  N  N  L  K  S  E  D  M
                                                    ABC
GCTACATATTTCTGTGCAAGAGGGGGTTCGGTAGCTACTGGTACTTCGATGTCTGGGGCCAAGGGACCACGGTCACCGTCTCCTCA       360
                   100                         110                113
 A  T  Y  F  C  A  R  G  G  F  G  S  S  Y  W  Y  F  D  V  W  G  Q  G  T  T  V  T  V  S  S
                   ABCD
                        H3
```

FIG. 2B

```
              1            10           20              30          40
SA-1A' cl  DIQMTQSPSSLSASVGDRVTITC|RASQSISSYLN|WYQQKP
RS7        DIQL···HKFM·T······S···|K···DV·IAVA|······
hRS7       DIQL···············S···|K···DVSIAVA|······

50           60          70          80
SA-1A' CL  GKAPKLLIY|AASSLQS|GVPSRFSGSGSGTDFTLT ISSLQP
RS7        ·QS······|S··YRTT|···D··T··········F····V·A
hRS7       ·········|S··YRYT|···D·····················

90         100      108
SA-1A' CL  EDFATYYC|QQSYSTPLT|FGGGTKVEI ──
RS7        ··L·V···|··H·I····|··A···L·LKR
hRS7       ····V···|··H·I····|··A·····IKR
```

FIG. 3A

```
            1          10          20          30          40
RF-TS3   -VQLVQSGSELKKPGASVKVSCKASGYTF|TSYAM|NWVRQA
RS7      -VKLQE··P······ET··I········|·N·G·|···K··
hRS7     QVQLG························|·N·G·|···K··

50 52A       60          70
RF-TS3   PGQGLEWMG|WINTNTGNPTYAQGFTG|RFVFSLDTSVSTAY
RS7      ··K··K···|····Y··E···TDD·K·|··A···E··AT···
hRS7     ·····K···|····Y··E···TDD·K·|··A···········

80  82ABC       90          100 A B C D 102
RF-TS3   LQISSLKADDTAVYYCAR|EDSNGYK IF-DY|
RS7      ···NN··SE·M·T·F···|GGFGSSYWYF·V|
hRS7     ················F···|GGFGSSYWYF·V|

103       110  113
NEWM     WGQGSLVTVSS
RS7      ····TT·TVSS
hRS7     ·······TVSS
```

FIG. 3B hRS7Vk

```
GACATCCAGCTGACCCAGTCTCCATCCTCCCTGTCTGCATCTGTAGGAGACAGAGTCAGTCACCTGCAAGGCCAGTCAGGATGTGAGT    90
 D  I  Q  L  T  Q  S  P  S  S  L  S  A  S  V  G  D  R  V  S  I  T  C  K  A  S  Q  D  V  S    30
                                                                        ─────────────────
                                                                                L1
ATTGCTGTAGCCTGGTATCAGCAGAAACCAGGGAAAGCCCCTAAGCTCCTGATCTACTCGGCATCCTACCGGTACACTGGAGTCCCTGAT   180
 I  A  V  A  W  Y  Q  Q  K  P  G  K  A  P  K  L  L  I  Y  S  A  S  Y  R  Y  T  G  V  P  D    60
 ─────────────                                       ───────────────
      L1                                                    L2
AGGTTCAGTGGCAGTGGATCTGGGACAGATTTCACTCTCACCATCAGCAGTCTGCAACCTGAAGATTTTGCAGTTTATTACTGTCAGCAA   270
 R  F  S  G  S  G  S  G  T  D  F  T  L  T  I  S  S  L  Q  P  E  D  F  A  V  Y  Y  C  Q  Q    90
                                                                                ─────────
                                                                                    L3
CATTATATTACTCCGCTCACGTTCGGTGCTGGGACCAAGGTGGAGATCAAACGT                                       324
 H  Y  I  T  P  L  T  F  G  A  G  T  K  V  E  I  K  R                                        108
 ──────────────
      L3
```

FIG. 4A hRS7VH

```
CAGGTCCAACTGCAGCAATCTGGGTCTGAGTTGAAGAAGCCTGGGGCCTCAGTGAAGGTTTCCTGCAAGGCTTCACA    90
 Q   V   Q   L   Q   Q   S   G   S   E   L   K   K   P   G   A   S   V   K   V   S   C   K   A   S   T     30

AACTATGGAATGAACTGGGTGAAGCAGGCCCCTGGACAAGGGCTTAAATGATGGCTGGATAAACACTTACACTGGAGAGCCAACATAT   180
 N   Y   G   M   N   W   V   K   Q   A   P   G   Q   G   L   K   W   M   G   W   I   N   T   Y   T   G   E   P   T   Y    59
                                                                          H1              H2

ACTGATGACTTCAAGGGACGGTTTGCCTTCTCCTTGGACACCTCTGTCAGCACGGCATATCTCCAGATCAGCAGCCTAAAGGCTGACGAC   270
 T   D   D   F   K   G   R   F   A   F   S   L   D   T   S   V   S   T   A   Y   L   Q   I   S   S   L   K   A   D   D     86

ACTGCCGTGTATTTCTGTGCAAGAGGGGGTTCGGTAGTAGCTACTGGTACTTCGATGTCTGGGGGCCAAGGGTCCCTGGTCACCGTCTCC   360
 T   A   V   Y   F   C   A   R   G   G   F   G   S   S   Y   W   Y   F   D   V   W   G   Q   G   S   L   V   T   V   S     112
                                H3

TCA    363
 S     113
```

FIG. 4B

```
ATGGGATGGAGCTGTATCATCCTCTTCTTGTGTAGCAACAGCTACAGGTGTCCACTCCGACATCCAGCTGACCCAGTCTCCATCCTCCCTGTCTGCATCTGTAGGAGACAGAGTCAGCATC    120
 M  G  W  S  C  I  I  L  F  L  V  A  T  A  T  G  V  H  S  D  I  Q  L  T  Q  S  P  S  S  L  S  A  S  V  G  D  R  V  S  I     40
ACCTGCAAGGCCAGTCAGGATGTGAGTATTGCTGTAGTAGCCTGGTATCAGCAGAAACCAGGGAAAGCCCCTAAGCTCCTGATCTACTCGGCATCCTACTCGGTACACTGGAGTCCCTGATAGG   240
 T  C  K  A  S  Q  D  V  S  I  A  V  A  W  Y  Q  Q  K  P  G  K  A  P  K  L  L  I  Y  S  A  S  Y  R  Y  T  G  V  P  D  R     80
TTCAGTGGCAGTGGATCTGGGACAGATTTCACTCTCACCATCAGCAGTCTGCAACCTGAAGATTTTGCAGTTTATTACTGTCAGCAACATTATATTACTCCGCTCACGTTCGGTGCTGGG       360
 F  S  G  S  G  S  G  T  D  F  T  L  T  I  S  S  L  Q  P  E  D  F  A  V  Y  Y  C  Q  Q  H  Y  I  T  P  L  T  F  G  A  G    120
ACCAAGGTGGAGATCAAACGTACTGTGGCTGCACCATCTGTCTTCATCTTCCCGCCATCTGATGAGCAGTTGAAATCTGGAACTGCCTCTGTTGTGTGCCTGCTGAATAACTTCTATCCC       480
 T  K  V  E  I  K  R  T  V  A  A  P  S  V  F  I  F  P  P  S  D  E  Q  L  K  S  G  T  A  S  V  V  C  L  L  N  N  F  Y  P    160
AGAGAGGCCAAAGTACAGTGGAAGGTGGATAACGCCCTCCAATCGGGTAACTCCCAGGAGAGTGTCACAGAGCAGGACAGCAAGGACAGCACCTACAGCCTCAGCAGCACCCTGACGCTG      600
 R  E  A  K  V  Q  W  K  V  D  N  A  L  Q  S  G  N  S  Q  E  S  V  T  E  Q  D  S  K  D  S  T  Y  S  L  S  S  T  L  T  L    200
AGCAAAGCAGACTACGAGAAACACAAAGTCTACGCCTGCGAAGTCACCCATCAGGGCCTGAGCTCGCCCGTCACAAAGAGCTTCAACAGGGGAGAGTGTTAG                         702
 S  K  A  D  Y  E  K  H  K  V  Y  A  C  E  V  T  H  Q  G  L  S  S  P  V  T  K  S  F  N  R  G  E  C  *                         233
```

FIG. 5A

```
ATGGGATGGAGCTGTATCATCCTCTTCTTGGTAGCAACAGCTACAGGTGTCCACTCCGTCCAACTGCAGCAATCTGGGTCTGAGTTGAAGAAGCCTGGGGCCTCAGTGAAGGTTTCCTGC    120
 M  G  W  S  C  I  I  L  F  L  V  A  T  A  T  G  V  H  S  V  Q  L  Q  Q  S  G  S  E  L  K  K  P  G  A  S  V  K  V  S  C    40
AAGGCTTCTGGATACACCTTCACAAACTATGGAATGAACTGGGTGAAGCAGGCCCCTGGACAAGGGCTTGAATGGATGGGCTTAAATGGGCTGGATAAACACTGGAGAGCCAACATATACTGAT    240
 K  A  S  G  Y  T  F  T  N  Y  G  M  N  W  V  K  Q  A  P  G  Q  G  L  K  W  M  G  W  I  N  T  Y  T  G  E  P  T  Y  T  D    80
GACTTCAAGGGACGGTTTGCCTTCTCCTTGGACACCTCTGTCAGCACGGCATATCTCCAGATCAGCAGCCTAAAGGCTGACGACACTGCCGTGTATTTCTGTGCAAGAGGGGGGTTCGGT    360
 D  F  K  G  R  F  A  F  S  L  D  T  S  V  S  T  A  Y  L  Q  I  S  S  L  K  A  D  D  T  A  V  Y  F  C  A  R  G  G  F  G    120
AGTAGCTACTGGTACTTCGATGTCTGGGGCCAAGGGTCCCTGGTCACCGTCTCCTCAGCCTCCACCAAGGGCCCATCCGTCTTCCCCCTGGCACCCTCCTCCAAGAGCACCTCTGGGGGC    480
 S  S  Y  W  Y  F  D  V  W  G  Q  G  S  L  V  T  V  S  S  A  S  T  K  G  P  S  V  F  P  L  A  P  S  S  K  S  T  S  G  G    160
ACAGCGGCCCTGGGCTGCCTGGTCAAGGACTACTTCCCCGAACCGGTGACGGTGTCGTGGAACTCAGGCGCCCTGACCAGCGGCGTGCACACCTTCCCGGCTGTCCTACAGTCCTCAGGA    600
 T  A  A  L  G  C  L  V  K  D  Y  F  P  E  P  V  T  V  S  W  N  S  G  A  L  T  S  G  V  H  T  F  P  A  V  L  Q  S  S  G    200
CTCTACTCCCTCAGCAGCGTGGTGACCGTGCCCTCCAGCAGCTTGGGCACCCAGACCTACATCTGCAACGTGAATCACAAGCCCAGCAACACCAAGGTGGACAAGAGAGTTGAGCCCAAA    720
 L  Y  S  L  S  S  V  V  T  V  P  S  S  S  L  G  T  Q  T  Y  I  C  N  V  N  H  K  P  S  N  T  K  V  D  K  R  V  E  P  K    240
TCTTGTGACAAAACTCACACATGCCACCTGCCCACCGTGCCCAGCACCTGAACTCCTGGGGGACCGTCAGTCTTCCTCTTCCCCCCAAAACCCAAGGACACCCTCATGATCTCCCGGACCCCTGAG    840
 S  C  D  K  T  H  T  C  P  P  C  P  A  P  E  L  L  G  G  P  S  V  F  L  F  P  P  K  P  K  D  T  L  M  I  S  R  T  P  E    280
GTCACATGCGTGGTGGTGGACGTGAGCCACGAAGACCCTGAGGTCAAGTTCAACTGGTACGTGGACGGCGTGGAGGTGCATAATGCCAAGACAAAGCCGCGGGAGGAGCAGTACAACAGC    960
 V  T  C  V  V  V  D  V  S  H  E  D  P  E  V  K  F  N  W  Y  V  D  G  V  E  V  H  N  A  K  T  K  P  R  E  E  Q  Y  N  S    320
ACGTACCGTGTGGTCAGCGTCCTCACCGTCCTGCACCAGGACTGGCTGAATGGCAAGGAGTACAAGTGCAAGGTCTCCAACAAAGCCCTCCCAGCCCCCATCGAGAAAACCATCTCCAAA    1080
 T  Y  R  V  V  S  V  L  T  V  L  H  Q  D  W  L  N  G  K  E  Y  K  C  K  V  S  N  K  A  L  P  A  P  I  E  K  T  I  S  K    360
GCCAAAGGGCAGCCCCGAGAACCACAGGTGTACACCCTGCCCCCATCCCGGGATGAGCTGACCAAGAACCAGGTCAGCCTGACCTGCCTGGTCAAAGGCTTCTATCCCAGCGACATCGCC    1200
 A  K  G  Q  P  R  E  P  Q  V  Y  T  L  P  P  S  R  E  E  M  T  K  N  Q  V  S  L  T  C  L  V  K  G  F  Y  P  S  D  I  A    400
GTGGAGTGGGAGAGCAATGGGCAGCCGGAGAACAACTACAAGACCACGCCTCCCGTGCTGGACTCCGACGGCTCCTTCTTCCTCTATAGCAAGCTCACCGTGGACAAGAGCAGGTGGCAG    1320
 V  E  W  E  S  N  G  Q  P  E  N  N  Y  K  T  T  P  P  V  L  D  S  D  G  S  F  F  L  Y  S  K  L  T  V  D  K  S  R  W  Q    440
CAGGGGAACGTCTTCTCATGCTCCGTGATGCATGAGGCTCTGCACAACCACTACACGCAGAAGAGCCTCTCCCTGTCTCCGGGTAAATGA    1410
 Q  G  N  V  F  S  C  S  V  M  H  E  A  L  H  N  H  Y  T  Q  K  S  L  S  L  S  P  G  K  *    469
```

FIG. 5B

Chart1-1. Structures of IMP-R4, IMP-R5 and IMP-R8

In the structures, 'MCC' in IMP-R1 thru IMP-R6 is 4-(N-maleimidomethyl)-cyclohexane-1-carbonyl residue; and 'MMC' in IMP-R8 is maleimidomethylcarbonyl residue; 1-((p-CSNH)benzyl)DTPA is:

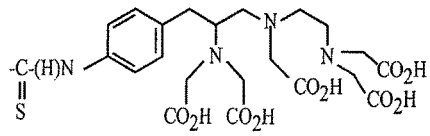

IMP-R4:   MCC-Lys(MCC)-Lys(1-((p-CSNH)benzyl)DTPA)-D-Tyr-D-Lys(1-((p-CSNH)benzyl)DTPA)-OH
IMP-R5:   MCC-Asp-D-Tyr-D-Lys(1-((p-CSNH)benzyl)DTPA)-OH
IMP-R8:   MMC-Lys(MMC)-Asp-D-Tyr-D-Lys(1-((p-CSNH)benzyl)DTPA)-OH

RS7 ANTIBODIES

This application is a divisional of U.S. patent application Ser. No. 11/745,896 (now issued U.S. Pat. No. 7,517,964), filed May 8, 2007, which is a divisional of U.S. patent application Ser. No. 10/377,121 (now issued U.S. Pat. No. 7,238,785) filed on Mar. 3, 2003, which claims priority to U.S. Provisional Application No. 60/360,299, filed Mar. 1, 2002, all of which are incorporated herein by reference in their entirety.

FIELD OF THE INVENTION

This invention relates to monovalent and multivalent, monospecific binding proteins and to multivalent, multispecific binding proteins. One embodiment of these binding proteins has one or more binding sites where each binding site binds with a target antigen or an epitope on a target antigen. Another embodiment of these binding proteins has two or more binding sites where each binding site has affinity towards different epitopes on a target antigen or has affinity towards either a target antigen or a hapten. The present invention further relates to recombinant vectors useful for the expression of these functional binding proteins in a host. More specifically, the present invention relates to the tumor-associated antigen binding protein designated RS7. The invention further relates to humanized RS7 antigen binding proteins, and the use of such binding proteins in diagnosis and therapy.

BACKGROUND OF THE INVENTION

Man-made binding proteins, in particular monoclonal antibodies and engineered antibodies or antibody fragments, have been tested widely and shown to be of value in detection and treatment of various human disorders, including cancers, autoimmune diseases, infectious diseases, inflammatory diseases, and cardiovascular diseases (Filpula and McGuire, *Exp. Opin. Ther. Patents* (1999) 9: 231-245). For example, antibodies labeled with radioactive isotopes have been tested to visualize tumors after injection to a patient using detectors available in the art. The clinical utility of an antibody or an antibody-derived agent is primarily dependent on its ability to bind to a specific targeted antigen. Selectivity is valuable for delivering a diagnostic or therapeutic agent, such as isotopes, drugs, toxins, cytokines, hormones, growth factors, enzymes, conjugates, radionuclides, or metals, to a target location during the detection and treatment phases of a human disorder, particularly if the diagnostic or therapeutic agent is toxic to normal tissue in the body.

The potential limitations of antibody systems are discussed in Goldenberg, The American Journal of Medicine (1993) 94: 298-299. The important parameters in the detection and treatment techniques are the amount of the injected dose specifically localized at the site(s) where target cells are present and the uptake ratio, i.e. the ratio of the concentration of specifically bound antibody to that of the radioactivity present in surrounding normal tissues. When an antibody is injected into the blood stream, it passes through a number of compartments as it is metabolized and excreted. The antibody must be able to locate and bind to the target cell antigen while passing through the rest of the body. Factors that control antigen targeting include location, size, antigen density, antigen accessibility, cellular composition of pathologic tissue, and the pharmacokinetics of the targeting antibodies. Other factors that specifically affect tumor targeting by antibodies include expression of the target antigens, both in tumor and other tissues, and bone marrow toxicity resulting from the slow blood-clearance of the radiolabeled antibodies. The amount of targeting antibodies accreted by the targeted tumor cells is influenced by the vascularization and barriers to antibody penetration of tumors, as well as intratumoral pressure. Non-specific uptake by non-target organs such as the liver, kidneys or bone-marrow is another potential limitation of the technique, especially for radioimmunotherapy, where irradiation of the bone marrow often causes the dose-limiting toxicity.

One suggested approach, referred to as direct targeting, is a technique designed to target specific antigens with antibodies carrying diagnostic or therapeutic radioisotopes. In the context of tumors, the direct targeting approach utilizes a radiolabeled anti-tumor monospecific antibody that recognizes the target tumor through its antigens. The technique involves injecting the labeled monospecific antibody into the patient and allowing the antibody to localize at the target tumor to obtain diagnostic or therapeutic benefits. The unbound antibody clears the body. This approach can be used to diagnose or treat additional mammalian disorders.

Another suggested solution, referred to as the "Affinity Enhancement System" (AES), is a technique especially designed to overcome deficiencies of tumor targeting by antibodies carrying diagnostic or therapeutic radioisotopes (U.S. Pat. No. 5,256,395 (1993), Barbet et al., *Cancer Biotherapy & Radiopharmaceuticals* (1999) 14: 153-166). The AES utilizes a radiolabeled hapten and an anti-tumor/anti-hapten bispecific binding protein that recognizes both the target tumor and the radioactive hapten. Haptens with higher valency and binding proteins with higher specificity may also be utilized for this procedure. The technique involves injecting the binding protein into the patient and allowing it to localize at the target tumor. After a sufficient amount of time for the unbound binding protein to clear from the blood stream, the radiolabeled hapten is administered. The hapten binds to the antibody-antigen complex located at the site of the target cell to obtain diagnostic or therapeutic benefits. The unbound hapten clears the body. Barbet mentions the possibility that a bivalent hapten may crosslink with a bispecific antibody, when the latter is bound to the tumor surface. As a result, the radiolabeled complex is more stable and stays at the tumor for a longer period of time. This system can be used to diagnose or treat mammalian disorders.

There remains a need in the art for production of multivalent, monospecific binding proteins that are useful in a direct targeting system and for production of multivalent, multispecific binding proteins that are useful in an affinity enhancement system. Specifically, there remains a need for a binding protein that exhibits enhanced uptake at targeted antigens, decreased concentration in the blood, and optimal protection of normal tissues and cells from toxic pharmaceuticals.

SUMMARY OF THE INVENTION

Accordingly, it is an object of the present invention to provide a monospecific monoclonal antibody and fragments thereof that recognizes a tumor-associated antigen, defined as epithelial glycoprotein-1 (EGP-1) by the murine MAb RS7-3G11 raised against human non-small-cell lung carcinoma. The RS7 antigen has been designated as EGP-1 (epithelial glycoprotein-1) following the proposal of the $3^{rd}$ International IASLC Workshop on Lung Tumor and Differentiation Antigens. At least one epitope associated with EGP-1 is alternatively referred to as TROP2 in the literature. In a preferred embodiment, the antibody or antibody fragment of the present invention binds the same epitope as the murine RS7 antibody disclosed by Stein (infra) and other earlier studies. Alternatively, the antibody or fragment may bind an epitope distinct from the epitope that the murine RS7 antibody disclosed by Stein binds. In a preferred embodiment, the anti-EGP-1, or anti-TROP2 antibody or fragment thereof is a chimeric, humanized, or fully human RS7 antibody or fragment thereof.

For example, contemplated in the present invention is a humanized antibody or fragment thereof, wherein the complementarity determining regions (CDRs) of the light chain variable region of the humanized RS7 MAb comprises CDR1 comprising an amino acid sequence of KASQDVSIAVA (SEQ ID NO: 28); CDR2 comprising an amino acid sequence of SASYRYT (SEQ ID NO: 29); and CDR3 comprising an amino acid sequence of QQHYITPLT (SEQ ID NO: 30). Another embodiment of the present invention is a humanized antibody or fragment thereof, wherein the CDRs of the heavy chain variable region of the humanized RS7 MAb comprises CDR1 comprising an amino acid sequence of NYGMN (SEQ ID NO: 31); CDR2 comprising an amino acid sequence of WINTYTGEPTYTDDFKG (SEQ ID NO: 32) and CDR3 comprising an amino acid sequence of GGFGSSYWYFDV (SEQ ID NO: 33). Also preferred, the humanized antibody or fragment thereof of comprises the CDRs of a murine RS7 MAb and the framework region (FR) of the light and heavy chain variable regions of a human antibody, wherein the CDRs of the light chain variable region of the humanized RS7 MAb comprises CDR1 comprising an amino acid sequence of KASQDVSIAVA (SEQ ID NO: 28); CDR2 comprising an amino acid sequence of SASYRYT (SEQ ID NO: 29); and CDR3 comprising an amino acid sequence of QQHYITPLT (SEQ ID NO: 30); and the CDRs of the heavy chain variable region of the humanized RS7 MAb comprises CDR1 comprising an amino acid sequence of NYGMN (SEQ ID NO: 31); CDR2 comprising an amino acid sequence of WINTYTGEPTYTDDFKG (SEQ ID NO: 32) and CDR3 comprising an amino acid sequence of GGFGSSYWYFDV (SEQ ID NO: 33). Still preferred, the humanized antibody or fragment thereof further comprises the FRs of the light and heavy chain constant regions of a human antibody.

In a preferred embodiment, the humanized RS7 antibody or fragment comprises a FR of a light and/or heavy chain that comprises at least one amino acid substituted by an amino acid residue found at a corresponding location in the RS7 murine antibody. For example, at least one of the substituted amino acids is preferably at a location selected from the group consisting of residue 38, 46, 68 and 91 of the murine heavy chain variable region of FIG. 3B, and/or at least one of the substituted amino acids is preferably at a location selected from the group consisting of residue 20, 85 and 100 of the murine light chain variable region of FIG. 3A.

Also described in the present invention is an antibody fission protein or fragment thereof that comprises at least two anti-EGP-1 MAb or fragments thereof, wherein the MAb or fragments thereof are selected from the anti-EGP-1 MAb or fragments thereof of the present invention. In a related vein, the antibody fusion protein or fragment thereof comprises at least one first anti-EGP-1 MAb or fragment thereof of any of the anti-EGP-1 antibodies of the present invention and at least one second MAb or fragment thereof, other than the anti-EGP antibodies or fragment thereof in the present invention. For example, the second antibody or fragment thereof may be a carcinoma-associated antibody or fragment thereof. Another preferred embodiment is a fusion protein or fragment thereof that comprises two different epitope-binding anti-EGP-1 antibodies or fragments thereof.

It is one object of this invention to provide a multispecific antibody and fragments thereof that recognize more than one epitope on the RS7 antigen or that has affinity for the RS7 antigen and for a hapten molecule. The latter binding protein is useful for pretargeting a target antigen. Accordingly, a method of delivering a diagnostic agent, a therapeutic agent, or a combination thereof to a target, comprising: (i) administering to a subject a multivalent, multispecific MAb, or fragment thereof (ii) waiting a sufficient amount of time for an amount of the non-binding protein to clear the subject's blood stream; and (iii) administering to said subject a carrier molecule comprising a diagnostic agent, a therapeutic agent, or a combination thereof, that binds to a binding site of said antibody, is also described.

It is a further object of this invention to provide a method of delivering a diagnostic or therapeutic agent to a targeted disease that expresses EGP-1 antigen. For example, a method of delivering a diagnostic or therapeutic agent, or a combination thereof, to a target comprising (i) providing a composition that comprises an anti-EGP-1 antibody or fragment thereof bound to at least one therapeutic and/or diagnostic agent and (ii) administering to a subject in need thereof said composition, is described. Preferably, the diagnostic or therapeutic agent is selected from the group consisting of an isotope, drug, toxin, immunomodulator, hormone, enzyme, growth factor, radionuclide, metal, contrast agent, and detecting agent.

In another embodiment of the present invention, the method for delivering a diagnostic agent, a therapeutic agent, or a combination thereof to a target comprises (i) administering to a subject a multivalent, multispecific antibody or fragment comprising one or more antigen-binding sites having affinity toward an EGP-1 target antigen and one or more hapten binding sites having an affinity toward a hapten molecule, (ii) waiting a sufficient amount of time for an amount of the non-binding antibody or fragment to clear a subject's blood stream, and (iii) administering to said subject a hapten comprising a diagnostic agent, a therapeutic agent, or a combination thereof.

Another object of the present invention to provide a cancer cell targeting diagnostic or therapeutic conjugate that comprises an anti-EGP-1 MAb or fragment thereof or an antibody fusion protein or fragment thereof of any one of antibodies of the present invention and wherein the anti-EGP-1 antibody or fragment thereof is bound to at least one diagnostic or therapeutic agent. A suitable therapeutic agent is a drug that possesses the pharmaceutical property selected from the group consisting of an antimitotic, alkylating, antimetabolite, antiangiogenic, apoptotic, alkaloid antibiotic, and combinations thereof. Also preferred is a therapeutic agent selected from the group consisting of a nitrogen mustard, ethylenimine derivative, alkyl sulfonate, nitrosourea, triazene, folic acid analog, anthracycline, taxane, COX-2 inhibitor, tyrosine kinase inhibitor, pyrimidine analog, purine analog, antibiotic, enzyme, epipodophyllotoxin, platinum coordination complex, vinca alkaloid, substituted urea, methyl hydrazine derivative, adrenocortical suppressant, antagonist, endostatin taxol, camptothecins, doxorubicin, doxorubicin analog, and a combination thereof. Preferably, the diagnostic agent is selected from the group consisting of a photoactive radionuclide, preferably between 25 and 4000 keV, and a contrast agent.

In a preferred embodiment, a DNA sequence comprising a nucleic acid encoding a MAb or fragment that contains a anti-EGP-1 MAb or fragment thereof of the present invention; an antibody fusion protein or fragment thereof containing at least two of said MAbs or fragments thereof; an antibody fusion protein or fragment thereof containing at least one first anti-EGP-1 MAb or fragment thereof containing the MAb or fragment thereof of the anti-EGP-1 antibodies and fragments of the present invention and at least one second MAb or fragment thereof, other than the anti-EGP-1 MAb or fragment thereof described herein; or an antibody fusion protein or fragment thereof comprising at least one first MAb or fragment thereof comprising said MAb or fragment thereof of any of the antibodies described herein and at least one second MAb or fragment thereof, other than the MAb or fragment thereof of any one of the antibodies described herein, wherein the second MAb is reactive with an antigen selected from the group consisting of EGP-2, WC 1-4, A33, CSAp, CEA, Le(y), Tn, Tag-72, PSMA, PSA, EGFR, HER2/neu, AFP, HCG, HCG-beta, ferritin, PAP, PLAP, EGP-2, histone, cytokeratin, Tenascin, CanAg, kidney cancer G 250, VGFR1, VGFR2, P4-antigen, oncogene products, or a combination thereof. The second MAb may instead be reactive with vascular endothelial antigens associated with tumors, such as VEGF (vascular endothelial growth factor) and PlGF (placenta growth factor). Selection of the second antibody is dependent on tumor cell type. For example, anti-PSMA or anti-PSA antibodies may be used for treating or diagnosing prostate cancer, anti-CEA or anti-MUC1, MUC2, MUC3 and MUC4 antibodies for breast, ovarian, lung, and colon cancer, EGFR for colon and head and neck cancers, anti-CSAp antibodies for colon and ovarian cancer, and anti-HER/neu for breast, ovarian and other cancers. These are merely given as examples, and are not intended to he limiting. Expression vectors and host cells containing this DNA sequence are also preferred embodiments of the present invention.

Also provided herein are methods for diagnosing and treating a malignancy. For example, a method for diagnosing or treating cancer, comprises (i) administering to a subject in need thereof a multivalent, multispecific antibody or fragment comprising one or more antigen-binding sites having affinity toward an EGP-1 target antigen and one or more hapten binding sites having an affinity toward a hapten molecule; (ii) waiting a sufficient amount of time for an amount of the non-binding protein to clear the subject's blood stream; and (iii) administering to said subject a hapten comprising a diagnostic agent, a therapeutic agent, or a combination thereof, that binds to a binding site of said antibody.

Likewise, the methods for diagnosing and treating a malignancy may comprise administering a therapeutically effective amount of an anti-EGP-1 fusion protein or fragment thereof or a therapeutic conjugate comprising a EGP-1 MAb or fragment thereof, wherein the EGP-1 MAb or fragment thereof or antibody fusion protein or fragment thereof is bound to at least one therapeutic agent in a pharmaceutically suitable excipient. In a related vein, naked anti-EGP-1 antibodies and fragments thereof, including naked anti-EGP-1 fusion proteins and fragments thereof, can also be used for treating a malignancy. Naked anti-EGP-1 antibodies may be used for in vitro diagnosis of a malignancy, for example with immunoassays or immunohistochemistry, but not for in vivo diagnosis, unless this involves a pretargeting technology, such as AES. Labeled EGP-1 antibodies, however, may be used for in vivo diagnosis and treatment of a malignancy. For example, described herein is a method of treating a cancer cell in a subject comprising (i) administering to a subject a therapeutically effective amount of a composition containing an anti-EGP-1 MAb or fragment thereof or an antibody fusion protein or fragment thereof (ii) formulating the EGP-1 MAb or fragment thereof or antibody fission protein or fragment thereof in a pharmaceutically suitable excipient. Similarly, combinations of naked MAbs and fragments thereof with conjugated MAbs or fragments thereof or fusion proteins or fragments thereof for diagnosis and treatment are also contemplated in the instant invention.

BRIEF DESCRIPTION OF THE DRAWINGS

FIG. 2 shows the DNA and amino acid sequences encoding (A) RS7 Vκ (SEQ ID NOS: 1-2, respectively, in order of appearance) cloned by 5' RACE and (B) RS7 VH (SEQ ID NOS: 3-4, respectively, in order of appearance) cloned by RT-PCR. The putative CDR regions are underlined and indicated. Nucleotide residues are numbered sequentially. Kabat's Ig molecule numbering is used for amino acid residues. In (B), the numbering for the residues with a letter (on top) is the number of preceding residues plus the letter, e.g., the number for T following N52 is 52A; the numbers for N, N and L following 182 are 82A, 82B and 82C, respectively.

FIG. 3 shows the amino acid sequence alignment of (A) human SA-IA'c1 (SEQ ID NO: 5), murine RS7 (SEQ ID NO: 2), and hRS7 (SEQ ID NO: 7) Vκ chains and (B) human RF-TS3 (SEQ ID NO: 8), murine RS7 (SEQ ID NO: 4, SEQ ID NO: 9), and hRS7 (SEQ ID NO: 10, SEQ ID NO: 27) $V_H$ chains. In (A), dots indicate the residues in RS7 are identical to the corresponding residues in SA-1A'c1. Dashes represent gaps introduced to aid the alignment. Boxed represent the CDR regions. Both N- and C-terminal residues (underlined) of hRS7 are fixed by the staging vector used. Therefore, the corresponding terminal residues of RS7 are not compared with that of the human sequence. Kabat's numbering scheme is used. In (B), dots indicate the residues in RS7 are identical to the corresponding residues in RF-TS3. Dashes represent gaps introduced to aid the alignment. Boxed represent the CDR regions. Both N- and C-terminal residues (underlined) of hRS7 are fixed by the staging vector used. Therefore, the corresponding terminal residues of RS7 are not compared with that of the human VH sequence.

FIG. 4 shows the DNA and amino acid sequences for (A) humanized RS7 Vκ (SEQ ID NO: 11-12, respectively, in order of appearance) and (B) humanized RS7 $V_H$ (SEQ ID NO: 13-14, respectively, in order of appearance). The bold and underlined sections of the amino acid sequences indicate the CDRs as defined by the Kabat numbering scheme.

FIG. 5 shows the (A) light chain cDNA (SEQ ID NO: 15) and amino acid (SEQ ID NO: 16) sequences for humanized RS7 Vκ and (B) heavy chain cDNA (SEQ ID NO: 17) and amino acid (SEQ ID NO: 18) sequences for humanized RS7 $V_H$. The underlined sections of the amino acid sequences indicate the leader peptide sequence for secretion. "*" indicates the stop codon.

FIG. 7 indicates the structure of the residualizing moieties IMP-R4, IMP-R5 and IMP-R8.

FIG. 10A shows the data for treatment with 0.175 mCi of hRS7 radioiodinated with a residualizing form of $^{131}$I (i.e. $^{131}$I-IMP-R4-hRS7); and FIG. 10B shows data for treatment with 0.2 mCi of hRS7 conventionally radioiodinated with $^{131}$I (i.e. $^{131}$I-hRS7). In both figures, mean white blood cell counts (solid diamond), mean lymphocyte counts (solid square), mean monocyte counts (open triangle), and mean neutrophil counts ('X'), expressed as percentage of respective mean values in untreated control animals, are shown as a function of time in weeks.

DETAILED DESCRIPTION OF THE PREFERRED EMBODIMENTS

Figure 1:
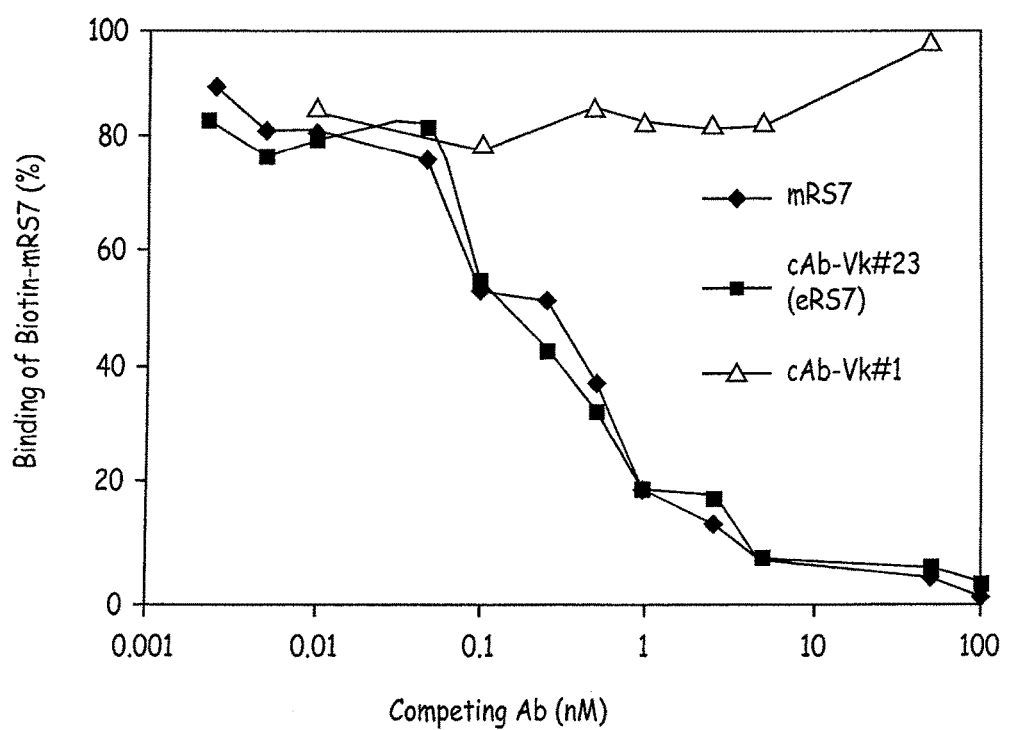
FIG. 1 shows a comparison of mRS7, cAb-Vκ#23 (cRS7), and cAb-Vκ#1 in competitive binding assays. Varying concentrations of competing Abs were used to compete with the binding of a constant amount of biotinylated mRS7 antibody. Results indicate that the Vκ#1 light chain does not bind the RS7 antigen.

Unless otherwise specified, "a" or "an" means "one or more."

An RS7 antibody (previously designated RS7-3G11) is a murine IgG$_I$ raised against a crude membrane preparation of a human primary squamous cell carcinoma from the lung. See Stein et al., Cancer Res. 50: 1330 (1990), which is fully incorporated by reference. The RS7 antibody recognizes a tumor-associated antigen, which was defined by the murine MAb RS7-3G11 raised against human non-small-cell lung carcinoma. Stein et al. discloses that the RS7 antibody recognizes a 46-48 kDa glycoprotein, characterized as cluster 13. Stein et al., Int. J. Cancer Supp. 8:98-102 (1994). See also, Basu et al., Int. J. Cancer 52:472-479 (1995). The antigen has been designated as EGP-1 (epithelial glycoprotein-1) following the proposal of the 3$^{rd}$ International IASLC Workshop on Lung Tumor and Differentiation Antigens. See, for example DeLeij et al., Int. J. Cancer Supp., 8:60-63 (1994). Accordingly, as described herein, the RS7 and EGP-1 antigens are synonymous. The EGP-1 antigen is also referred to as TROP2 in the literature, but there may be multiple epitopes of both EGP-1 and TROP2.

Flow cytometry and immunohistochemical staining studies have shown that the RS7 MAb detects antigen on a variety of tumor types, with limited binding to normal human tissue. (Stein et al., (1990), supra). The RS7 antibody is reactive with an EGP-1 glycoprotein, which can be rapidly internalized. EGP-1 is expressed primarily by carcinomas such as carcinomas of the lung, stomach, urinary bladder, breast, ovary, uterus, and prostate. Localization and therapy studies using radiolabeled murine RS7 MAb in animal models have demonstrated tumor targeting and therapeutic efficacy (Stein et al., (1990), supra. Stein et al., (1991), supra).

A more recent study has demonstrated strong RS7 staining in tumors from the lung, breast, bladder, ovary, uterus, stomach, and prostate. See Stein et al., Int. J. Cancer 55: 938 (1993), which is fully incorporated by reference. Moreover, the lung cancer cases in this study comprised both squamous cell carcinomas and adenocarcinomas. Id. Both cell types stained strongly, indicating that the RS7 antibody does not distinguish between histologic classes of non-small-cell carcinoma of the lung.

As discussed supra, the RS7 MAb is rapidly internalized into target cells (Stein et al. (1993), supra). The internalization rate constant for RS7 MAb is intermediate between the internalization rate constants of two other rapidly internalizing MAbs, which have been demonstrated to be useful for immunotoxin production. Id. It is well documented that the internalization of immunotoxin conjugates is an absolute requirement for anti-tumor activity. (Pastan et al., Cell 47:641 (1986)). Internalization of drug immunoconjugates also has been described as a major factor in anti-tumor efficacy. (Yang et al., Proc. Nat'l Acad. Sci. USA 85: 1189 (1988)). Therefore, the RS7 antigen may be an important target for those types of immunotherapy that require internalization of the therapeutic agent.

Thus, studies with the RS7 MAb indicate that the antibody exhibits several important properties, which make it a candidate for clinical diagnostic and therapeutic applications. Since the RS7 antigen provides a useful target for diagnosis and therapy, it is desirable to obtain a MAb that recognizes an epitope of the RS7 antigen. Moreover, the availability of chimeric, humanized and human RS7 antibodies is essential for the development of a double-determinant enzyme-linked immunosorbent assay (ELISA), which is desirable for detecting the RS7 antigen in clinical samples, and essential for in vivo applications in humans.

To this end, the present invention describes chimeric, humanized and human antibodies and fragments thereof that bind the RS7 antigen and can be used for diagnostic and therapeutic methods. Humanized antibodies and antibody fragments are described in Provisional U.S. Application titled "Anti-CD20 Antibodies And Fusion Proteins Thereof And Methods Of Use", U.S. Provisional Application No. 60/356,132, filed Feb. 14, 2002, and U.S. Provisional Application No. 60/416,232, filed Oct. 7, 2002, both now U.S. application Ser. No. 10/366,709, filed Feb. 4, 2003 (PGP No. US 2003-0219433-A1, now issued U.S. Pat. No. 7,151,164); hMN-14 antibodies, such as those disclosed in U.S. Pat. No. 5,874,540, which is a Class III anti-carcinoembryonic antigen antibody (anti-CEA antibody); Mu-9 antibodies, such as those described in U.S. application Ser. No. 10/116,116 (now issued U.S. Pat. No. 7,387,772), filed Apr. 5, 2002, titled "Chimeric, Human And Humanized Anti-CSAp Monoclonal Antibodies;" AFP antibodies, such as those described in U.S. Provisional Application No. 60/399,707, filed Aug. 1, 2002, titled "Alpha-Fetoprotein IMMU31 Antibodies And Fusion Proteins And Methods Of Use Thereof," now U.S. application Ser. No. 10/631,722, filed Aug. 1, 2003 (PGP No. US 2004-0235065 A1, now issued U.S. Pat. No. 7,300,655); PAM4 antibodies, such as those described in Provisional U.S. Application No. 60/388,313, filed Jun. 14, 2002 titled "Monoclonal Antibody cPAM4, now U.S. application Ser. No. 10/461,878, filed Jun. 16, 2003 (PGP No. 2004/0057902, now issued U.S. Pat. No. 7,238,786)"; RS7 antibodies, such as those described in U.S. Provisional Application No. 60/360,229, filed Mar. 1, 2002 from which this application claims priority; and CD22 antibodies, such as those disclosed in U.S. Pat. Nos. 5,789, 554 and 6,187,287 and U.S. application Ser. No. 09/741,843 (PGP No. US-2002-0102254-A1) and Ser. No. 09/988,013 (PGP No. US 2003-0103979-A1), all of which are incorporated herein by reference in their entirety. A chimeric antibody as disclosed herein is a recombinant protein that contains the variable domains including the complementarity determining regions (CDRs) of an antibody derived from one species, preferably a rodent antibody, while the constant domains of the antibody molecule is derived from those of a human antibody. For veterinary applications, the constant domains of the chimeric antibody may be derived from that of other species. A humanized antibody is a recombinant protein in which the CDRs from an antibody of one species, e.g., a rodent antibody, are transferred from the heavy and variable chains of the rodent antibody into human heavy and light variable domains.

In a preferred embodiment, the RS7 antibody is humanized. Because non-human monoclonal antibodies can be recognized by the human host as a foreign protein, and repeated injections can lead to harmful hypersensitivity reactions, humanization of a murine RS7 sequences can reduce the adverse immune response that patients may experience. For murine-based monoclonal antibodies, this is often referred to as a Human Anti-Mouse Antibody (HAMA) response. Another embodiment of the present invention is an anti-EGF-1 antibody or fragment thereof that is a subhuman primate anti-EGP-1 antibody, murine monoclonal anti-EGP-1 antibody (restricted to veterinary applications), chimeric anti-EGP-1 antibody, human anti-EGP-1 antibody, and humanized anti-EGP-1 antibody. Preferably, the chimeric, human and humanized anti-EGP-1 antibody comprises constant and hinge regions of a human IgG1. Also preferred, some human residues in the framework regions of the humanized RS7 antibody or fragments thereof are replaced by their murine counterparts. It is also preferred that a combination of framework sequences from 2 different human antibodies are used for $V_H$. The constant domains of the antibody molecule are derived from those of a human antibody.

Another preferred embodiment of the present invention is a human RS7 antibody. A human antibody is an antibody obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13 (1994), Lonberg et al., *Nature* 368:856 (1994), and Taylor et al., *Int. Immun.* 6:579 (1994). A fully human antibody also can be constructed by genetic or chromosomal transfection methods, as well as phage display technology, all of which are known in the art. See for example, McCafferty et al., *Nature* 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see e.g. Johnson and Chiswell, *Current Opinion in Structural Biology* 3:5564-571 (1993).

The antibody and fragments thereof of the present invention is preferably raised against a crude membrane preparation from a human primary squamous cell carcinoma of the lung. Also preferred, the RS7 antibody and fragments thereof is raised against a membrane preparation of viable cells from a human ovarian carcinoma cell line. Still preferred, the RS7 antigen is provided by viable Colo 316 cells. In a related vein, the RS7 antibody can be obtained using a substantially pure preparation of the RS7 antigen. A substantially pure protein is a protein that is essentially free from contaminating cellular components, which are associated with the protein in nature. As described herein, the term "RS7 antibody" also includes chimeric, human and humanized RS7 antibodies.

Preparation of Chimeric, Humanized and Human RS7 Antibodies

Monoclonal antibodies to specific antigens may be obtained by methods known to those skilled in the art. See, for example, Kohler and Milstein, *Nature* 256: 495 (1975), and Coligan et al. (eds.), *Current Protocols in Immunology*, Vol. 1, pages 2.5.1-2.6.7 (John Wiley & Sons 1991) (hereinafter "Coligan"). Briefly, RS7 antigen MAbs, such as RS7, can be obtained by injecting mice with a composition comprising the RS7 antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to RS7 antigen, culturing the clones that produce antibodies to RS7 antigen, and isolating RS7 antibodies from the hybridoma cultures.

After the initial raising of antibodies to the immunogen, the antibodies can be sequenced and subsequently prepared by recombinant techniques. Humanization and chimerization of murine antibodies and antibody fragments are well known to those skilled in the art. For example, humanized monoclonal antibodies are produced by transferring mouse complementary determining regions from heavy and light variable chains of the mouse immunoglobulin into a human variable domain, and then, substituting human residues in the framework regions of the murine counterparts. The use of antibody components derived from humanized monoclonal antibodies obviates potential problems associated with the immunogenicity of murine constant regions.

A human antibody of the present invention, i.e., human EGP-1 MAbs or other human antibodies, such as anti-EGP-2, MUC1-4, CEA, CC49, CSAp, PSMA, PSA, EGFR, A33 and HER2/neu MAbs for combination therapy with humanized, chimeric or human RS7 antibodies, can be obtained from a transgenic non-human animal. See, e.g., Mendez et al., *Nature Genetics,* 15: 146-156 (1997); U.S. Pat. No. 5,633,425, which are incorporated in their entirety by reference. A human antibody of the present invention that can be used for combination therapy may also be reactive with an antigen selected from the group consisting of Le(y), Tn, Tag-72, AFP, HCG, HCG-beta, ferritin, PAP, EGP-2, histone, cytokeratin, Tenascin, CanAg, kidney cancer G 250, VGFR1, VGFR2, or a combination thereof. For example, a human antibody can be recovered from a transgenic mouse possessing human immunoglobulin loci. The mouse humoral immune system is humanized by inactivating the endogenous immunoglobulin genes and introducing human immunoglobulin loci. The human immunoglobulin loci are exceedingly complex and comprise a large number of discrete segments which together occupy almost 0.2% of the human genome. To ensure that transgenic mice are capable of producing adequate repertoires of antibodies, large portions of human heavy- and light-chain loci must be introduced into the mouse genome. This is accomplished in a stepwise process beginning with the formation of yeast artificial chromosomes (YACs) containing either human heavy- or light-chain immunoglobulin loci in germline configuration. Since each insert is approximately 1 Mb in size, YAC construction requires homologous recombination of overlapping fragments of the immunoglobulin loci. The two YACs, one containing the heavy-chain loci and one containing the light-chain loci, are introduced separately into mice via fusion of YAC-containing yeast spheroblasts with mouse embryonic stem cells. Embryonic stem cell clones are then microinjected into mouse blastocysts. Resulting chimeric males are screened for their ability to transmit the YAC through their germline and are bred with mice deficient in murine antibody production. Breeding the two transgenic strains, one containing the human heavy-chain loci and the other containing the human light-chain loci, creates progeny, which produce human antibodies in response to immunization.

General techniques for cloning murine immunoglobulin variable domains are described, for example, by the publication of Orlandi et al., *Proc. Nat'l Acad. Sci. USA* 86: 3833 (1989), which is incorporated by reference in its entirety. Techniques for producing humanized MAbs are described, for example, by Carter et al., *Proc. Nat'l Acad. Sci. USA* 89: 4285 (1992), Singer et al., *J. Immun.* 150: 2844 (1992), Mountain et al. *Biotechnol. Genet. Eng. Rev.* 10:1 (1992), and Coligan at pages 10.19.1-10.19.11, each of which is hereby incorporated by reference.

In general, the Vκ (variable light chain) and $V_H$ (variable heavy chain) sequences for RS7 antibodies can be obtained by a variety of molecular cloning procedures, such as RT-PCR, 5'-RACE, and cDNA library screening. Specifically, the VH and Vκ genes of the MAb RS7 were cloned by PCR amplification from the hybridoma cells by RT-PCR and 5' RACE, respectively, and their sequences determined by DNA sequencing. To confirm their authenticity, the cloned $V_L$ and $V_H$ genes can be expressed in cell culture as a chimeric Ab as described by Orlandi et al., (*Proc. Natl. Acad. Sci., USA,* 86: 3833 (1989)) which is incorporated by reference. Based on the V gene sequences, a humanized RS7 antibody can then be designed and constructed as described by Leung et at. (*Mol. Immunol.,* 32: 1413 (1995)), which is incorporated by reference. cDNA can be prepared from any known hybridoma line or transfected cell line producing a murine or chimeric RS7 antibody by general molecular cloning techniques (Sambrook et al., Molecular Cloning, A laboratory manual, $2^{nd}$ Ed (1989)). In a preferred embodiment, the RS7 hybridoma line is used. The Vκ sequence for the mAb may be amplified using the primers VK1BACK and VK1FOR (Orlandi et al., 1989) or the extended primer set described by Leung et at. (*BioTechniques,* 15: 286 (1993)), which is incorporated by reference, while $V_H$ sequences can be amplified using the primer pair VH1BACK/VH1FOR (Orlandi et al., 1989 above), or the primers annealing to the constant region of murine IgG described by Leung et al. (Hybridoma, 13:469 (1994)), which is incorporated by reference. The PCR reaction mixtures containing 10 µl of the first strand cDNA product, 10 µl of 10×PCR buffer [500 mM KCl, 100 mM Tris-HCl(pH 8.3), 15 mM $MgCl_2$, and 0.01% (w/v) gelatin] (Perkin Elmer Cetus, Norwalk, Conn.), 250 µM of each dNTP, 200 nM of the primers, and 5 units of Taq DNA polymerase (Perkin Elmer Cetus) can be subjected to 30 cycles of PCR. Each PCR cycle preferably consists of denaturation at 94° C. for 1 min, annealing at 50° C. for 1.5 min, and polymerization at 72° C. for 1.5 min. Amplified Vκ and $V_H$ fragments can be purified on 2% agarose (BioRad, Richmond, Calif.). Similarly, the humanized V genes can be constructed by a combination of long oligonucleotide template syntheses and PCR amplification as described by Leung et al. (*Mol. Immunol.,* 32: 1413 (1995)).

PCR products for Vκ can be subcloned into a staging vector, such as a pBR327-based staging vector, VKpBR, that contains an Ig promoter, a signal peptide sequence and convenient restriction sites to facilitate in-frame ligation of the Vκ PCR products. PCR products for $V_H$ can be subcloned into a similar staging vector, such as the pBluescript-based VHpBS. Individual clones containing the respective PCR products may be sequenced by, for example, the method of Sanger et al. (*Proc. Natl. Acad. Sci., USA,* 74: 5463 (1977)), which is incorporated by reference.

The DNA sequences described herein are to be taken as including all alleles, mutants and variants thereof, whether occurring naturally or induced.

The expression cassettes containing the Vκ and VH, together with the promoter and signal peptide sequences can be excised from VKpBR and VHpBS, respectively, by double restriction digestion as HindIII-BamHI fragments. The Vκ and VH expression cassettes can then be ligated into appropriate expression vectors, such as pKh and pG1g, respectively (Leung et al., Hybridoma, 13:469 (1994)). The expression vectors can be co-transfected into an appropriate cell, e.g., myeloma Sp2/0-Ag14 (ATCC, VA), colonies selected for hygromycin resistance, and supernatant fluids monitored for production of a chimeric or humanized RS7 MAb by, for example, an ELISA assay, as described below. Alternately, the Vκ and VH expression cassettes can be assembled in the modified staging vectors, VKpBR2 and VHpBS2, excised as XbaI/BamHI and XhoI/BamHI fragments, respectively, and subcloned into a single expression vector, such as pdHL2, as described by Gilles et al. (*J. Immunol. Methods* 125:191 (1989) and also shown in Losman et al., *Cancer,* 80:2660 (1997)) for the expression in Sp2/0-Ag14 cells. Another vector that is useful in the present invention is the GS vector, as described in Barnes et al., *Cytotechnology* 32:109-123 (2000), which is preferably expressed in the NSO cell line and CHO cells. Other appropriate mammalian expression systems are described in Werner et al., Arzneim.-Forsch./Drug Res. 48(II), Nr. 8, 870-880 (1998).

Co-transfection and assay for antibody secreting clones by ELISA, can be carried out as follows. About 10 µg of VKpKh (light chain expression vector) and 20 µg of VHpG1g (heavy chain expression vector) can be used for the transfection of $5 \times 10^6$ SP2/0 myeloma cells by electroporation (BioRad, Richmond, Calif.) according to Co et al., *J. Immunol.*, 148: 1149 (1992) which is incorporated by reference. Following transfection, cells may be grown in 96-well microtiter plates in complete HSFM medium (Life Technologies, Inc., Grand Island, N.Y.) at 37° C., 5% $CO_2$. The selection process can be initiated after two days by the addition of hygromycin selection medium (Calbiochem, San Diego, Calif.) at a final concentration of 500 units/ml of hygromycin. Colonies typically emerge 2-3 weeks post-electroporation. The cultures can then be expanded for further analysis.

Suitable host cells include microbial or mammalian host cells. A preferred host is the human cell line, PER.C6, which was developed for production of MAbs, and other fusion proteins. Accordingly, a preferred embodiment of the present invention is a host cell comprising a DNA sequence encoding and anti-EGP-1 MAb, conjugate, fusion protein or fragments thereof. PER.C6 cells (WO 97/00326) were generated by transfection of primary human embryonic retina cells, using a plasmid that contained the Adserotype 5 (Ad5) E1A- and E1B-coding sequences (Ad5 nucleotides 459-3510) under the control of the human phosphoglycerate kinase (PGK) promoter. E1A and E1B are adenovirus early gene activation protein 1A and 1B, respectively. The methods and compositions are particularly useful for generating stable expression of human recombinant proteins of interest that are modified post-translationally, e.g. by glycosylation. Several features make PER.C6 particularly useful as a host for recombinant protein production, such as PER.C6 is a fully characterized human cell line and it was developed in compliance with good laboratory practices. Moreover, PER.C6 can be grown as a suspension culture in defined serum-free medium devoid of any human- or animal-derived proteins and its growth is compatible with roller bottles, shaker flasks, spinner flasks and bioreactors with doubling times of about 35 hrs. Finally, the presence of E1A causes an up regulation of expression of genes that are under the control of the CMV enhancer/promoter and the presence of E13 prevents p53-dependent apoptosis possibly enhanced through over expression of the recombinant transgene. In one embodiment, the cell is capable of producing 2 to 200-fold more recombinant protein and/or proteinaceous substance than conventional mammalian cell lines.

Transfectoma clones that are positive for the secretion of chimeric or humanized heavy chain can be identified by ELISA assay. Briefly, supernatant samples (~100 μl) from transfectoma cultures are added in triplicate to ELISA microtiter plates precoated with goat anti-human (GAH)-IgG, F(ab')$_2$ fragment-specific antibody (Jackson ImmunoResearch, West Grove, Pa.). Plates are incubated for 1 hr at room temperature. Unbound proteins are removed by washing three times with wash buffer (PBS containing 0.05% polysorbate 20). Horseradish peroxidase (HRP) conjugated GAH-IgG, Fc fragment-specific antibodies (Jackson ImmunoResearch) are added to the wells, (100 μl of antibody stock diluted$\times 10^4$, supplemented with the unconjugated antibody to a final concentration of 1.0 μg/ml). Following an incubation of 1 h, the plates are washed, typically three times. A reaction solution, [100 μl, containing 167 μg of orthophenylenediamine (OPD) (Sigma, St. Louis, Mo.), 0.025% hydrogen peroxide in PBS], is added to the wells. Color is allowed to develop in the dark for 30 minutes. The reaction is stopped by the addition of 50 μl of 4 N HCl solution into each well before measuring absorbance at 490 nm in an automated ELISA reader (Bio-Tek instruments, Winooski, Vt.). Bound chimeric antibodies are than determined relative to an irrelevant chimeric antibody standard (obtainable from Scotgen, Ltd., Edinburg, Scotland).

Antibodies can be isolated from cell culture media as follows. Transfectoma cultures are adapted to serum-free medium. For production of chimeric antibody, cells are grown as a 500 ml culture in roller bottles using HSFM. Cultures are centrifuged and the supernatant filtered through a 0.2μ membrane. The filtered medium is passed through a protein A column (1×3 cm) at a flow rate of 1 ml/min. The resin is then washed with about 10 column volumes of PBS and protein A-bound antibody is eluted from the column with 0.1 M glycine buffer (pH 3.5) containing 10 mM EDTA. Fractions of 1.0 ml are collected in tubes containing 10 μl of 3 M Tris (pH 8.6), and protein concentrations determined from the absorbance at 280/260 nm. Peak fractions are pooled, dialyzed against PBS, and the antibody concentrated, for example, with the Centricon 30 (Amicon, Beverly, Mass.). The antibody concentration is determined by ELISA, as before, and its concentration adjusted to about 1 mg/ml using PBS. Sodium azide, 0.01% (w/v), is conveniently added to the sample as preservative.

The nucleotide sequences of the primers used to prepare the RS7 antibodies are listed in Example 2, below. In a preferred embodiment, a humanized RS7 antibody or antibody fragment comprises the complementarity-determining regions (CDRs) of a murine RS7 MAb and the framework (FR) regions of the light and heavy chain variable regions of a human antibody and the light and heavy chain constant regions of a human antibody, wherein the CDRs of the light chain variable region of the humanized RS7 comprises CDR1 comprising an amino acid sequence of KASQDVSIAVA (SEQ ID NO: 28); CDR2 comprising an amino acid sequence of SASYRYT (SEQ ID NO: 29); and CDR3 comprising an amino acid sequence of QQHYITPLT (SEQ ID NO: 30); and the CDRs of the heavy chain variable region of the humanized RS7 MAb comprises CDR1 comprising an amino acid sequence of NYGMN (SEQ ID NO: 31); CDR2 comprising an amino acid sequence of WINTYTGEPTYTDDFKG (SEQ ID NO: 32) and CDR3 comprising an amino acid sequence of GGFGSSYWYFDV (SEQ ID NO: 33). Also preferred, the FRs of the light and heavy chain variable regions of the humanized antibody comprise at least one amino acid substituted from said corresponding FRs of the murine RS7 MAb.

RS7 MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in *Methods in Molecular Biology*, Vol. 10, pages 79-104 (The Humana Press, Inc. 1992).

RS7 MAbs can be characterized by a variety of techniques that are well-known to those of skill in the art. For example, the ability of an RS7 MAb to bind to the RS7 antigen can be verified using an indirect immunofluorescence assay, flow cytometry analysis, or Western analysis.

Production of RS7 Antibody Fragments

The present invention contemplates the use of fragments of RS7 and hRS7 antibodies. Antibody fragments, which recognize specific epitopes, can be generated by known techniques. The antibody fragments are antigen binding portions of an antibody, such as F(ab')$_2$, Fab', Fab, Fv, sFv and the like. Other antibody fragments include, but are not limited to: the F(ab)'$_2$ fragments which can be produced by pepsin digestion of the antibody molecule and the Fab' fragments, which can be generated by reducing disulfide bridges of the F(ab)'$_2$ fragments. These methods are described, for example, by Goldenberg, U.S. Pat. Nos. 4,036,945 and 4,331,647 and references contained therein, which patents are incorporated herein in their entireties by reference. Also, see Nisonoff et al., *Arch Biochem. Biophys.* 89: 230 (1960); Porter, *Biochem. J.* 73: 119 (1959), Edelman et al., in *Methods in Enzymology*, Vol. 1, page 422 (Academic Press 1967), and Coligan at pages 2.8.1-2.8.10 and 2.10.-2.10.4. Alternatively, Fab' expression libraries can be constructed (Huse et al., 1989, *Science*, 246:1274-1281) to allow rapid and easy identification of monoclonal Fab' fragments with the desired specificity. The present invention encompasses antibodies and antibody fragments.

A single chain Fv molecule (scFv) comprises a VL domain and a VH domain. The VL and VH domains associate to form a target binding site. These two domains are further covalently linked by a peptide linker (L). A scFv molecule is denoted as either VL-L-VH if the VL domain is the N-terminal part of the scFv molecule, or as VH-L-VL if the VH domain is the N-terminal part of the scFv molecule. Methods for making scFv molecules and designing suitable peptide linkers are described in U.S. Pat. No. 4,704,692, U.S. Pat. No. 4,946,778, R. Raag and M. Whitlow, "Single Chain Fvs." *Faseb*, Vol. 9:73-80 (1995) and R. E. Bird and B. W. Walker, "*Single Chain Antibody Variable Regions,*" *TibTech*, Vol. 9: 132-137 (1991). These references are incorporated herein by reference.

An antibody fragment can be prepared by proteolytic hydrolysis of the full length antibody or by expression in *E. coli* or another host of the DNA coding for the fragment. An antibody fragment can be obtained by pepsin or papain digestion of full length antibodies by conventional methods. For example, an antibody fragment can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5 S Fab' monovalent fragments. Alternatively, an enzymatic cleavage using papain produces two monovalent Fab fragments and an Fc fragment directly. These methods are described, for example, by Goldenberg, U.S. Pat. Nos. 4,036,945 and 4,331,647 and references contained therein, which patents are incorporated herein in their entireties by reference. Also, see Nisonoff et al., *Arch Biochem. Biophys.* 89: 230 (1960); Porter, *Biochem. J.* 73: 119 (1959), Edelman et al., in *Methods in Enzymology*, Vol. 1, page 422 (Academic Press 1967), and Coligan at pages 2.8.1-2.8.10 and 2.10.-2.10.4.

Another form of an antibody fragment is a peptide coding for a single complementarity-determining region (CDR). A CDR is a segment of the variable region of an antibody that is complementary in structure to the epitope to which the antibody binds and is more variable than the rest of the variable region. Accordingly, a CDR is sometimes referred to as hypervariable region. A variable region comprises three CDRs. CDR peptides can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: A Companion to Methods in Enzymology* 2: 106 (1991); Courtenay-Luck, "Genetic Manipulation of Monoclonal Antibodies," in *Monoclonal Antibodies: Production, Engineering and Clinical Application*, Ritter et al. (eds.), pages 166-179 (Cambridge University Press 1995); and Ward et al., "Genetic Manipulation and Expression of Antibodies," in *Monoclonal Antibodies: Principles and Applications*, Birch et al., (eds.), pages 137-185 (Wiley-Liss, Inc. 1995).

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

Production of Chimeric, Humanized and Human RS7 Antibody Fusion Proteins

Antibody fusion proteins and fragments thereof can be prepared by a variety of conventional procedures, ranging from glutaraldehyde linkage to more specific linkages between functional groups. The antibodies and/or antibody fragments are preferably covalently bound to one another, directly or through a linker moiety, through one or more functional groups on the antibody or fragment, e.g., amine, carboxyl, phenyl, thiol, or hydroxyl groups. Various conventional linkers in addition to glutaraldehyde can be used, e.g., disiocyanates, diiosothiocyanates, bis(hydroxysuccinimide) esters, carbodiimides, maleimidehydroxysuccinimide esters, and the like.

A simple method to produce chimeric, humanized and human RS7 antibody fusion proteins is to mix the antibodies or fragments in the presence of glutaraldehyde to form an antibody fusion protein. The initial Schiff base linkages can be stabilized, e.g., by borohydride reduction to secondary amines. A diiosothiocyanate or carbodiimide can be used in place of glutaraldehyde as a non-site-specific linker. Antibody fusion proteins are expected to have a greater binding specificity than MAbs, since the fusion proteins comprise moieties that bind to at least two epitopes of the RS7 antigen. Thus, antibody fusion proteins are the preferred form of RS7 antigen binding protein for therapy.

In the present context, an antibody fusion protein comprises at least two chimeric, humanized or human RS7 MAbs, or fragments thereof, wherein at least two of the MAbs or fragments bind to different epitopes of the RS7 antigen or against an RS7 epitope and that of a totally different antigen. For example, a bispecific RS7 antibody fusion protein may comprise a CEA antibody or fragment thereof and the RS7 MAb or fragment thereof. Such a bispecific RS7 antibody fusion protein can be prepared, for example, by obtaining an F(ab')$_2$ fragment from CEA as described above. The interchain disulfide bridges of the antibody F(ab')$_2$ fragment are gently reduced with cysteine, taking care to avoid light-heavy chain linkage, to form Fab'-SH fragments. The SH group(s) is (are) activated with an excess of bis-maleimide linker (1,1'-(methylenedi-4,1-phenylene)bis-malemide). The RS7 MAb is converted to Fab'-SH and then reacted with the activated CEA Fab'-SH fragment to obtain a bispecific RS7 antibody fusion protein.

A polyspecific RS7 antibody fusion protein can be obtained by adding RS7 antigen binding moieties to a bispecific chimeric, humanized or human RS7 antibody fusion protein. For example, a bispecific antibody fusion protein can be reacted with 2-iminothiolane to introduce one or more sulfhydryl groups for use in coupling the bispecific fusion protein to a third RS7 antigen MAb or fragment, using the bis-maleimide activation procedure described above. These techniques for producing antibody composites are well known to those of skill in the art. See, for example, U.S. Pat. No. 4,925,648, which is incorporated by reference in its entirety.

Bispecific antibodies can be made by a variety of conventional methods, e.g., disulfide cleavage and reformation of mixtures of whole IgG or, preferably F(ab')$_2$ fragments, fusions of more than one hybridoma to form polyomas that produce antibodies having more than one specificity, and by genetic engineering. Bispecific antibody fusion proteins have been prepared by oxidative cleavage of Fab' fragments resulting from reductive cleavage of different antibodies. This is advantageously carried out by mixing two different F(ab')$_2$ fragments produced by pepsin digestion of two different antibodies, reductive cleavage to form a mixture of Fab' fragments, followed by oxidative reformation of the disulfide linkages to produce a mixture of F(ab')$_2$ fragments including bispecific antibody fusion proteins containing a Fab' portion specific to each of the original epitopes. General techniques for the preparation of antibody fusion proteins may be found, for example, in Nisonoff et al., *Arch Biochem. Biophys.* 93: 470 (1961), Hammerling et al., 1 *Exp. Med.* 128: 1461 (1968), and U.S. Pat. No. 4,331,647. Contemplated in the present invention is an antibody fusion protein or fragment thereof comprising at least one first anti-EGP-1 MAb or fragment thereof and at least one second MAb or fragment thereof, other than the anti-EGP-1 MAbs or fragments thereof of the present invention.

More selective linkage can be achieved by using a heterobifunctional linker such as maleimidehydroxysuccinimide ester. Reaction of the ester with an antibody or fragment will derivatize amine groups on the antibody or fragment, and the derivative can then be reacted with, e.g., and antibody Fab fragment having free sulfhydryl groups (or, a larger fragment or intact antibody with sulfhydryl groups appended thereto by, e.g., Traut's Reagent). Such a linker is less likely to crosslink groups in the same antibody and improves the selectivity of the linkage.

It is advantageous to link the antibodies or fragments at sites remote from the antigen binding sites. This can be accomplished by, e.g., linkage to cleaved interchain sulfydryl groups, as noted above. Another method involves reacting an antibody having an oxidized carbohydrate portion with another antibody, which has at lease one free amine function. This results in an initial Schiff base (mime) linkage, which is preferably stabilized by reduction to a secondary amine, e.g., by borohydride reduction, to form the final composite. Such site-specific linkages are disclosed, for small molecules, in U.S. Pat. No. 4,671,958, and for larger addends in U.S. Pat. No. 4,699,784—incorporated by reference.

ScFvs with linkers greater than 12 amino acid residues in length (for example, 15- or 18-residue linkers) allow interacting between the $V_H$ and $V_L$ domains on the same chain and generally form a mixture of monomers, dimers (termed diabodies) and small amounts of higher mass multimers, (Kortt et al., Eur. J. Biochem. (1994) 221: 151-157). ScFvs with linkers of 5 or less amino acid residues, however, prohibit intramolecular pairing of the $V_H$ and $V_L$ domains on the same chain, forcing pairing with $V_H$ and $V_L$ domains on a different chain. Linkers between 3- and 12-residues form predominantly dimers (Atwell et al., Protein Engineering (1999) 12: 597-604). With linkers between 0 and 2 residues, trimeric (termed triabodies), tetrameric (termed tetrabodies) or higher oligomeric structures of scFvs are formed; however, the exact patterns of oligomerization appear to depend on the composition as well as the orientation of the V-domains, in addition to the linker length. For example, scFvs of the anti-neuraminidase antibody NC 10 formed predominantly trimers ($V_H$ to $V_L$ orientation) or tetramers ($V_L$ to $V_H$ orientation) with O-residue linkers (Dolezal et al., Protein Engineering (2000) 13: 565-574). For scFvs constricted from NC10 with 1- and 2-residue linkers, the $V_H$ to $V_L$ orientation formed predominantly diabodies (Atwell et al., Protein Engineering (1999) 12: 597-604); in contrast, the $V_L$ to $V_H$ orientation formed a mixture of tetramers, trimers, dimers, and higher mass multimers (Dolezal et al., Protein Engineering (2000) 13: 565-574). For scFvs constructed from the anti-CD 19 antibody HD37 in the $V_H$ to $V_L$, orientation, the O-residue linker formed exclusively trimers and the 1-residue linker formed exclusively tetramers (Le Gall et al., FEBS Letters (1999) 453: 164-168).

The RS7 antibodies and fragments thereof of the present invention can also be used to produce antigen-specific diabodies, triabodies and tetrabodies, which are multivalent but monospecific. The non-covalent association of two or more scFv molecules can form functional diabodies, triabodies and tetrabodies. Monospecific diabodies are homodimers of the same scFv, where each scFv comprises the $V_H$ domain from the selected antibody connected by a short linker to the $V_L$ domain of the same antibody. A diabody is a bivalent dimer formed by the non-covalent association of two scFvs, yielding two Fv binding sites. A triabody results from the formation of a trivalent trimer of three scFvs, yielding three binding sites, and a tetrabody is a tetravalent tetramer of four scFvs, resulting in four binding sites. Several monospecific diabodies have been made using an expression vector that contains a recombinant gene construct comprising $V_{H1}$-linker-$V_{L1}$. See Holliger et al., *Proc. Natl. Acad. Sci. USA* 90: 6444-6448 (1993); Atwell et al., *Molecular Immunology* 33: 1301-1302 (1996); Holliger et al., *Nature Biotechnology* 15: 632-631 (1997); Helfrich et al., *Int. J. Cancer* 76: 232-239 (1998); Kipriyanov et al., *Int. J. Cancer* 77: 763-772 (1998); Holiger et al., *Cancer Research* 59: 2909-2916 (1999)). Methods of constructing scFvs are disclosed in U.S. Pat. No. 4,946,778 (1990) and U.S. Pat. No. 5,132,405 (1992). Methods of producing multivalent, monospecific binding proteins based on scFv are disclosed in U.S. Pat. No. 5,837,242 (1998) and U.S. Pat. No. 5,844,094 (1998) and WO-98/44001 (1998). A preferred embodiment of the instant invention is a multivalent, multispecific antibody or fragment thereof comprising one or more antigen binding sites having affinity toward an EGP-1 target antigen and one or more hapten binding sites having affinity towards hapten molecules.

Determining Antibody Binding Affinity

Comparative binding affinities of the mRS7, cRS7 and hRS7 antibodies thus isolated may be determined by direct radioimmunoassay. RS7 can be labeled with $^{131}$I or $^{125}$I using the chloramines-T method (see, for example, Greenwood et al., *Biochem. J.*, 89: 123 (1963) which is incorporated by reference). The specific activity of the iodinated antibody is typically adjusted to about 10 µCi/1 g. Unlabeled and labeled antibodies are diluted to the appropriate concentrations using reaction medium (HSFM supplemented with 1% horse serum and 100 µg/ml gentamicin). The appropriate concentrations of both labeled and unlabeled antibodies are added together to the reaction tubes in a total volume of 100 µl. A culture of ME180 cells (a human cervical carcinoma cell line) is sampled and the cell concentration determined. The culture is centrifuged and the collected cells washed once in reaction medium followed by resuspension in reaction medium to a final concentration of about $10^7$ cells/ml. All procedures are carried out in the cold at 4° C. The cell suspension, 100 µl, is added to the reaction tubes. The reaction is carried out at 4° C. for 2 h with periodic gentle shaking of the reaction tubes to resuspend the cells. Following the reaction period, 5 ml of wash buffer (PBS containing 1% BSA) is added to each tube. The suspension is centrifuged and the cell pellet washed a second time with another 5 ml of wash buffer. Following centrifugation, the amount of remaining radioactivity remaining in the cell pellet is determined in a gamma counter (Minaxi, Packard Instruments, Sterling, Va.).

Expression Vectors

An expression vector is a DNA molecule comprising a gene that is expressed in a host cell. Typically, gene expression is placed under the control of certain regulatory elements, including constitutive or inducible promoters, tissue-specific regulatory elements, and enhancers. Such a gene is said to be "operably linked to" the regulatory elements. A promoter is a DNA sequence that directs the transcription of a structural gene. A structural gene is a DNA sequence that is transcribed into messenger RNA (mRNA) which is then translated into a sequence of amino acids characteristic of a specific polypeptide. Typically, a promoter is located in the 5' region of a gene, proximal to the transcriptional start site of a structural gene. If a promoter is an inducible promoter, then the rate of transcription increases in response to an inducing agent. In contrast, the rate of transcription is not regulated by an inducing agent if the promoter is a constitutive promoter. An enhancer is a DNA regulatory element that can increase the efficiency of transcription, regardless of the distance or orientation of the enhancer relative to the start site of transcription.

An isolated DNA molecule is a fragment of DNA that is not integrated in the genomic DNA of an organism. For example, a cloned RS7 antigen gene is a DNA fragment that has been separated from the genomic DNA of a mammalian cell. Another example of an isolated DNA molecule is a chemically-synthesized DNA molecule that is not integrated in the genomic DNA of an organism. Complementary DNA (cDNA) is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand.

A cloning vector is a DNA molecule, such as a plasmid, cosmid, or bacteriophage that has the capability of replicating autonomously in a host cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include genes that provide tetracycline resistance or ampicillin resistance. A recombinant host may be any prokaryotic or eukaryotic cell that contains either a cloning vector or expression vector. This term also includes those prokaryotic or eukaryotic cells that have been genetically engineered to contain the cloned gene(s) in the chromosome or genome of the host cell. The term expression refers to the biosynthesis of a gene product. For example, in the case of a structural gene, expression involves transcription of the structural gene into mRNA and the translation of mRNA into one or more polypeptides.

Humanized, Human and Chimeric RS7 Antibodies Use for Treatment and Diagnosis

Contemplated in the present invention is a method of diagnosing or treating a malignancy in a subject comprising administering to the subject a therapeutically effective amount of a therapeutic conjugate comprising an EGP-1 MAb or fragment thereof or an antibody fusion protein or fragment thereof, wherein the EGP-MAb or fragment thereof or antibody fusion protein or fragment thereof is bound to at least one therapeutic agent and then formulated in a pharmaceutically suitable excipient. It is also contemplated that an unconjugated (naked) EGP-1 MAb or fusion construct with other antigen-binding moieties also can be sued as a therapeutic for cancer cells expressing EGP-1. These unconjugated antibodies may be given advantageously in combination with other therapeutic modalities, such as chemotherapy, radiotherapy, and/or immunotherapy, either together or in various sequences and schedules. Also preferred is a method for diagnosing or treating cancer, comprising: administering a multivalent, multi specific antibody or fragment thereof comprising one or more antigen binding sites toward a EGP-1 antigen and one or more hapten binding sites to a subject in need thereof, waiting a sufficient amount of time for an amount of the non-binding protein to clear the subject's blood stream; and then administering to the subject a carrier molecule comprising a diagnostic agent, a therapeutic agent, or a combination thereof, that binds to the binding site of the multivalent, multispecific antibody or fragment thereof. In a preferred embodiment, the cancer is a lung, breast, head and neck, ovarian, prostate, bladder or colon cancer.

Hybridoma technology for the production of monoclonal antibodies (MAbs) has provided a method for the production of molecular probes capable of locating or killing cancer cells. Tumor imaging techniques using radiolabeled MAbs have been used to delineate cancerous invasion in a number of malignancies. In experimental animals and in humans, antibodies have been used for the radioimmunodetection of carcinoembryonic antigen in diverse tumors that express carcinoembryonic antigen, and also tumors such as melanoma, colon carcinoma, and breast carcinoma with other targeting antibodies. Goldenberg et al., *Cancer Res.* 40: 2984 (1980); Hwang et al., *Cancer Res.* 45: 4150 (1985); Zalcberg et al., *J. Nat'l Cancer Inst.* 71: 801 (1983); Colcher et al., *Cancer Res.* 43: 736 (1983); (Larson et al., *J. Nucl. Med.* 24: 123 (1983); DeLand et al., *Cancer Res.* 40: 3046 (1980); Epenetos et al., *Lancet* 2: 999 (1982).

The use of MAbs for in vitro diagnosis is well known. See, for example, Carlsson et al., *Bio/Technology* 7 (6): 567 (1989). For example, MAbs can be used to detect the presence of a tumor-associated antigen in tissue from biopsy samples. MAbs also can be used to measure the amount of tumor-associated antigen in clinical fluid samples using techniques such as radioimmunoassay, enzyme-linked immunosorbent assay, and fluorescence immunoassay.

Conjugates of tumor-targeted MAbs and toxins can be used to selectively kill cancer cells in vivo (Spalding, *Bio/Technology* 9(8): 701 (1991); Goldenberg, *Scientific American Science & Medicine* 1(1): 64 (1994)). For example, therapeutic studies in experimental animal models have demonstrated the anti-tumor activity of antibodies carrying cytotoxic radionuclides. (Goldenberg et al., *Cancer Res.* 41: 4354 (1981), Cheung et al., *J. Nat'l Cancer Inst.* 77: 739 (1986), and Senekowitsch et al., *J Nucl. Med.* 30: 531 (1989)). Also, see Stein et al., *Antibody Immunoconj. Radiopharm.* 4: 703 (1991), which is fully incorporated by reference. Moreover, Phase-I therapeutic trials with some of these MAbs have been initiated for treatment of lymphoma, melanoma, and other malignancies. See, for example, DeNardo et al., *Int. J. Cancer Suppl.* 3: 96 (1988), and Goldenberg et al., *J. Clin. Oncol.* 9: 548 (1991).

Humanized, chimeric and fully human antibodies and fragments thereof are suitable for use in therapeutic methods and diagnostic methods. Accordingly, contemplated in the present invention is a method of delivering a diagnostic or therapeutic agent, or a combination thereof, to a target comprising (i) providing a composition that comprises an anti-EGP-1 antibody and (ii) administering to a subject in need thereof the diagnostic or therapeutic antibody conjugate. Preferably, the chimeric, humanized and fully human RS7 antibodies and fragments thereof of the present invention are used in methods for treating malignancies.

Also described herein is a cancer cell targeting diagnostic or therapeutic conjugate comprising an antibody component comprising an anti-EGP-1 mAb or fragment thereof or an antibody fusion protein or fragment thereof that binds to the cancer cell, wherein the antibody component is bound to at least one diagnostic or at least one therapeutic agent. Preferably, the diagnostic conjugate comprises at least a photoactive diagnostic agent or an MRI contrast agent. Still preferred, the diagnostic agent is a radioactive label with an energy between 60 and 4,000 keV.

The compositions for treatment contain at least one naked or conjugated humanized, chimeric or human RS7 antibody alone, or in combination with other naked or conjugated humanized, chimeric, human or other antibodies of the present invention, or other naked or conjugated humanized, chimeric or human antibodies not disclosed herein. The present invention also contemplates administration of a conjugated or naked antibody with a therapeutic agent such as an immunomodulator, or diagnostic agent that is not conjugated to the anti-EGP-1 antibody. Naked or conjugated antibodies to the same or different epitope or antigen may be also combined with one or more of the antibodies of the present invention.

Accordingly, the present invention contemplates the administration anti-EGP-1 antibodies and fragments thereof alone, as a naked antibody or antibody fragment, or administered as a multimodal therapy. Preferably, the antibody is a humanized, chimeric or fully human RS7 antibody or fragment thereof. Multimodal therapies of the present invention further include immunotherapy with a naked anti-EGP-1 antibody supplemented with administration of other antibodies in the form of naked antibodies, fusion proteins, or as immunoconjugates. For example, a humanized, chimeric or fully human RS7 antibody may be combined with another naked humanized, chimeric RS7 or other antibody, or a humanized, chimeric RS7 or other antibody conjugated to an isotope, one or more chemotherapeutic agents, cytokines, toxins or a combination thereof. For example, the present invention contemplates treatment of a naked or conjugated EGP-1 or RS7 antibody or fragments thereof before, in combination with, or after other solid tumor/carcinoma associated antibodies such as anti-EGP-2, CEA, CSAp, MUC1-4, EGFR, HER2/neu, PSA, CC49 (anti-Tag 72 antibody) and PSMA antibodies. These solid tumor antibodies may be naked or conjugated to, inter alia, drugs, enzymes, hormones, toxins, isotopes, or immunomodulators. A fusion protein of a humanized, chimeric or fully human RS7 antibody and a toxin or may also be used in this invention. Many different antibody combinations may be constructed, either as naked antibodies or as partly naked and partly conjugated with a therapeutic agent or immunomodulator. Alternatively, different naked antibody combinations may be employed for administration in combination with other therapeutic agents, such as a cytotoxic drug or with radiation. Combinations of such antibodies can also be made, advantageously, with antisense oligonucleotides, as are known in the art. As such, the therapeutic conjugates may comprise an oligonucleotide, especially an antisense oligonucleotide that preferably are directed against oncogenes and oncogene products of B-cell malignancies. For example, antisense molecules inhibiting bcl-2 expression that are described in U.S. Pat. No. 5,734,033 (Reed) which is incorporated by reference in its entirety, may also be conjugated to, or form the therapeutic agent portion of an antibody fusion protein or be administered with a humanized RS7 antibody of the present invention.

The monospecific binding proteins described herein that are linked to diagnostic or therapeutic agents directly target RS7 positive tumors. The monospecific molecules bind selectively to targeted antigens and as the number of binding sites on the molecule increases, the affinity for the target cell increases and a longer residence time is observed at the desired location. Moreover, non-antigen bound molecules are cleared from the body quickly and exposure of normal tissues is minimized. A use of multispecific binding proteins is pre-targeting RS7 positive tumors for subsequent specific delivery of diagnostic or therapeutic agents. The agents are carried by histamine succinyl glycyl (HSG) containing peptides. The murine monoclonal antibody designated 679 (an IgG1, K) binds with high affinity to molecules containing the tri-peptide moiety, HSG (Morel et al., Molecular immunology, 27, 995-1000, 1990). 679 MAb can form a bispecific binding protein with hRS7 that binds with HSG and the target antigen. Alternative haptens may also be utilized. These binding proteins bind selectively to targeted antigens allowing for increased affinity and a longer residence time at the desired location. Moreover, non-antigen bound diabodies are cleared from the body quickly and exposure of normal tissues is minimized.

RS7 antibodies and fragments thereof can be used to treat mammalian disorders such as cancer. The cancer includes, but is not limited to, lung, breast, bladder, ovarian prostate and colon cancers.

Delivering a diagnostic or a therapeutic agent to a target for diagnosis or treatment in accordance with the invention includes providing the anti-EGP-1 antibody or fragments thereof with a diagnostic or therapeutic agent and administering to a subject in need thereof with the binding protein. Diagnosis further requires the step of detecting the bound proteins with known techniques.

Administration of the antibodies and their fragments of the present invention with diagnostic or therapeutic agents can be effected in a mammal by intravenous, intraarterial, intraperitoneal, intramuscular, subcutaneous, intrapleural, intrathecal, perfusion through a regional catheter, or direct intralesional injection. When administering the binding protein by injection, the administration may be by continuous infusion or by single or multiple boluses. Doses in the range of 20 to 800 mg/m$^2$ are feasible, with doses between 100 and 500 mg/m$^2$ preferably, for therapy, and commensurately lower doses recommended for diagnostic imaging, such as 0.5 mg to 100 mg/patient. Such doses may be repeated at different frequencies, depending on the clinical situation and patient tolerance.

The antibody with the diagnostic or therapeutic agent may be provided as a kit for human or mammalian therapeutic and diagnostic use in a pharmaceutically acceptable injection vehicle, preferably phosphate-buffered saline (PBS) at physiological pH and concentration. The preparation preferably will be sterile, especially if it is intended for use in humans. Optional components of such kits include stabilizers, buffers, labeling reagents, radioisotopes, paramagnetic compounds, second antibody for enhanced clearance, and conventional syringes, columns, vials and the like.

Naked Antibody Therapy

A therapeutically effective amount of the naked chimeric, humanized and fully human RS7 antibodies, or their fragments, can be formulated in a pharmaceutically acceptable excipient. The efficacy of the naked chimeric, humanized and fully human RS7 antibodies can also be enhanced by supplementing these naked antibodies with one or more other naked antibodies, with one or more immunoconjugates of chimeric, humanized and fully human RS7 antibodies conjugated to a therapeutic agent, such as a drug, toxin, immunomodulator, hormone, growth factor, enzyme or therapeutic radionuclides, or with one or more therapeutic agent, including a drug, toxin, immunomodulator, hormone, growth factor, enzyme, oligonucleotide, or therapeutic radionuclide, administered concurrently or sequentially or according to a prescribed dosing regimen, with the RS7 antibodies or fragments thereof.

In a preferred embodiment, the naked or conjugated RS7 antibodies of the present invention are combined with at least one cancer drug. Such combination therapy can improve the effect of the drug or lower drug dose that is needed. For example, the $IC_{50}$ value was determined for Dox-RS7 and 2P-Dox-RS7 on a lung cancer cell line, Calu3, and two breast cancer cell lines, MDA468 and T47D, respectively. Calu3 and T47D cells are positive for an EGP-1 antigen and negative for a CEA antigen, and MDA468 is positive for both the EGP-1 and CEA antigens. Results indicate that the $IC_{50}$ value for Dox-RS7 is 0.04 µg/ml and for 2P-Dox-RS7 is 0.023 µg/ml. Therefore, conjugating a naked, human, humanized or chimeric anti-EGP-1 antibody or fragment of the present invention to a particular drug, such as 2P-Dox may help overcome multidrug resistance. This is also possible when the antibody is given in a combination with a particular drug, as described.

RS7 Immunoconjugates

The present invention also contemplates the use of humanized, chimeric and human RS7 antibodies and fragments thereof for therapy. The objective of immunotherapy is to deliver cytotoxic doses of radioactivity, toxin, cytokine, enzyme, or hormone, or drug to target cells, while minimizing exposure to non-target tissues. The RS7 antigen binding proteins of the present invention can be used to treat a variety of tumors, such as of the lung, breast, bladder, ovary, uterus, stomach, and prostate.

Any of the antibodies or antibody fusion proteins and fragments thereof of the present invention can be conjugated with one or more therapeutic or diagnostic agents. Generally, one therapeutic or diagnostic agent is attached to each antibody or antibody fragment but more than one therapeutic agent or diagnostic agent can be attached to the same antibody or antibody fragment. If the Fc region is absent (for example when the antibody used as the antibody component of the immunoconjugate is an antibody fragment), it is possible to introduce a carbohydrate moiety into the light chain variable region of a full-length antibody or antibody fragment. See, for example, Leung et al., *J. Immunol.* 154: 5919 (1995); Hansen et al., U.S. Pat. No. 5,443,953 (1995), Leung et al., U.S. Pat. No. 6,254,868, all of which are incorporated in their entirety by reference. The engineered carbohydrate moiety is used to attach the therapeutic or diagnostic agent.

Methods for conjugating peptides to antibody components via an antibody carbohydrate moiety are well-known to those of skill in the art. See, for example, Shih et al., *Int. J. Cancer* 41: 832 (1988); Shih et al., *Int. J Cancer* 46: 1101 (1990); and Shih et al., U.S. Pat. No. 5,057,313, all of which are incorporated in their entirety by reference. The general method involves reacting an antibody component having an oxidized carbohydrate portion with a carrier polymer that has at least one free amine function and that is loaded with a plurality of peptide. This reaction results in an initial Schiff base (imine) linkage, which can be stabilized by reduction to a secondary amine to form the final conjugate. Also, a chelator such as DTPA (such as Mx-DTPA), DOTA, TETA, or NOTA can be attached to the antibody.

The antibody fusion proteins of the present invention comprise two or more antibodies or fragments thereof and each of the antibodies or fragments that compose this fission protein can contain a therapeutic agent or diagnostic agent. Additionally, one or more of the antibodies or fragments of the antibody fusion protein can have more than one therapeutic of diagnostic agent attached. Further, the therapeutic agents do not need to be the same but can be different therapeutic agents, for example, one can attach a drug and a radioisotope to the same fusion protein. Particularly, an IgG can be radiolabeled with $^{131}$I and attached to a drug. The $^{131}$I can be incorporated into the tyrosine of the IgG and the drug attached to the epsilon amino group of the IgG lysines. Both therapeutic and diagnostic agents also can be attached to reduced SH groups and to the carbohydrate side chains.

A wide variety of diagnostic and therapeutic reagents can be advantageously conjugated to the antibodies of the invention. The therapeutic agents recited here are those agents that also are useful for administration separately with the naked antibody as described above. Therapeutic agents include, for example, chemotherapeutic drugs such as vinca alkaloids, anthracyclines, epidophyllotoxinw, taxanes, antimetabolites, alkylating agents, antibiotics, substituted urea, enzymes, Cox-2 inhibitors, antimitotics, antiangiogenic and apoptotoic agents, particularly doxorubicin, doxorubicin analogs, methotrexate, taxol, CPT-11, camptothecans, and others from these and other classes of anticancer agents, methyl hydrazine derivative, adrenocortical suppressant, antagonist, endostatin, taxol, and the like. Other useful cancer chemotherapeutic drugs for the preparation of immunoconjugates and antibody fusion proteins include nitrogen mustards, ethylenimine derivatives, alkyl sulfonates, nitrosoureas, triazenes, folic acid analogs, COX-2 inhibitors, pyrimidine analogs, purine analogs, platinum coordination complexes, hormones, tyrosine kinase inhibitors, such as those that inhibit a EGF-receptor tyrosine kinase, a BCR ABL tyrosine kinase or a VEGF-receptor tyrosine kinase, and the like. Suitable chemotherapeutic agents are described in *Remington's Pharmaceutical Sciences*, 19th Ed. (Mack Publishing Co. 1995), and in *Goodman and Gilman's The Pharmacological Basis of Therapeutics*, 7th Ed. (MacMillan Publishing Co. 1985), as well as revised editions of these publications. Other suitable chemotherapeutic agents, such as experimental drugs, are known to those of skill in the art.

A toxin, such as *Pseudomonas* exotoxin, may also be complexed to or form the therapeutic agent portion of an immunoconjugate of the RS7 and hRS7 antibodies of the present invention. Other toxins suitably employed in the preparation of such conjugates or other fusion proteins, include ricin, abrin, ribonuclease (RNase), DNase I, Staphylococcal enterotoxin-A, pokeweed antiviral protein, gelonin, diphtherin toxin, *Pseudomonas* exotoxin, and *Pseudomonas* endotoxin. See, for example, Pastan et al., *Cell* 47:641 (1986), and Goldenberg, C A—*A Cancer Journal for Clinicians* 44:43 (1994). Additional toxins suitable for use in the present invention are known to those of skill in the art and are disclosed in U.S. Pat. No. 6,077,499, which is incorporated in its entirety by reference.

An immunomodulator, such as a cytokine may also be conjugated to, or form the therapeutic agent portion of the EGP-1, RS7 and hRS7 immunoconjugate, or be administered unconjugated to the chimeric, humanized or human RS7 antibodies or fragments thereof of the present invention. As used herein, the term "immunomodulator" includes cytokines, stem cell growth factors, lymphotoxins, such as tumor necrosis factor (TNF), and hematopoietic factors, such as interleukins (e.g., interleukin-1 (IL-1), IL-2, IL-3, IL-6, IL-10, IL-12, IL-18, and IL-21), colony stimulating factors (e.g., granulocyte-colony stimulating factor (G-CSF) and granulocyte macrophage-colony stimulating factor (GM-CSF)), interferons (e.g., interferons-α, -β and -γ), the stem cell growth factor designated "S 1 factor," erythropoietin and thrombopoietin, or a combination thereof. Examples of suitable immunomodulator moieties include IL-2, IL-6, IL-10, IL-12, IL-18, IL-21, interferon-γ, TNF-α, and the like. Alternatively, subjects can receive naked EGP-1 or RS7 antibodies and a separately administered cytokine, which can be administered before, concurrently or after administration of the naked RS7 antibodies. The RS7 antibody may also be conjugated to the immunomodulator. The immunomodulator may also be conjugated to a hybrid antibody consisting of one or more antibodies binding to different antigens.

A therapeutic or diagnostic agent can be attached at the hinge region of a reduced antibody component via disulfide bond formation. As an alternative, such peptides can be attached to the antibody component using a heterobifunctional cross-linker, such as N-succinyl 3-(2-pyridyldithio) proprionate (SPDP). Yu et al., *Int. J. Cancer* 56: 244 (1994). General techniques for such conjugation are well known in the art. See, for example, Wong, *Chemistry of Protein Conjugation and Cross-Linking* (CRC Press 1991); Upeslacis et al., "Modification of Antibodies by Chemical Methods," in *Monoclonal Antibodies: Principles and Applications*, Birch et al. (eds.), pages 187-230 (Wiley-Liss, Inc. 1995); Price, "Production and Characterization of Synthetic Peptide-Derived Antibodies," in *Monoclonal Antibodies: Production, Engineering and Clinical Application*, Ritter et al. (eds.), pages 60-84 (Cambridge University Press 1995). Alternatively, the therapeutic or diagnostic agent can be conjugated via a carbohydrate moiety in the Fc region of the antibody. The carbohydrate group can be used to increase the loading of the same peptide that is bound to a thiol group, or the carbohydrate moiety can be used to bind a different peptide.

Furthermore, a radiolabeled antibody, immunoconjugate, or fragments thereof may comprise a γ-emitting radioisotope or a positron-emitter useful for diagnostic imaging. Suitable radioisotopes, particularly in the energy range of 25 to 4,000 keV, include $^{131}$I, $^{123}$I, $^{124}$I, $^{86}$Y, $^{62}$Cu, $^{64}$Cu, $^{67}$Ga, $^{68}$Ga, $^{99m}$Tc, $^{94m}$Tc, $^{18}$F, $^{11}$C, $^{13}$N, $^{15}$O, $^{75}$Br, and the like. See for example, U.S. patent application entitled "Labeling Targeting Agents with Gallium-68"—Inventors G. L. Griffiths and W. J. McBride, (U.S. Provisional Application No. 60/342,104 now U.S. Pat. No. 7,011,816), which discloses positron emitters, such as $^{18}$F, $^{68}$Ga, $^{94m}$Tc and the like, for imaging purposes and which is incorporated in its entirety by reference. Preferably, the energy range for diagnostic and therapeutic radionuclides is 25-4,000_keV. Other useful radionuclides include $^{90}$Y, $^{111}$In, $^{125}$I, $^{3}$H, $^{35}$S, $^{14}$C, $^{186}$Re, $^{188}$Re, $^{189}$Re, $^{177}$Lu, $^{67}$Cu, $^{212}$Bi, $^{213}$Bi, $^{211}$At, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{94m}$Tc, $^{121m}$Te, $^{122m}$Te, $^{125m}$Te, $^{165}$Tm, $^{167}$Tm, $^{168}$Tm, $^{111}$Ag, $^{197}$Pt, $^{109}$Pd, $^{32}$P, $^{33}$P, $^{47}$Sc, $^{153}$Sm, $^{177}$Lu, $^{105}$Rh, $^{142}$Pr, $^{143}$Pr, $^{161}$Tb, $^{166}$H, $^{199}$Au, $^{57}$Co, $^{58}$Co, $^{51}$Cr, $^{59}$Fe, $^{18}$F, $^{75}$Se, $^{201}$Tl, $^{225}$Ac, 76Br, $^{86}$Y, $^{169}$Yb, $^{166}$Dy, $^{212}$Pb, and $^{223}$Ra.

For example, $^{67}$Cu, considered one of the more promising radioisotopes for radioimmunotherapy due to its 61.5 hour half-life and abundant supply of beta particles and gamma rays, can be conjugated to an RS7 antigen binding protein using the chelating agent, p-bromoacetamido-benzyl-tetraethylaminetetraacetic acid (TETA). Chase, supra. Alternatively, $^{90}$Y, which emits an energetic beta particle, can be coupled to an RS7 antigen binding protein using diethylenetriaminepentaacetic acid (DTPA). Moreover, a method for the direct radiolabeling of the RS7 MAb with $^{131}$I is described by Stein et al. (1991), supra, and the patent by Govindan et al., WO 9911294A1 entitled "Stable Radioiodine Conjugates and Methods for Their Synthesis," and is incorporated herein by reference in their entirety.

The RS7 antibodies or fragments thereof of the present invention that have a boron addend-loaded carrier for thermal neutron activation therapy will normally be effected in similar ways. However, it will be advantageous to wait until non-targeted RS7 immunoconjugate clears before neutron irradiation is performed. Clearance can be accelerated using an antibody that binds to the RS7 antibody. See U.S. Pat. No. 4,624,846 for a description of this general principle. For example, boron addends such as carboranes, can be attached to RS7 antibodies. Carboranes can be prepared with carboxyl functions on pendant side chains, as is well known in the art. Attachment of carboranes to a carrier, such as aminodextran, can be achieved by activation of the carboxyl groups of the carboranes and condensation with amines on the carrier. The intermediate conjugate is then conjugated to the RS7 antibody. After administration of the RS7 antibody conjugate, a boron addend is activated by thermal neutron irradiation and converted to radioactive atoms that decay by α-emission to produce highly toxic, short-range effects.

Furthermore, the present invention includes methods of diagnosing cancer in a subject. Diagnosis may be accomplished by administering a diagnostically effective amount of a diagnostic conjugate, formulated in a pharmaceutically suitable excipient, and detecting said label. For example, radioactive and non-radioactive agents can be used as diagnostic agents. A suitable non-radioactive diagnostic agent is a contrast agent suitable for magnetic resonance imaging, computed tomography or ultrasound. Magnetic imaging agents include, for example, non-radioactive metals, such as manganese, iron and gadolinium, complexed with metal-chelate combinations that include 2-benzyl-DTPA and its monomethyl and cyclohexyl analogs, when used along with the antibodies of the invention. See U.S. Ser. No. 09/921,290 filed on Oct. 10, 2001 (PGP No. US 2002/0041847 A1), which is incorporated in its entirety by reference.

Accordingly, a method of diagnosing a malignancy in a subject is described, comprising (i) performing an in vitro diagnosis assay on a specimen from the subject with a composition comprising a naked anti-EGP-1 MAb or fragment thereof or a naked antibody fusion protein or fragment thereof. For example, RT-PCR and immunoassay in vitro diagnosis methods can be used to detect the presence of minute amounts of EGP-1 in tissues, blood and other body fluids as a useful diagnostic/detection method. Immunohistochemistry can be used to detect the presence of EGP-1 in a cell or tissue. Preferably, the malignancy that is being diagnosed is a cancer. Most preferably, the cancer is selected from the group of lung, prostate, ovarian, breast, colon and bladder.

Additionally, a chelator such as DTPA, DOTA, TETA, or NOTA or a suitable peptide, to which a detectable label, such as a fluorescent molecule, or cytotoxic agent, such as a heavy metal or radionuclide, can be conjugated. For example, a therapeutically useful immunoconjugate can be obtained by conjugating a photoactive agent or dye to an antibody fusion protein. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy (Joni et al. (eds.), *Photodynamic Therapy of Tumors and Other Diseases* (Libreria Progetto 1985); van den Bergh, *Chem. Britain* 22:430 (1986)). Moreover, monoclonal antibodies have been coupled with photoactivated dyes for achieving phototherapy. Mew et al., *J. Immunol.* 130:1473 (1983); idem., *Cancer Res.* 45:4380 (1985); Oseroff et al., *Proc. Natl. Acad. Sci. USA* 83:8744 (1986); idem., *Photochem. Photobiol.* 46:83 (1987); Hasan et al., *Prog. Clin. Biol. Res.* 288:471 (1989); Tatsuta et al., *Lasers Surg. Med.* 9:422 (1989); Pelegrin et al., *Cancer* 67:2529 (1991). However, these earlier studies did not include use of endoscopic therapy applications, especially with the use of antibody fragments or subfragments. Thus, the present invention contemplates the therapeutic use of immunoconjugates comprising photoactive agents or dyes.

Contrast agents such as a MRI contrast agent, a paramagnetic ion and an ultrasound enhancing agent are also contemplated in the present invention. For example, gadolinium ions, lanthanum ions, manganese ions or other comparable label, CT contrast agents, and ultrasound contrast agents are suitable for use in the present invention. In a preferred embodiment, the ultrasound enhancing agent is a liposome that comprises a humanized RS7 IgG or fragment thereof. Also preferred, the liposome is gas filled.

For purposes of therapy, the RS7 antibodies and fragments thereof of the present invention are administered to a patient in a therapeutically effective amount. An antibody is said to be administered in a "therapeutically effective amount" if the amount administered is physiologically significant. An agent is physiologically significant if its presence results in a detectable change in the physiology of a recipient patient.

In Vitro Diagnosis

The present invention contemplates the use of RS7 antibodies, including RS7 and hRS7 antibodies and fragments thereof, to screen biological samples in vitro for the presence of the RS7 antigen. In such immunoassays, the RS7 antibody may be utilized in liquid phase or bound to a solid-phase carrier, as described below. Also, see Stein et al. (1993), supra, and Stein et al., *Cancer Res.* 49: 32 (1989), which is fully incorporated by reference.

One example of a screening method for determining whether a biological sample contains the RS7 antigen is the radioimmunoassay (RIA). For example, in one form of RIA, the substance under test is mixed with RS7 antigen MAb in the presence of radiolabeled RS7 antigen. In this method, the concentration of the test substance will be inversely proportional to the amount of labeled RS7 antigen bound to the MAb and directly related to the amount of free labeled RS7 antigen. Other suitable screening methods will be readily apparent to those of skill in the art.

Alternatively, in vitro assays can be performed in which an RS7 antigen binding protein is bound to a solid-phase carrier. For example, MAbs can be attached to a polymer, such as aminodextran, in order to link the MAb to an insoluble support such as a polymer-coated bead, a plate or a tube.

Other suitable in vitro assays will be readily apparent to those of skill in the art. The specific concentrations of detectably labeled RS7 antigen binding protein and RS7 antigen, the temperature and time of incubation, as well as other assay conditions maybe varied, depending on various factors including the concentration of the RS7 antigen in the sample, the nature of the sample, and the like. The binding activity of a sample of RS7 antigen binding protein may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

The presence of the RS7 antigen in a biological sample can be determined using an enzyme-linked immunosorbent assay (ELISA). In the direct competitive ELISA, a pure or semipure antigen preparation is bound to a solid support that is insoluble in the fluid or cellular extract being tested and a quantity of detectably labeled soluble antibody is added to permit detection and/or quantitation of the binary complex formed between solid-phase antigen and labeled antibody.

In contrast, a "double-determinant" ELISA, also known as a "two-site ELISA" or "sandwich assay," requires small amounts of antigen and the assay does not require extensive purification of the antigen. Thus, the double-determinant ELISA is preferred to the direct competitive ELISA for the detection of an antigen in a clinical sample. See, for example, the use of the double-determinant ELISA for quantitation of the c-myc oncoprotein in biopsy specimens. Field et al., *Oncogene* 4: 1463 (1989); Spandidos et al., *AntiCancer Res.* 9: 821 (1989).

In a double-determinant ELISA, a quantity of unlabeled MAb or antibody fragment (the "capture antibody") is bound to a solid support, the test sample is brought into contact with the capture antibody, and a quantity of detectably labeled soluble antibody (or antibody fragment) is added to permit detection and/or quantitation of the ternary complex formed between the capture antibody, antigen, and labeled antibody. An antibody fragment is a portion of an antibody such as $F(ab')_2$, $F(ab)_2$, Fab', Fab, and the like. In the present context, an antibody fragment is a portion of an RS7 MAb that binds to an epitope of the RS7 antigen. The term "antibody fragment" also includes any synthetic or genetically engineered protein that acts like an antibody by binding to a specific antigen to form a complex. For example, antibody fragments include isolated fragments consisting of the light chain variable region, "Fv" fragments consisting of the variable regions of the heavy and light chains, and recombinant single chain polypeptide molecules in which light and heavy variable regions are connected by a peptide linker. An antibody fusion protein is a polyspecific antibody composition comprising at least two substantially monospecific antibodies or antibody fragments, wherein at least two of the antibodies or antibody fragments bind to different epitopes of the RS7 antigen. An RS7 fusion protein also includes a conjugate of an antibody fusion protein with a diagnostic or therapeutic agent. The term RS7 antibody includes humanized, chimeric, human and murine antibodies, antibody fragments thereof, immunoconjugates and fragments thereof and antibody fusion proteins and fragments thereof.

Methods of performing a double-determinant ELISA are well-known. See, for example, Field et al., supra, Spandidos et al., supra, and Moore et al., "Twin-Site ELISAs for fos and myc Oncoproteins Using the AMPAK System," in *Methods in Molecular Biology*, Vol. 10, pages 273-281 (The Humana Press, Inc. 1992). For example, in one method for the detection of RS7 antigen using the double-determinant ELISA, finely minced tissue from a biopsy sample is lyophilized and resuspended in lysis buffer (100 mM NaCl, 50 mM Tris-HCl, pH 7.4) containing 1% nonidet-p40 (NP40), 0.6 µl/ml aprotinin, 0.2 mM phenyl methyl sulphonyl fluoride, 0.1 µg/ml leupeptin and 1 mM EDTA at a concentration of 10-20 mg tissue (wet weight) per 500 µl solution. The suspension is incubated for 60 minutes on ice, and then sonicated for approximately six 10-second intervals. Insoluble material is removed by centrifugation.

The soluble extract is added to microliter plate wells containing an adsorbed RS7 antigen MAb as the capture antibody. Captured RS7 antigen is then recognized by a second RS7 antigen MAb, which has been coupled with alkaline phosphatase. The amount of bound alkaline phosphatase, proportional to the amount of RS7 antigen in the extract, is detected colormetrically using a chromogenic substrate, such as p-nitrophenylphosphate.

Alternatively, a double-determinant ELISA for the RS7 antigen can be performed using horse radish peroxidase. Other variations of sample preparation and the double-determinant ELISA can be devised by those of skill in the art with routine experimentation.

In the double-determinant ELISA, the soluble antibody or antibody fragment must bind to an RS7 epitope that is distinct from the epitope recognized by the capture antibody. For example, the soluble antibody can be the RS7 MAb, while the capture antibody can be MR23. Alternatively, the soluble antibody can be MR23, while the capture antibody can be the RS7 MAb.

The double-determinant ELISA can be performed to ascertain whether the RS7 antigen is present in a biopsy sample. Alternatively, the assay can be performed to quantitate the amount of RS7 antigen that is present in a clinical sample of body fluid. The quantitative assay can be performed by including dilutions of purified RS7 antigen. A method for purifying the RS7 antigen is illustrated below.

The RS7 MAbs and fragments thereof of the present invention also are suited for the preparation of an assay kit. Such a kit may comprise a carrier means that is compartmentalized to receive in close confinement one or more container means such as vials, tubes and the like, each of said container means comprising the separate elements of the immunoassay.

For example, there may be a container means containing the capture antibody immobilized on a solid phase support, and a further container means containing detectably labeled antibodies in solution. Further container means may contain standard solutions comprising serial dilutions of RS7 antigen. The standard solutions of RS7 antigen may be used to prepare a standard curve with the concentration of RS7 antigen plotted on the abscissa and the detection signal on the ordinate. The results obtained from a sample containing RS7 antigen may be interpolated from such a plot to give the concentration of RS7 antigen in the biological sample.

RS7 antibodies and their fragments of the present invention also can be used to detect the presence of the RS7 antigen in tissue sections prepared from a histological specimen. Such in situ detection can be used to determine the presence of the RS7 antigen and to determine the distribution of the RS7 antigen in the examined tissue. In situ detection can be accomplished by applying a detectably-labeled RS7 antigen binding protein to frozen tissue sections. Studies indicate that the RS7 antigen is not preserved in paraffin-embedded sections. Stein et al. (1993), supra. General techniques of in situ detection are well known to those of ordinary skill. See, for example, Ponder, "Cell Marking Techniques and Their Application," in *Mammalian Development: A Practical Approach*, 113-38 Monk (ed.) (IRL Press 1987), and Coligan at pages 5.8.1-5.8.8. Also, see Stein et al. (1989), supra, and Stein et al. (1993), supra.

RS7 antibodies and their fragments can be detectably labeled with any appropriate detection agent, for example, a radioisotope, an enzyme, a fluorescent label, a chemiluminescent label, a bioluminescent label or a paramagnetic label. Methods of making and detecting such detectably-labeled RS7 antigen binding proteins are well-known to those of ordinary skill in the art, and are described in more detail below.

The marker moiety can be a radioisotope that is detected by such means as the use of a gamma counter or a scintillation counter or by autoradiography. In a preferred embodiment, the diagnostic conjugate is a gamma-, beta- or a positron-emitting isotope. A marker moiety in the present description refers to molecule that will generate a signal under predetermined conditions. Examples of marker moieties include radioisotopes, enzymes, fluorescent labels, chemiluminescent labels, bioluminescent labels and paramagnetic labels. As used herein, a diagnostic or therapeutic agent is a molecule or atom, which is conjugated to an antibody moiety to produce a conjugate, which is useful for diagnosis and for therapy. Examples of diagnostic or therapeutic agents include drugs, toxins, chelators, dyes, chromagens, boron compounds, and marker moieties. Isotopes that are particularly useful for the purpose of the present invention are $^3$H, $^{131}$I, $^{35}$S, $^{14}$C, and preferably $^{125}$I. Examples of other radionuclides are, for example, $^{90}$Y, $^{111}$In, $^{99m}$Tc, $^{186}$Re, $^{188}$Re, $^{177}$Lu, $^{67}$Cu, $^{212}$Bi, $^{213}$Bi, and $^{211}$At. Additional radionuclides are also available as diagnostic and therapeutic agents. Suitable diagnostic imaging isotopes are usually in the range of 25 to 4,000 keV, while suitable therapeutic radionuclides are usually in the range of 60 to 700 keV.

The RS7 antibodies and their fragments of the present invention also can be labeled with a fluorescent compound. The presence of a fluorescently-labeled MAb is determined by exposing the RS7 antigen binding protein to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine. Fluorescently-labeled RS7 antigen binding proteins are particularly useful for flow cytometry analysis.

Alternatively, RS7 antibodies and their fragments can be detectably labeled by coupling the RS7 antigen binding protein to a chemiluminescent compound. The presence of the chemiluminescent-tagged MAb is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label RS7 antibodies and fragments thereof the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, RS7 antibodies and fragments thereof can be detectably labeled by linking the RS7 antibody to an enzyme. When the RS7 antibody-enzyme conjugate is incubated in the presence of the appropriate substrate, the enzyme moiety reacts with the substrate to produce a chemical moiety, which can be detected, for example, by spectrophotometric, fluorometric or visual means. Examples of enzymes that can be used to detectably label RS7 antibody include malate dehydrogenase, staphylococcal nuclease, delta-V-steroid isomerase, yeast alcohol dehydrogenase, α-glycerophosphate dehydrogenase, triose phosphate isomerase, horseradish peroxidase, alkaline phosphatase, asparaginase, glucose oxidase, β-galactosidase, ribonuclease, urease, catalase, glucose-6-phosphate dehydrogenase, glucoamylase and acetylcholinesterase.

RS7 antibodies, fusion proteins, and fragments thereof also can be labeled with paramagnetic ions for purposes of in vivo diagnosis. Contrast agents that are particularly useful for magnetic resonance imaging comprise Gd, Mn, Dy or Fe ions. RS7 antibodies and fragments thereof can also be conjugated to ultrasound contrast/enhancing agents. For example, the ultrasound contrast agent is a liposome that comprises a humanized RS7 IgG or fragment thereof. Also preferred, the ultrasound contrast agent is a liposome that is gas filled.

In a related vein, a bispecific antibody can be conjugated to a contrast agent. For example, the bispecific antibody may comprise more than one image-enhancing agent for use in ultrasound imaging. In a preferred embodiment, the contrast agent is a liposome. Preferably, the liposome comprises a bivalent DTPA-peptide covalently attached to the outside surface of the liposome. Still preferred, the liposome is gas filled.

Those of skill in the art will know of other suitable labels that can be employed in accordance with the present invention. The binding of marker moieties to RS7 antibodies can be accomplished using standard techniques known to the art. Typical methodology in this regard is described by Kennedy et al., *Clin. Chim. Acta* 70:1 (1976), Schurs et al., *Clin. Chim. Acta* 81: 1 (1977), Shih et al., *Int'l J. Cancer* 46: 1101 (1990), Stein et al. (1990), supra, and Stein et al. (1993), supra. Also, see generally, Coligan.

The above-described in vitro and in situ detection methods may be used to assist in the diagnosis or staging of a pathological condition. For example, such methods can be used to detect tumors that express the RS7 antigen including tumors of the lung, breast, bladder, ovary, uterus, stomach, and prostate.

In Vivo Diagnosis

The present invention also contemplates the use of RS7 antibodies for in vivo diagnosis. The method of diagnostic imaging with radiolabeled MAbs is well-known. In the technique of immunoscintigraphy, for example, antibodies are labeled with a gamma-emitting radioisotope and introduced into a patient. A gamma camera is used to detect the location and distribution of gamma-emitting radioisotopes. See, for example, Srivastava (ed.), *Radiolabeled Monoclonal Antibodies for Imaging and Therapy* (Plenum Press 1988), Chase, "Medical Applications of Radioisotopes," in *Remington's Pharmaceutical Sciences*, 18th Edition, Gennaro et al. (eds.), pp. 624-652 (Mack Publishing Co., 1990), and Brown, "Clinical Use of Monoclonal Antibodies," in *Biotechnology and Pharmacy*, 227-49, Pezzuto et al. (eds.) (Chapman & Hall 1993).

For diagnostic imaging, radioisotopes may be bound to the RS7 antibody either directly, or indirectly by using an intermediary functional group. Useful intermediary functional groups include chelators such as ethylenediaminetetraacetic acid and diethylenetriaminepentaacetic acid. For example, see Shih et al., supra, and U.S. Pat. No. 5,057,313.

The radiation dose delivered to the patient is maintained at as low a level as possible through the choice of isotope for the best combination of minimum half-life, minimum retention in the body, and minimum quantity of isotope, which will permit detection and accurate measurement. Examples of radioisotopes that can be bound to RS7 antibody and are appropriate for diagnostic imaging include $^{99m}$Tc and $^{111}$In.

Pharmaceutically Suitable Excipient

Additional pharmaceutical methods may be employed to control the duration of action of an RS7 antibody in a therapeutic application. Control release preparations can be prepared through the use of polymers to complex or adsorb the RS7 antibody. For example, biocompatible polymers include matrices of poly(ethylene-co-vinyl acetate) and matrices of a polyanhydride copolymer of a stearic acid dimer and sebacic acid. Sherwood et al., *Bio/Technology* 10: 1446 (1992). The rate of release of an RS7 antibody from such a matrix depends upon the molecular weight of the RS7 antibody, the amount of RS7 antibody within the matrix, and the size of dispersed particles. Saltzman et al., *Biophys. J* 55: 163 (1989); Sherwood et al., supra. Other solid dosage forms are described in *Remington's Pharmaceutical Sciences*, 18th ed. (1990).

The humanized, chimeric and human RS7 antibodies to be delivered to a subject can consist of the antibody alone, immunoconjugate, fusion protein, or can comprise one or more pharmaceutically suitable excipients, one or more additional ingredients, or some combination of these.

The immunoconjugate, naked antibody, fusion protein, and fragments thereof of the present invention can be formulated according to known methods to prepare pharmaceutically useful compositions, whereby the immunoconjugate or naked antibody is combined in a mixture with a pharmaceutically suitable excipient Sterile phosphate-buffered saline is one example of a pharmaceutically suitable excipient. Other suitable excipients are well known to those in the art. See, for example, Ansel et al., *Pharmaceutical Dosage Forms and Drug Delivery Systems*, 5th Edition (Lea & Febiger 1990), and Gennaro (ed.), *Remington's Pharmaceutical Sciences*, 18th Edition (Mack Publishing Company 1990), and revised editions thereof.

The immunoconjugate or naked antibody of the present invention can be formulated for intravenous administration via, for example, bolus injection or continuous infusion. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the therapeutic or diagnostic conjugate or naked antibody. Control release preparations can be prepared through the use of polymers to complex or adsorb the immunoconjugate or naked antibody. For example, biocompatible polymers include matrices of poly (ethylene-co-vinyl acetate) and matrices of a polyanhydride copolymer of a stearic acid dimer and sebacic acid. Sherwood et al., *Bio/Technology* 10: 1446 (1992). The rate of release of an immunoconjugate or antibody from such a matrix depends upon the molecular weight of the immunoconjugate or antibody, the amount of immunoconjugate, antibody within the matrix, and the size of dispersed particles. Saltzman et al., *Biophys. J* 55: 163 (1989); Sherwood et al., supra. Other solid dosage forms are described in Ansel et al., *Pharmaceutical Dosage Forms and Drug Delivery*

Systems, 5th Edition (Lea & Febiger 1990), and Gennaro (ed.), Remington's Pharmaceutical Sciences, 18th Edition (Mack Publishing Company 1990), and revised editions thereof.

The immunoconjugate, antibody fusion protein, naked antibody, and fragments thereof may also be administered to a mammal subcutaneously or even by other parenteral routes. In a preferred embodiment, the anti-EGP-1 antibody or fragment thereof is administered in a dosage of 10 to 2000 milligrams protein per dose, and preferably is repeatedly administered. Moreover, the administration may be by continuous infusion or by single or multiple boluses. In general, the dosage of an administered immunoconjugate, fusion protein or naked antibody for humans will vary depending upon such factors as the patient's age, weight, height, sex, general medical condition and previous medical history. Typically, it is desirable to provide the recipient with a dosage of immunoconjugate, antibody fusion protein or naked antibody that is in the range of from about 1 mg/kg to 20 mg/kg as a single intravenous infusion, although a lower or higher dosage also may be administered as circumstances dictate. This dosage may be repeated as needed, for example, once per week for 4-10 weeks, preferably once per week for 8 weeks, and more preferably, once per week for 4 weeks. It may also be given less frequently, such as every other week for several months. The dosage may be given through various parenteral routes, with appropriate adjustment of the dose and schedule.

The RS7 antibodies of the present invention can be formulated according to known methods to prepare pharmaceutically useful compositions, whereby RS7 antibodies are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well known to those in the art. See, for example, Remington's Pharmaceutical Sciences, 18th Ed. (1990).

For purposes of therapy, the immunoconjugate, fusion protein, or naked antibody is administered to a mammal in a therapeutically effective amount. A suitable subject for the present invention is usually a human, although a non-human animal subject is also contemplated. An antibody preparation is said to be administered in a "therapeutically effective amount" if the amount administered is physiologically significant. An agent is physiologically significant if its presence results in a detectable change in the physiology of a recipient mammal.

It will be apparent to those skilled in the art that various modifications and variations can be made to the compositions and processes of this invention. Thus, it is intended that the present invention cover such modifications and variations, provided they come within the scope of the appended claims and their equivalents.

The disclosure of all publications, patents and patent applications cited above are expressly incorporated herein by reference in their entireties to the same extent as if each were incorporated by reference individually.

The examples below are illustrative of embodiments of the current invention and should not be used, in any way, to limit the scope of the claims.

Example 1. Construction of a Chimeric RS7 Antibody

Molecular Cloning of RS7 Vκ and VH Genes

Total cytoplasmic RNA and mRNA m NA was prepared from RS7-producing hybridoma cells. The genes encoding Vκ and VH sequences were cloned by RT-PCR and 5'RACE and the sequences were determined by DNA sequencing. Multiple independent clones were sequenced to eliminate possible errors resulting from the PCR reaction. Sequence analyses revealed presence of two Vκ (#1 and #23) and one VH(RS7VH) transcripts. Combining each of the putative murine Vκ with the VH, two chimeric Abs (cAbs), containing human constant region domains were generated and expressed in Sp2/0 cells by transfection. cAb-producing clones were identified by screening the cell culture supernatants of the transfected cell clones by ELISA. Positive clones were expanded and cAbs were purified from the cell culture supernatants. The Ag-binding assay showed that only the cAb composed of Vκ#23 and VH, cAb-Vκ#23, bound to microwells coated with the crude membrane fraction of ME180, a human cervical carcinoma cell (ATCC, Rockville, Md.) (FIG. 1). The cAb with the combination of Vκ#1 and VH, cAb-Vκ#1, did not show binding to the Ag-coated wells. Therefore, the immunoreactive cAb (with Vκ#23) was designated as cRS7. The cloned murine $V_H$ and the functional Vκ (#23) sequences as the final PCR products were designated as RS7Vκ (FIG. 2A, SEQ ID NO: 1) and RS7VH (FIG. 2B, SEQ ID NO: 3), respectively.

Binding Activity Assay for RS7 Abs

A competitive ELISA binding assay was used to evaluate the binding affinity of engineered cRS7. Briefly, constant amount of biotinylated murine RS7 is mixed with varying concentrations (0.01-100 μg/ml) of testing Abs (RS7 or cRS7), and added into Ag-coated microwells, and incubated at room temperature for 1 h. After washing, HRP conjugated streptavidin is added and incubated for 1 h at room temperature. The amount of HRP-conjugated streptavidin bound to the Ag-bound biotinylated RS7 was revealed by reading $OD_{490}$ after the addition of a substrate solution containing 4 mM ortho-phenylenediamine dihydrochloride and 0.04% $H_2O_2$. By this type of competitive Ag-binding assay, it was revealed that cRS7 and murine RS7 competed equally well for the binding of biotinylated murine RS7 to the antigen coated wells, thus confirmed the authenticity of the Vκ and VH sequences obtained (FIG. 1).

Example 2. Method of hRS7 Antibody Construction

Sequence Design of hRS7 V Genes

By searching the human Vκ and VH sequences in the Kabat database, the FRs of RS7 Vκ (SEQ ID NO: 2) and VH (SEQ ID NO: 4) were found to exhibit the highest degree of sequence homology to human SA-1A'c1 Vκ (SEQ ID NO: 5) and RF-TS3 VH (SEQ ID NO: 8), respectively. One exception is the FR4 of RS7VH, which showed the highest sequence homology with that of NEWM VH (SEQ ID NO: 6. Therefore human SA-1A'CL framework sequences were used as the scaffold for grafting the CDRs of RS7Vκ (FIG. 3A, SEQ ID NO: 5; SEQ ID NO: 2; SEQ ID NO: 7), and a combination of RF-TS3 and NEWM framework sequences were used for $RS7V_H$ (FIG. 4, SEQ ID NO: 11; SEQ ID NO: 12). There are a number of amino acid changes in each chain outside of the CDR regions when compared to the starting human antibody frameworks. Several amino acid residues in murine FRs that flank the putative CDRs were maintained in the reshaped hRS7 Fv based on the guideline previously established Qu, Z., Losman, M. J., Eliassen, K. C., Hansen, H. J., Goldenberg, D. M., and Leung, S. O. (1999). Humanization of Immu31, an alphafetoprotein-specific antibody. Clin. Cancer Res. 5, 3095s-3100s. These residues are S20, D60, V85, and A100 of RS7Vκ and K38, K46, A78, and F91 of RS7VH (FIG. 3A, SEQ ID NO: 5; SEQ ID NO: 2; SEQ ID NO: 7) and 3B, SEQ ID NO: 8; SEQ ID NO: 4; SEQ ID NO: 10).

Construction of hRS7 V Sequences

A modified strategy as described by Leung et al. (Leung, S. O., Shevitz, J., Pellegrini, M. C., Dion, A. S., Shih, L. B., Goldenberg, D. M., and Hansen, H. J. (1994) Chimerization of LL2, a rapidly internalizing antibody specific for B cell lymphoma. Hybridoma, 13: 469-476) was used to construct the designed VL and VH genes for hRS7 using a combination of long oligonucleotide syntheses and PCR as illustrated in FIG. 4 (SEQ ID NO: 11-12; SEQ ID NO: 13-14). For the construction of the hRS7 VH domain, two long oligonucleotides, hRS7VHA (176-mer) and hRS7VHB (168-mer) were synthesized on an automated DNA synthesizer (Applied Biosystem).

hRS7VHA (SEQ ID NO: 19) represents nt 23 to 198 of the hRS7VH domain (SEQ ID NO: 19)
5'-GGTCTGAGTT GAAGAAGCCT GGGGCCTCAG TGAAGGTTTC

CTGCAAGGCT TCTGGATACA CCTTCACAAA CTATGGAATG

AACTGGGTGA AGCAGGCCCC TGGACAAGGG CTTAAATGGA

TGGGCTGGAT AAACACCTAC ACTGGAGAGC CAACATATAC

TGATGACTTC AAGGGA-3' hRS7VHB (SEQ ID NO: 20) represents the minus strand of the hRS7VH domain complementary to nt 174 to 340.

(SEQ ID NO: 20)
5'-ACCCTTGGCC CCAGACATCG AAGTACCAGT AGCTACTACC

GAACCCCCCT CTTGCACAGA AATACACGGC AGTGTCGTCA

GCCTTTAGGC TGCTGATCTG GAGATATGCC GTGCTGACAG

AGGTGTCCAA GGAGAAGGCA AACCGTCCCT TGAAGTCATC

AGTATATG-3'

The 3'-terminal sequences (23 nt residues) of hRS7VHA and B are complementary to each other. Under defined PCR condition, 3'-ends of hRS7VHA and B anneal to form a short double stranded DNA flanked by the rest of the long oligonucleotides. Each annealed end serves as a primer for the transcription of the single stranded DNA, resulting in a double strand DNA composed of the nt 23 to 340 of hRS7VH. This DNA was further amplified in the presence of two short oligonucleotides, hRS7VHBACK (SEQ ID NO: 21) and hRS7VHFOR (SEQ ID NO: 22) to form the full-length hRS7VH.

hRS7VHBACK
(SEQ ID NO: 21)
5'-GTGGTGCTGC AGCAATCTGG GTCTGAGTTG AAGAAGCC-3' hRS7VHFOR
(SEQ ID NO: 22)
5'-TGAGGAGACG GTGACCAGGG ACCCTTGGCC CCAGACAT-3'

Minimum amount of hRS7VHA and B (determined empirically) was amplified in the presence of 10 μl of 10×PCR Buffer (500 mM KCl, 100 mM Tris.HCL buffer, pH 8.3, 15 mM MgCl$_2$), 2 μmol of hRS7VHBACK and hRS7VHFOR, and 2.5 units of Taq DNA polymerase (Perkin Elmer Cetus, Norwalk, Conn.). This reaction mixture was subjected to 3 cycle of PCR reaction consisting of denaturation at 94° C. for 1 minute, annealing at 45° C. for 1 minute, and polymerization at 72° C. for 1.5 minutes, and followed by 27 cycles of PCR reaction consisting of denaturation at 94° C. for 1 minute, annealing at 55° C. for 1 minute, and polymerization at 72° C. for 1 minute. Double-stranded PCR-amplified product for hRS7VH was gel-purified, restriction-digested with PstI and BstEII and cloned into the complementary PstJBstEII sites of the heavy chain staging vector, VHpBS2.

For constructing the full length DNA of the humanized Vκ sequence, hRS7VKA (156-mer) and hRS7VKB (155-mer) were synthesized as described above. hRS7VKA and B were amplified by two short oligonucleotides hRS7VKBACK and hRS7VKFOR as described above.

HRS7VKA (SEQ ID NO: 23) represents nt 20 to 175 of the hRS7Vκ domain.

(SEQ ID NO: 23)
5'-CTCCATCCTC CCTGTCTGCA TCTGTAGGAG ACAGAGTCAG

CATCACCTGC AAGGCCAGTC AGGATGTGAG TATTGCTGTA

GCCTGGTATC AGCAGAAACC AGGGAAAGCC CCTAAGCTCC

TGATCTACTC GGCATCCTAC CGGTACACTG GAGTCC-3' hRS7VKB (SEQ ID NO: 24) represents the minus strand of the hRS7Vκ domain complementary to nt 155 to 320.

(SEQ ID NO: 24)
5'-CCTTGGTCCC AGCACCGAAC GTGAGCGGAG TAATATAATG

TTGCTGACAG TAATAAACTG CAAAATCTTC AGGTTGCAGA

CTGCTGATGG TGAGAGTGAA ATCTGTCCCA GATCCACTGC

CACTGAACCT ATCAGGGACT CCAGTGTACC GGTAG-3' hRS7VKBACK
(SEQ ID NO: 25)
5'-GACATTCAGC TGACCCAGTC TCCATCCTCC CTGTCTG-3' hRS7VKFOR
(SEQ ID NO: 26)
5'-ACGTTAGATC TCCACCTTGG TCCCAGCACC G-3'

Gel-purified PCR products for hRS7Vκ were restriction-digested with PvuII and BglIII and cloned into the complementary PvuI/BcII sites of the light chain staging vector, VKpBR2. The final expression vector hRS7pdHL2 was constructed by sequentially subcloning the XbaI-BamHI and XhoI/BamHI fragments of hRS7Vκ and VH, respectively, into pdHL2 as described above. The full-length cDNA and the encoded amino acid sequences of the light and heavy chains of hRS7 are disclosed in FIG. 5A (SEQ ID NO: 15; SEQ ID NO: 16) and 5B (SEQ ID NO: 17; SEQ ID NO: 18), respectively.

Transfection and Expression of hRS7 Antibodies

Approximately 30 μg of the expression vectors for hRS7 were linearized by digestion with SalI and transfected into Sp2/0-Ag14 cells by electroporation (450V and 25° F.). The transfected cells were plated into 96-well plates for 2 days and then selected for drug-resistance by adding MTX into the medium at a final concentration of 0.025 μM. MTX-resistant colonies emerged in the wells 2-3 weeks. Supernatants from colonies surviving selection were screened for human Ab secretion by ELISA assay. Briefly, 100 μl supernatants were added into the wells of a microliter plate precoated with GAH-IgG, F(ab')2 fragment-specific Ab and incubated for 1 h at room temperature. Unbound proteins were removed by washing three times with wash buffer (PBS containing 0.05% polysorbate 20). HRP-conjugated GAH-IgG, Fc fragment-specific Ab was added to the wells. Following an incubation of 1 h, the plate was washed. The bound HRP-conjugated Ab was revealed by reading A490 nm after the addition of a substrate solution containing 4 mM OPD and 0.04% $H_2O_2$. Positive cell clones were expanded and hRS7 IgG were purified from cell culture supernatant by affinity chromatography on a Protein A column.

Binding Activity of the humanized RS7 Antibody

Figure 6:
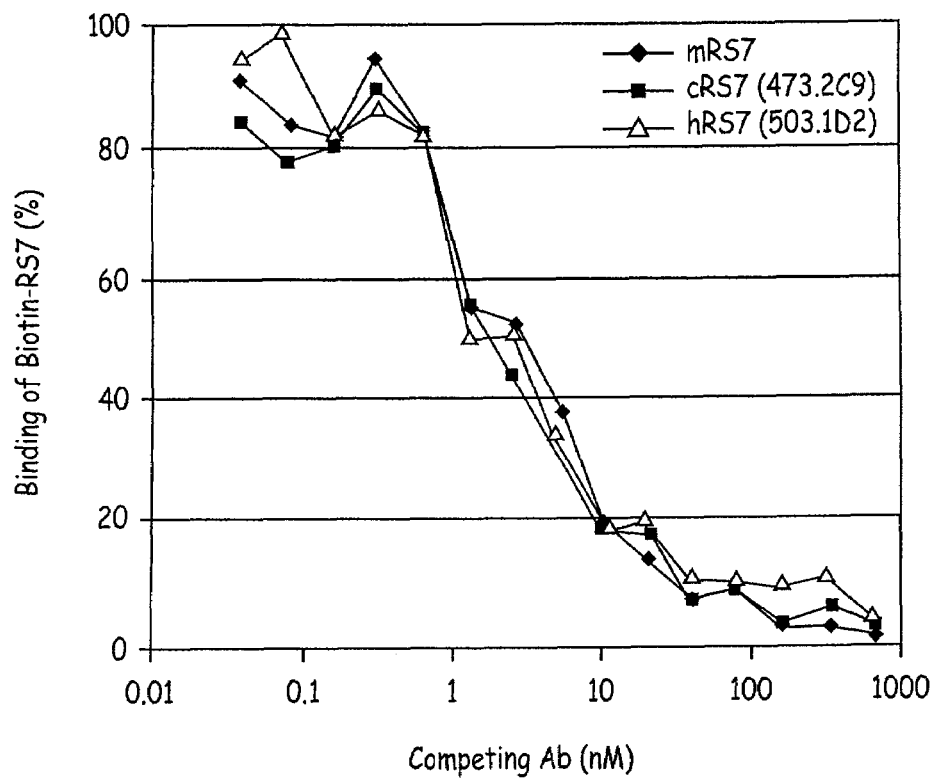
FIG. 6 shows a comparison of mRS7, cRS7, and hRS7 in competitive binding assays. Varying concentrations of competing Abs were used to compete with the binding of a constant amount of Biotinylated RS7 to the Ag coated in 96-well ELISA plates. hRS7 showed comparable blocking activity as that of RS7 and cRS7.

An ELISA competitive binding assay using ME180 cell membrane extract coated plate was used to assess the immunoreactivity of hRS7 as described (Stein et al., Int. J. Cancer 55:938-946 (1993)). ME180 cell membrane fraction was prepared by sonication and centrifugation. The crude membrane extract was coated in 96-well flat bottomed PVC plate by centrifugation and fixed with 0.1% glutaraldehyde. Constant amount of the biotinylated murine RS7 mixed with varying concentrations of mRS7, cRS7 or hRS7 was added to the membrane coated wells and incubated at room temperature for 1-2 h. After washing, HRP-conjugated streptavidin was added and incubated for 1 h at room temperature. The amount of HRP-conjugated streptavidin bound to the membrane-bound biotinylated mRS7 was revealed by reading $A_{490\ nm}$ after the addition of a substrate solution containing 4 mM orthophenylenediamine dihydrochloride and 0.04% $H_2O_2$. As shown by the competition assays in FIG. 6, hRS7 IgG exhibited comparable binding activities with that of mRS7 and cRS7, confirming the binding affinity of RS7 was preserved in humanization.

Example 3. Radioiodinations of Humanized RS7 Using Residualizing Labels

The residualizing moiety (IMP-R4, IMP-R5 or IMP-R8) was radioiodinated, and coupled to disulfide-reduced hRS7 along the procedure described elsewhere (Govindan S V, et al., *Bioconjugate Chem.* 1999; 10:231-240). See FIG. 7. In residualizing radioiodine labelings using $^{125}I$, to prepare $^{125}I$-IMP-Rx-hRS7 where x=4, 5 or 8), overall yields and specific activities (in parentheses) of 87.1% (3.38 mCi/mg), 34.3% (0.97 mCi/mg), and 76.6% (2.93 mCi/mg) were obtained using IMP-R4, IMP-R5 and IMP-R8, respectively. In large-scale $^{131}I$, labelings using $^{131}I$-IMP-R4 entity, the following results were obtained. Using 20.4 mCi of $^{131}I$, 35.7 nmol of IMP-R4 and 3.22 mg of DTT-reduced hRS7, a 60% overall yield (3.80 mCi/mg) was obtained. A different run using 30.3 mCi of $^{131}I$, IMP-R4 and reduced hRS7 produced 69.7% yield (3.88 mCi/mg). A third run using 13.97 mCi of $^{131}I$ gave 71.8% incorporation (4.42 mCi/mg). A $^{131}I$-IMP-R4 labeling using 13.6 mCi of $^{131}I$ and a non-specific humanized antibody, hLL2, resulted in 64.4% yield (3.67 mCi/mg).

Example 4. Preclinical Experiments in Breast Cancer Animal Model

For tumor targeting studies, tumors were propagated in 5-8 week old female nude mice by subcutaneous injection of $\sim$.2.3×10$^7$ cultured MDA-MB-468 cells, and the animals were used after one month when the tumor size reached $\sim$01-to-0.2 cm$^3$. The mice were injected i.v. with a mixture of $\sim$10 μCi of $^{125}I$-[IMP-Rx]-hRS7 where x=4, 5 or 8, and 20-25 μCi of $^{131}I$-MAb (CT method). Thus, each experiment was a paired-label experiment with $^{125}I/^{113}I$. At the indicated times, biodistributions in various organs and blood were determined, and expressed as % injected dose per gram. Corrections for backscatter of $^{131}I$ into $^{125}I$ window were made in determining $^{125}I$ biodistributions.

For therapy studies, tumor growth patterns under various formats were studied to determine the optimal method for steady growth of tumor. It was concluded that the method used for targeting experiments was optimal after about 8-weeks of tumor growth, and 30-50% of the animals could be used based on the tumor growth profiles. For therapy studies, the tumor-bearing animals were injected i.v. with $^{131}I$-IMPR4-hRS7 was the agent examined, and compared with directly radioiodinated material, $^{131}I$-hRS7. Baseline body weights were compared with weekly measurements of body weights and tumor volumes. Animals were sacrificed when tumors reached 3 cm$^3$. All animal experiments were carried out in accord with IACUC-approved protocols.

In Vivo Animal Biodistributions

These experiments were carried out using dual-labeled hRS7 preparations ($^{125}I$-IMP-Rx-hRS7 where x=4, 5 or 8, with each agent mixed with direct label $^{131}I$-hRS7) in the tumors grown in NIH Swiss nude mice. Tables IA, 1B and 1C describe detailed biodistributions showing the superior performance using the residualizing labels. For instance, % injected dose per gram of tumor on day-7 were 41.6±3.0%, 32.2±11.6% and 24.7±8.5% for $^{125}I$-IMP-R4-hRS7, $^{125}I$-IMP-R5-hRS7 and $^{125}I$-IMP-R8-hRS7, respectively, while that for directly labeled $^{131}I$-hRS7 at the same time-point in each of the dual-labeled experiments were 5.9±0.9%, 6.2±2.1% and 6.7±2.3%. Tumor-to-nontumor ratios for the same time-point were 1.7-to-7.6-fold higher with $^{125}I$-IMP-R4-hRS7, 1.7-to-6.0-fold higher with $^{125}I$-IMP-R5-S7, and 2.0-to-4.8-fold higher with $^{125}I$-MP-R8-S7 compared to the ratios with $^{131}I$-hRS7 (data not shown).

TABLE 1

Biodistributions of humanized RS7, dual-labeled with $^{125}I$-IMP-R (R4 or R5 or R8) and $^{131}I$-hRS7 CT method in NIH Swiss nude mice bearing MDA-MB-468 tumor xenografts Table 1A: $^{125}I$-IMP-R4-hRS7 versus $^{131}I$-hRS7 (CT)

| | | % ID/g ± SD$^1$, n = 5 | | | |
|---|---|---|---|---|---|
| Tissue | Label | 24 h | 72 h | 168 h, n = 4 | 336 h |
| MDA-MB-468 | $^{125}I$-IMP-R4 | 32.8 ± 6.3 | 46.8 ± 11.0 | 41.6 ± 3.0 | 25.1 ± 3.8 |
| | $^{131}I$ (CT) | 8.6 ± 1.5 | 8.6 ± 2.3 | 5.9 ± 0.9 | 4.4 ± 0.8 |
| | Tumor wt. | (0.19 ± 0.06) | (0.19 ± 0.08) | (0.13 ± 0.07) | (0.18 ± 0.04) |

TABLE 1-continued

Biodistributions of humanized RS7, dual-labeled with $^{125}$I-IMP-R
(R4 or R5 or R8) and $^{131}$I-hRS7 CT method in NIH Swiss nude mice
bearing MDA-MB-468 tumor xenografts

| Tissue | Label | | | | |
|---|---|---|---|---|---|
| Liver | $^{125}$I-IMP-R4 | 5.7 ± 0.7 | 4.7 ± 1.5 | 2.8 ± 0.4 | 1.3 ± 0.2 |
|  | $^{131}$I (CT) | 4.1 ± 0.3 | 2.01 ± 0.1 | 1.5 ± 0.2 | 0.7 ± 0.1 |
| Spleen | $^{125}$I-IMP-R4 | 3.6 ± 0.6 | 3.3 ± 0.6 | 2.6 ± 0.8 | 1.9 ± 0.2 |
|  | $^{131}$I (CT) | 2.6 ± 0.5 | 1.7 ± 0.4 | 1.1 ± 0.4 | 0.6 ± 0.1 |
| Kidney | $^{125}$I-IMP-R4 | 7.8 ± 0.7 | 6.8 ± 0.4 | 5.6 ± 0.8 | 3.0 ± 0.5 |
|  | $^{131}$I (CT) | 3.5 ± 0.3 | 2.1 ± 0.3 | 1.4 ± 0.3 | 0.7 ± 0.1 |
| Lungs | $^{125}$I-IMP-R4 | 4.5 ± 1.0 | 3.2 ± 0.6 | 2.2 ± 0.7 | 0.8 ± 0.2 |
|  | $^{131}$I (CT) | 3.1 ± 0.8 | 2.2 ± 0.4 | 1.6 ± 0.6 | 0.6 ± 0.2 |
| Blood | $^{125}$I-IMP-R4 | 15.1 ± 1.4 | 9.5 ± 0.7 | 6.0 ± 1.5 | 1.9 ± 0.6 |
|  | $^{131}$I (CT) | 10.8 ± 1.0 | 7.3 ± 0.6 | 5.3 ± 1.2 | 2.2 ± 0.6 |
| Stomach | $^{125}$I-IMP-R4 | 1.3 ± 0.2 | 0.6 ± 0.1 | 0.4 ± 0.1 | 0.2 ± 0.1 |
|  | $^{131}$I (CT) | 1.6 ± 0.5 | 0.7 ± 0.1 | 0.4 ± 0.1 | 0.2 ± 0.1 |
| Sm. Int. | $^{125}$I-IMP-R4 | 1.5 ± 0.2 | 0.9 ± 0.1 | 0.6 ± 0.2 | 0.2 +± 0.1 |
|  | $^{131}$I (CT) | 1.0 ± 0.1 | 0.6 ± 0.1 | 0.4 ± 0.1 | 0.2 ± 0.04 |
| Lg. Int. | $^{125}$I-IMP-R4 | 1.3 ± 0.3 | 1.0 ± 0.1 | 0.8 ± 0.1 | 0.3 ± 0.1 |
|  | $^{131}$I (CT) | 0.8 ± 0.2 | 0.5 ± 0.1 | 0.5 ± 0.1 | 0.2 ± 0.03 |
| Muscle | $^{125}$I-IMP-R4 | 1.2 ± 0.2 | 0.7 ± 0.1 | 0.5 ± 0.1 | 0.3 ± 0.2 |
|  | $^{131}$I (CT) | 0.9 ± 0.1 | 0.5 ± 0.05 | 0.3 ± 0.1 | 0.2 ± 0.1 |
| Bone | $^{125}$I-IMP-R4 | 2.3 ± 0.3 | 2.1 ± 0.3 | 2.4 ± 0.6 | 2.3 ± 1.2 |
|  | $^{131}$I (CT) | 1.4 ± 0.1 | 0.8 ± 0.1 | 0.5 ± 0.1 | 0.3 ± 0.1 |

Table 1B: $^{125}$I-IMP-R5-hRS7 versus $^{131}$I-hRS7 (CT method)

| | | % ID/g ± SD$^1$, n = 5 | | | |
|---|---|---|---|---|---|
| Tissue | Label | 24 h | 72 h | 168 h | 336 h, n = 4 |
| MDA-MB-468 | $^{125}$I-IMP-R5 | 29.1 ± 4.6 | 39.6 ± 2.7 | 32.2 ± 11.6 | 17.8 ± 7.0 |
|  | $^{131}$I (CT) | 9.2 ± 1.0 | 9.1 ± 0.6 | 6.2 ± 2.1 | 4.9 ± 2.0 |
|  | Tumor wt. | (0.14 ± 0.02) | (0.20 ± 0.05) | (0.11 ± 0.03) | (0.13 ± 0.06) |
| Liver | $^{125}$I-IMP-R5 | 4.8 ± 1.4 | 2.5 ± 0.1 | 1.8 ± 0.3 | 0.8 ± 0.3 |
|  | $^{131}$I (CT) | 5.1 ± 1.5 | 2.4 ± 0.2 | 1.7 ± 0.2 | 0.8 ± 0.3 |
| Spleen | $^{125}$I-IMP-R5 | 4.1 ± 1.0 | 2.0 ± 0.4 | 1.9 ± 0.4 | 0.8 ± 0.4 |
|  | $^{131}$I (CT) | 3.8 ± 1.2 | 1.7 ± 0.5 | 1.3 ± 0.3 | 0.7 ± 0.4 |
| Kidney | $^{125}$I-IMP-R5 | 10.0 ± 1.4 | 6.3 ± 0.5 | 5.0 ± 0.5 | 1.1 ± 0.3 |
|  | $^{131}$I (CT) | 3.7 ± 0.5 | 1.9 ± 0.3 | 1.7 ± 0.3 | 0.8 ± 0.2 |
| Lungs | $^{125}$I-IMP-R5 | 5.4 ± 1.8 | 3.2 ± 0.8 | 2.3 ± 0.2 | 0.9 ± 0.4 |
|  | $^{131}$I (CT) | 3.9 ± 1.2 | 2.5 ± 0.7 | 2.0 ± 0.3 | 0.9 ± 0.5 |
| Blood | $^{125}$I-IMP-R5 | 16.5 ± 4.0 | 8.8 ± 0.6 | 6.5 ± 1.0 | 2.7 ± 1.4 |
|  | $^{131}$I (CT) | 12.2 ± 3.0 | 7.8 ± 0.5 | 6.3 ± 0.8 | 3.1 ± 1.4 |
| Stomach | $^{125}$I-IMP-R5 | 0.9 ± 0.2 | 0.5 ± 0.1 | 0.4 ± 0.1 | 0.2 ± 0.1 |
|  | $^{131}$I (CT) | 1.1 ± 0.1 | 0.6 ± 0.1 | 0.5 ± 0.1 | 0.2 ± 0.1 |
| Sm. Int. | $^{125}$I-IMP-R5 | 1.5 ± 0.3 | 0.8 ± 0.04 | 0.6 ± 0.1 | 0.2 ± 0.1 |
|  | $^{131}$I (CT) | 1.1 ± 0.2 | 0.6 ± 0.02 | 0.5 ± 0.1 | 0.3 ± 0.1 |
| Lg. Int. | $^{125}$I-IMP-R5 | 1.4 ± 0.2 | 0.9 ± 0.1 | 0.6 ± 0.1 | 0.2 ± 0.04 |
|  | $^{131}$I (CT) | 0.7 ± 0.1 | 1.4 ± 0.03 | 0.4 ± 0.1 | 0.2 ± 0.04 |
| Muscle | $^{125}$I-IMP-R5 | 1.3 ± 0.3 | 0.7 ± 0.2 | 0.5 ± 0.1 | 0.2 ± 0.1 |
|  | $^{131}$I(CT) | 0.9 ± 0.2 | 0.6 ± 0.2 | 0.4 ± 0.1 | 0.2 ± 0.1 |
| Bone | $^{125}$I-IMP-R5 | 2.2 ± 0.6 | 1.3 ± 0.2 | 1.2 ± 0.5 | 1.0 ± 0.6 |
|  | $^{131}$I (CT) | 1.9 ± 0.7 | 0.9 ± 0.1 | 0.6 ± 0.2 | 0.3 ± 0.2 |

Table 1C: $^{125}$I-IMP-R8-hRS7 versus $^{131}$I-hRS7 (CT method)

| | | % ID/g ± SD$^1$, n = 5 | | | |
|---|---|---|---|---|---|
| Tissue | Label | 24 h | 72 h | 168 h | 336 h |
| MDA-MB-468 | $^{125}$I-IMP-R8 | 29.1 ± 5.4 | 29.6 ± 3.9 | 24.7 ± 8.5 | 11.0 ± 6.4 |
|  | $^{131}$I (CT) | 8.8 ± 1.6 | 8.8 ± 1.0 | 6.7 ± 2.3 | 2.4 ± 1.3 |
|  | Tumor wt. | (0.17 ± 0.04) | (0.12 ± 0.05) | (0.10 ± 0.04) | (0.15 ± 0.05) |
| Liver | $^{125}$I-IMP-R8 | 4.6 ± 0.7 | 3.3 ± 0.4 | 1.8 ± 0.2 | 0.7 ± 0.2 |
|  | $^{131}$I (CT) | 4.1 ± 0.6 | 3.3 ± 0.4 | 1.8 ± 0.2 | 0.8 ± 0.2 |
| Spleen | $^{125}$I-IMP-R8 | 2.6 ± 0.7 | 2.3 ± 0.2 | 1.9 ± 0.2 | 1.0 ± 0.1 |
|  | $^{131}$I (CT) | 2.4 ± 0.8 | 2.2 ± 0.3 | 2.0 ± 0.3 | 0.7 ± 0.2 |
| Kidney | $^{125}$I-IMP-R8 | 7.2 ± 0.8 | 4.6 ± 0.8 | 2.6 ± 1.0 | 1.8 ± 0.1 |
|  | $^{131}$I (CT) | 2.5 ± 0.3 | 3.0 ± 0.7 | 1.8 ± 0.5 | 0.8 ± 0.3 |
| Lungs | $^{125}$I-IMP-R8 | 3.0 ± 0.7 | 4.7 ± 0.5 | 2.3 ± 0.6 | 1.0 ± 0.4 |
|  | $^{131}$I (CT) | 2.4 ± 0.4 | 4.4 ± 0.5 | 2.1 ± 0.5 | 1.0 ± 0.4 |
| Blood | $^{125}$I-IMP-R8 | 10.8 ± 1.2 | 9.6 ± 0.9 | 6.3 ± 1.4 | 2.2 ± 0.6 |
|  | $^{131}$I (CT) | 9.2 ± 1.6 | 9.5 ± 0.8 | 6.4 ± 1.4 | 2.6 ± 0.6 |
| Stomach | $^{125}$I-IMP-R8 | 0.9 ± 0.2 | 0.7 ± 0.2 | 0.3 ± 0.1 | 0.2 ± 0.1 |
|  | $^{131}$I (CT) | 1.1 ± 0.2 | 0.9 ± 0.3 | 0.4 ± 0.1 | 0.3 ± 0.1 |
| Sm. Int. | $^{125}$I-IMP-R8 | 1.0 ± 0.1 | 0.8 ± 0.2 | 0.5 ± 0.1 | 0.2 ± 0.1 |
|  | $^{131}$I (CT) | 0.8 ± 0.1 | 0.8 ± 0.1 | 0.5 ± 0.1 | 0.2 ± 0.1 |
| Lg. Int. | $^{125}$I-IMP-R8 | 1.0 ± 0.1 | 0.9 ± 0.1 | 0.5 ± 0.1 | 0.3 ± 0.1 |
|  | $^{131}$I (CT) | 0.6 ± 0.1 | 0.6 ± 0.1 | 0.4 ± 0.1 | 0.2 ± 0.1 |

TABLE 1-continued

Biodistributions of humanized RS7, dual-labeled with $^{125}$I-IMP-R
(R4 or R5 or R8) and $^{131}$I-hRS7 CT method in NIH Swiss nude mice
bearing MDA-MB-468 tumor xenografts

| | | | | | |
|---|---|---|---|---|---|
| Muscle | $^{125}$I-IMP-R8 | 0.8 ± 0.1 | 0.6 ± 0.1 | 0.4 ± 0.1 | 0.2 ± 0.1 |
| | $^{131}$I(CT) | 0.6 ± 0.04 | 0.6 ± 0.1 | 0.4 ± 0.1 | 0.2 ± 0.1 |
| Bone | $^{125}$I-IMP-R8 | 1.4 ± 0.2 | 1.2 ± 0.3 | 1.4 ± 0.2 | 0.8 ± 0.2 |
| | $^{131}$I (CT) | 1.1 ± 0.2 | 0.9 ± 0.2 | 0.7 ± 0.1 | 0.3 ± 0.1 |

Figure 8:
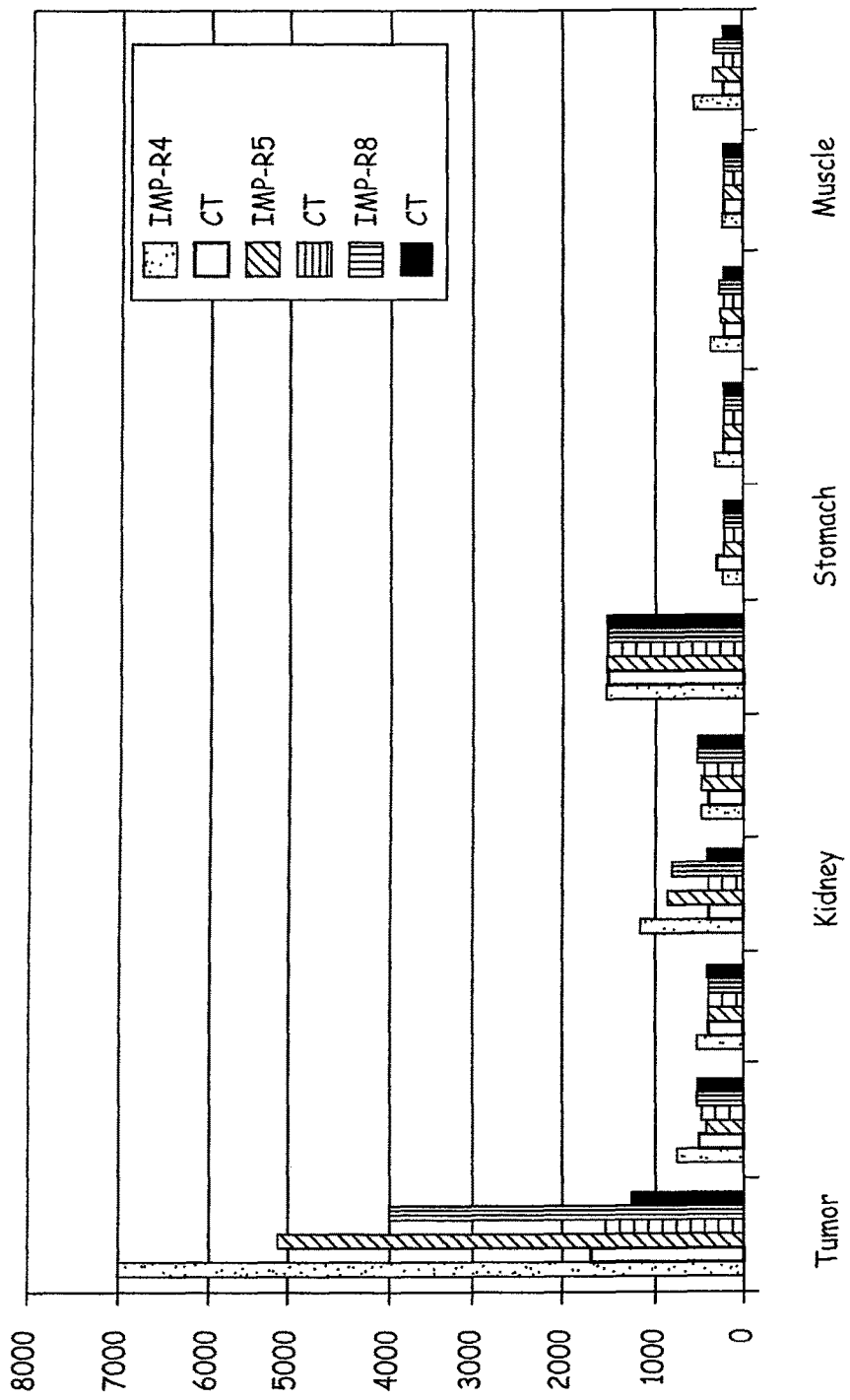
FIG. 8 is a bar graph of dosimetry due to radioiodinated hRS7 in the MDA-MB-468 tumor model.
Figure 9A:
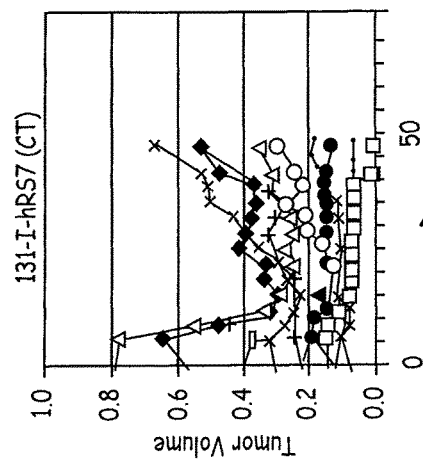
FIGS. 9A-9C show tumor growth controls, as plots of tumor volumes (cm$^3$) in Y-axis versus days post-treatment in X-axis, in individual NIH Swiss nude mice (female) subcutaneously carrying MDA-MB-468 human breast carcinoma xenografts, and which were either treated with 0.2 mCi of conventionally $^{131}$I-radioiodinated hRS7, $^{131}$I-hRS7 (FIG. 9C), or treated with 0.175 mCi of hRS7 antibody radioiodinated with $^{131}$I-IMP-R4 which is a residualizing form of $^{131}$I, $^{131}$I-IMP-R4-hR4S7 (FIG. 9B), or were untreated (FIG. 9A). Each line in each of these graphs corresponds to tumor growth in a single mouse.
Figure 9B:
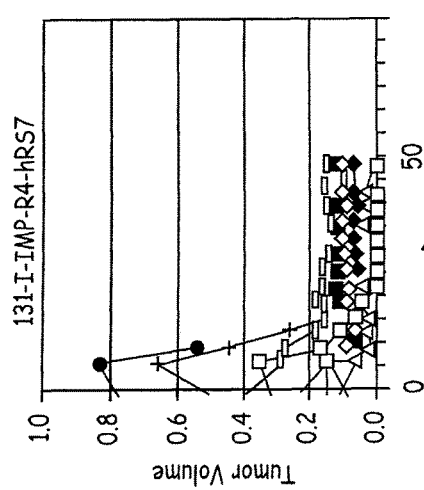
Figure 9D:
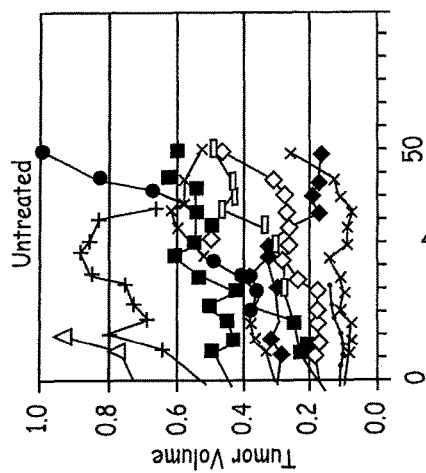
FIG. 9D is a composite of the tumor growth controls in the different groups, and represents mean tumor volumes, as a function of time in days, in animals that were treated with 0.175 mCi of $^{131}$I-IMP-R4-hRS7 (solid square) or were treated with 0.2 mCi of $^{131}$I-hRS7 (open triangle) or were untreated (solid diamond). Error bar represents standard deviation.
Figure 9C:
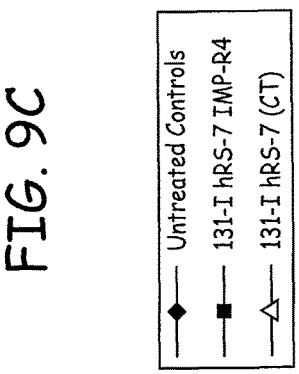
Figure 9E:
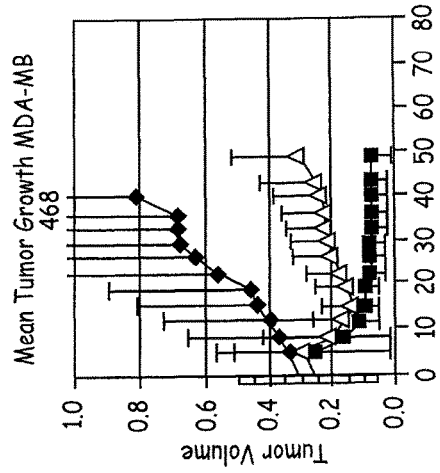
FIG. 9E is a different representation of tumor growth control vs. time plots, showing mean relative tumor volumes as a function of time in various groups with mean tumor volume at the start of therapy taken as 100. Otherwise, the legend is the same as for 9D. Error bar represents standard deviation.

Dosimetry calculations, based on biodistributions using $^{125}$I in place of $^{131}$I, were performed using the method of Siegel, J A and Stabin, M G (*Journal of Nuclear Medicine*, 1994; 35:152-156). Table-2 compares sets of residualizing and conventional radioiodine labels, and FIG. 8 describes the data graphically. All of the residualizing agents are seen to perform optimally in terms of dose delivered to tumor and tumor-to-nontumor ratios; $^{131}$I-IMP-R4-hRS7 was chosen for therapy experiments in view of the advantageous radiochemical yields and specific activities obtainable for the same agent.

TABLE 2

Calculated radiation doses due to variously
radioiodinated hRS7
in the MDA-MB-468 tumor model

| | | cGy normalized to 1500 cGy to Blood | | | | | |
|---|---|---|---|---|---|---|---|
| | | Group I | | Group II | | Group III | |
| Organ | Model | IMP-R4 | CT | IMP-R5 | CT | IMP-R8 | CT |
| Tumor | (Trap 0 point 0) | 6995 | 1613 | 5187 | 1506 | 4000 | 1206 |
| Liver | Exp | 674 | 456 | 398 | 449 | 497 | 505 |
| Spleen | Exp | 535 | 315 | 336 | 313 | 384 | 356 |
| Kidney | Exp | 1063 | 402 | 867 | 361 | 761 | 394 |
| Lungs | Exp | 450 | 392 | 450 | 422 | 506 | 473 |
| Blood(or g) | Exp | 1500 | 1500 | 1500 | 1500 | 1500 | 1500 |
| Stomach | Exp | 104 | 144 | 84 | 118 | 101 | 128 |
| Sm Int | Exp | 148 | 124 | 131 | 119 | 130 | 121 |
| Lg Int | Exp | 163 | 108 | 136 | 86 | 140 | 97 |
| Muscle | Exp | 112 | 99 | 105 | 100 | 97 | 93 |
| Bone | Exp | 486 | 151 | 244 | 149 | 245 | 151 |
| mCi for 1500 cGy to blood | | 0.231 | 0.285 | 0.213 | 0.239 | 0.248 | 0.255 |

Therapy of MDA-MB-468 Human Breast Carcinoma Xenografts in Nude Mice

Maximum-tolerated-dose (MTD): From dosimetry data (Table-2, group-1), the mCi amounts of $^{131}$I-IMP-R4-hRS7 and $^{131}$I-hRS7, producing a radiation dose of 1500 cGy to blood (estimated MTD) were calculated to be 0.231 mCi and 0.285 mCi, respectively. Experimental determination of MTD was carried out using increasing doses of each agent in Swiss nude mice. For $^{131}$I-IMP-R4-hRS7, groups of animals were administered 200, 225, 250, 275, 300 and 325 µCi; 1 out of five animals in the 250 µCi dose group died by week 4, while 3 out of 4 animals in the 300 µCi dose group died between weeks 2 and 4. Although the survival of animals in the 275 and 325 µCi dose groups at five weeks was unexpected, we concluded that the MTD was between 231 µCi (calculated from dosimetry data) and 250 µCi of administered dose. For the $^{131}$I-hRS7 ('CT'-based radioiodination), groups of animals were injected with 250, 280, 310, 340, 370 and 400 µCi; between weeks 2 and 3, six out of six animals of 340 µCi dose group, three out of six animals of 370 µCi dose group, and four out of four animals of 400 µCi dose group died. Based on these, the MTD was projected to be in the 280-310 µCi range.

Therapy Study-1

For this first therapy experiment, comparing the efficacy of $^{131}$I-IMPR-4-hRS7 with that of $^{131}$I-hRS7 (CT method), each agent used at ~70% of its maximum-tolerated dose. A single dose of 175 µCi of the residualizing agent is seen to be significantly more effective than 200 µCi of conventional radioiodine agent. In this experiment, which also included untreated controls, 10 or 11 animals were used per group, and all the three groups were randomized such that the distribution of starting tumor sizes were very similar. Mean tumor volumes for the three groups before therapy (day −2) were 0.312±0.181, 0.308±0.203, and 0.303±0.212.

In this experiment, interim data to day 49 are depicted in FIG. 9 below. The top panel in FIG. 9 shows tumor volumes (cm$^3$) for individual animals in each group, and the bottom panel indicates mean tumor volumes in two formats. There were three deaths in the untreated group. Tumor growth control is significantly better for the residualizing label group compared to the conventional label and the untreated groups, as determined by the student-t test on the area under the curves (AUC) for mean tumor volumes (MTV) up to day-49. On day 49, significance (p values) for differences in AUCs of MTVs due to therapy with $^{131}$I-IMP-R4-hRS7, with the respective p values for tumor volume differences before therapy (day −2) given in parentheses, are as follows. Versus untreated: 0.05 (0.78); versus $^{131}$I-hRS7 (CT): 0.03 (0.98); for −hRS7 (CT) versus untreated: 0.14 (0.81). There is continuing divergence in mean tumor volumes between the conventional and the residualizing radioiodine groups on day 49, with the latter group leading to continued decrease. At 8-weeks post-therapy, complete remissions were observed in 5 of 11 mice treated with $^{131}$I-IMP-R4-hRS7, and the MTV was 20% of the starting value. MTV in the untreated and $^{131}$I-hRS7-treated mice at 8 weeks were 280% and 163% of the respective starting values, respectively, with 1 complete remission of 11 mice in the $^{131}$I-hRS7 group.

Figure 10B:
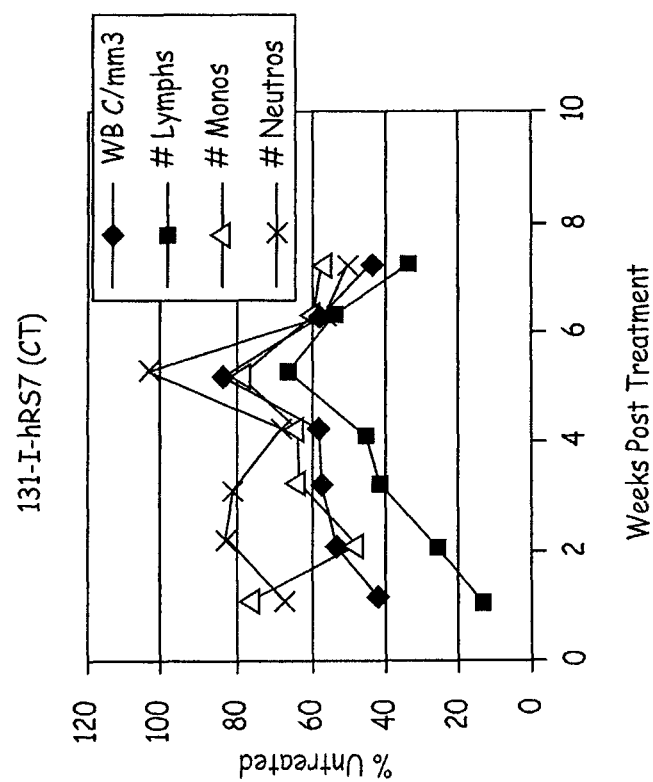
FIGS. 10A and 10B depict determinations of myelotoxicities of treatments with radioiodinated hRS7 in MDA-MB-468 human tumor xenograft-bearing Swiss nude mice (female).
Figure 10A:
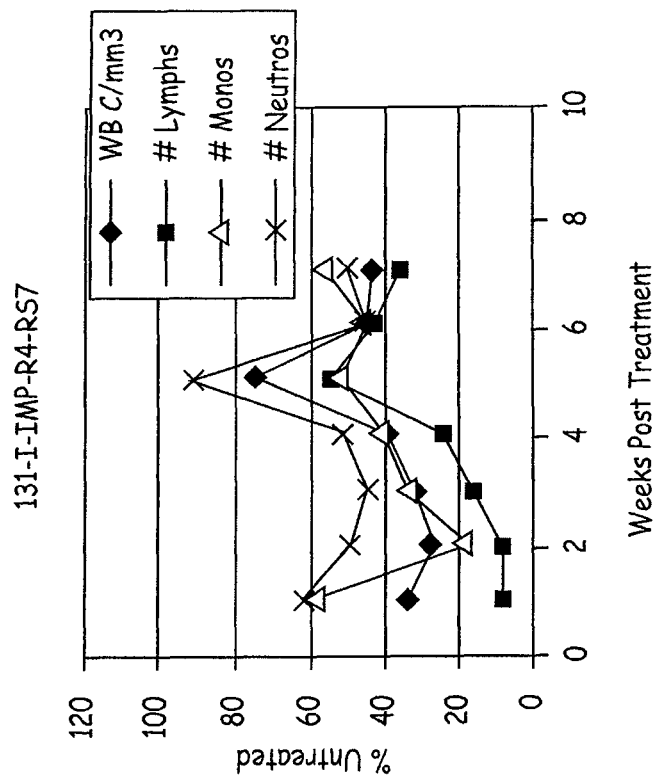

The treatments were well tolerated. The mean body weights of IMP-R4 group on day −2 was 21.93±2.03 and that on day 49 was 23.68±1.81; for 'CT' group, the mean body weights were 21.77±2.21 and 23.90±2.64 on days −2 and 49, respectively. Myelotoxicities of the treated groups, as determined by blood cell counts, are shown in FIG. 10. Briefly: With $^{131}$I-IMP-R4-hRS7, nadirs of 34%, 7% and 61% of the control levels for WBC, lymphocyte and neutrophil counts, respectively, were reached one week after the administration of the agent. By week-5, these recovered to 74%, 58% and 92% of the control levels, respectively, and remained at 45%, 36% and 51% of the control levels on day-49; and for $^{131}$I-hRS7 (CT): nadirs of 41%, 13% and 67% of the control levels for WBC, lymphocyte and neutrophil counts, respectively, were reached one week after the administration of the agent. By week-5, these recovered to 85%, 67% and 103% of the control levels, respectively, and remained at 42%, 32% and 49% of the control levels on day-49.

Figure 11:
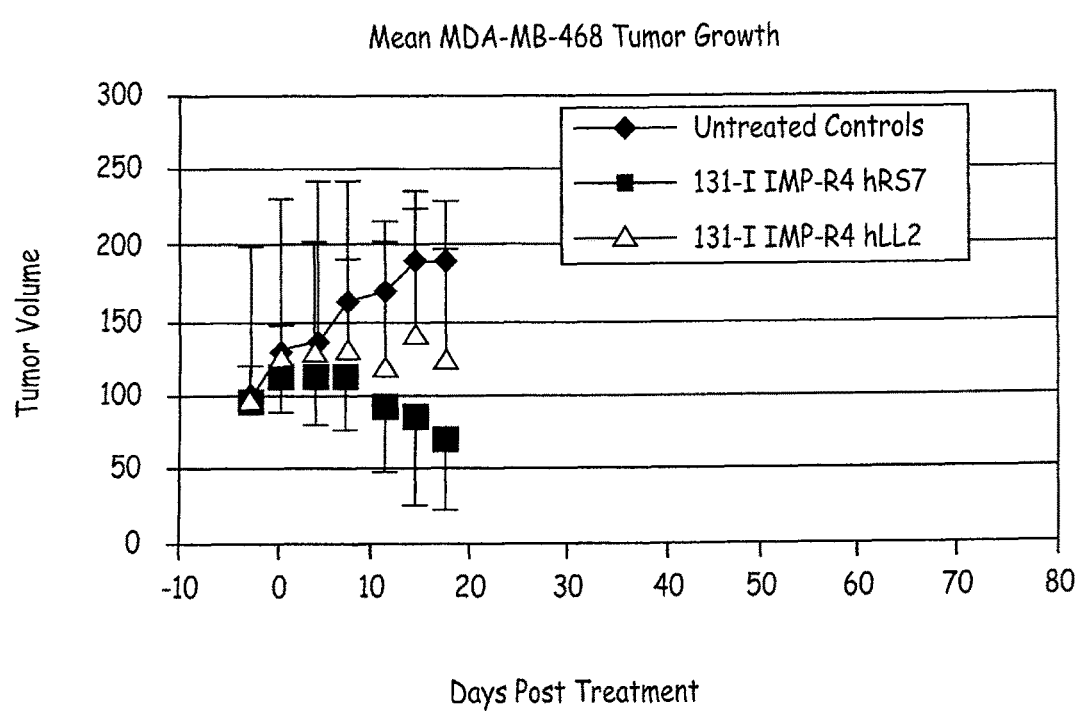
FIG. 11 is a graph demonstrating relative mean tumor volumes (MTV).

Therapy Study-2
Specificity of RAIT using $^{131}$I-IMP-R4-hRS7 in the MDA-MB-468 Tumor Model The efficacy of $^{131}$I-IMP-R4-hRS7 was compared with that of non-specific control humanized antibody, hLL2 (anti-CD-22 MAb), labeled with $^{131}$I-IMP-R4. In this experiment, 175 µCi of each agent was administered. This represents ~70% of the maximum-tolerated dose of $^{131}$I-IMP-R4-hRS7. In this experiment, which included untreated controls, 7-to-8 animals were used per group, and the groups were randomized with regard to the starting tumor volume distributions as in therapy experiment-1. FIG. 11, showing the relative mean tumor volumes (MTV) for the three groups (MTV before therapy: 100), is indicative of the growth control specificity.

Example 5. Treatment of a Breast Cancer Patient with Y-90 Humanized RS7 mAb and with Naked Humanized RS7 mAb A 56-year-old women with a history of recurrent adenocarcinoma of the breast presents with cervical lymph node and left lung metastases. She relapses twice after chemotherapy and hormonal therapies. She is then given two therapeutic injections, two weeks apart, of Y-90-conjugated humanized RS7 mAb i.v., at a dose each of 20 mCi Y-90 in a protein dose of antibody of 100 mg. Four weeks after therapy, her white blood cell and platelet counts have decreased by approximately 50%, but recuperate by 9 weeks post-therapy. At the restaging 12 weeks post-therapy, a ca. 30% decrease in pulmonary and nodal metastases has been measured by computed tomography. Thereafter, she receives 4 weekly infusions, over 3 hours each, of naked humanized RS7, which is tolerated well, except for some transient rigors and chills, and without any adverse effects on her blood counts or blood chemistries. The naked antibody dose for each infusion was 400 mg/m$^2$. Approximately 8 weeks later, restaging by computed tomography indicates an additional decrease in measurable lesions by about 20 percent. At the followup examination 3 months later, her disease appears to be stable (i.e., no evidence of additional, or progressive growth).

What is claimed is:

1. A method of delivering a chemotherapeutic drug to a Trop-2 positive human cancer cell comprising exposing a Trop-2 positive human cancer cell to an immunoconjugate comprising: (i) a humanized anti-Trop-2 antibody or antigen-binding fragment thereof comprising the light chain complementarity determining region (CDR) sequences CDR1 (KASQDVSIAVA, SEQ ID NO:28); CDR2 (SASYRYT, SEQ ID NO:29); and CDR3 (QQHYITPLT, SEQ ID NO:30) and the heavy chain CDR sequences CDR1 (NYGMN, SEQ ID NO:31); CDR2 (WINTYTGEPTYTDDFKG, SEQ ID NO:32) and CDR3 (GGFGSSYWYFDV, SEQ ID NO:33); and (ii) a chemotherapeutic drug conjugated to the anti-Trop-2 antibody or fragment thereof, wherein the drug is a camptothecin or an antimitotic agent.

2. The method of claim 1, wherein the anti-Trop-2 antibody or fragment thereof comprises human IgG1 constant region sequences.

3. The method of claim 1, wherein the human cancer cell is a human lung, breast, bladder, ovary, uterus, stomach or prostate cancer cell.

4. The method of claim 1, wherein the antimitotic agent is a vinca alkaloid, a taxane or paclitaxel.

5. The method of claim 1, wherein the antimitotic agent is a microtubule inhibitor.

* * * * *

UNITED STATES PATENT AND TRADEMARK OFFICE
CERTIFICATE OF CORRECTION

PATENT NO. : 9,745,380 B2
APPLICATION NO. : 11/868290
DATED : August 29, 2017
INVENTOR(S) : Serengulam Govindan et al.

It is certified that error appears in the above-identified patent and that said Letters Patent is hereby corrected as shown below:

In the Specification

In Column 1, below the paragraph ending at Line 10 and above the heading FIELD OF INVENTION, please insert the following heading and text:

--GOVERNMENT SUPPORT
This invention was made with government support under Grant Number CA072324 awarded by the National Institutes of Health. The government has certain rights in the invention.--

Signed and Sealed this
Third Day of April, 2018

Andrei Iancu
*Director of the United States Patent and Trademark Office*

SEQUENCE LISTING

```
<160> NUMBER OF SEQ ID NOS: 33

<210> SEQ ID NO 1
<211> LENGTH: 324
<212> TYPE: DNA
<213> ORGANISM: Mus sp.
<220> FEATURE:
<221> NAME/KEY: CDS
<222> LOCATION: (1)..(324)

<400> SEQUENCE: 1 gac att cag ctg acc cag tct cac aaa ttc atg tcc aca tca gta gga      48
Asp Ile Gln Leu Thr Gln Ser His Lys Phe Met Ser Thr Ser Val Gly
1               5                   10                  15 gac agg gtc agc atc acc tgc aag gcc agt cag gat gtg agt att gct      96
Asp Arg Val Ser Ile Thr Cys Lys Ala Ser Gln Asp Val Ser Ile Ala
            20                  25                  30 gta gcc tgg tat caa cag aaa cca gga caa tct cct aaa cta ctg att     144
Val Ala Trp Tyr Gln Gln Lys Pro Gly Gln Ser Pro Lys Leu Leu Ile
        35                  40                  45 tac tcg gca tcc tac cgg tac act gga gtc cct gat cgc ttc act ggc     192
Tyr Ser Ala Ser Tyr Arg Tyr Thr Gly Val Pro Asp Arg Phe Thr Gly
    50                  55                  60 agt gga tct ggg acg gat ttc act ttc acc atc agc agt gtg cag gct     240
Ser Gly Ser Gly Thr Asp Phe Thr Phe Thr Ile Ser Ser Val Gln Ala
65                  70                  75                  80 gaa gac ctg gca gtt tat tac tgt cag caa cat tat att act ccg ctc     288
```

```
Glu Asp Leu Ala Val Tyr Tyr Cys Gln Gln His Tyr Ile Thr Pro Leu
                85                  90                  95 acg ttc ggt gct ggg acc aag ctg gag ctg aaa cgg                        324
Thr Phe Gly Ala Gly Thr Lys Leu Glu Leu Lys Arg
            100                 105

<210> SEQ ID NO 2
<211> LENGTH: 108
<212> TYPE: PRT
<213> ORGANISM: Mus sp.

<400> SEQUENCE: 2

Asp Ile Gln Leu Thr Gln Ser His Lys Phe Met Ser Thr Ser Val Gly
1               5                   10                  15

Asp Arg Val Ser Ile Thr Cys Lys Ala Ser Gln Asp Val Ser Ile Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ile Thr Pro Leu
                85                  90                  95

Thr Phe Gly Ala Gly Thr Lys Leu Glu Leu Lys Arg
            100                 105

<210> SEQ ID NO 3
<211> LENGTH: 360
<212> TYPE: DNA
<213> ORGANISM: Mus sp.
<220> FEATURE:
<221> NAME/KEY: CDS
<222> LOCATION: (1)..(360)

<400> SEQUENCE: 3 gtg aag ctg cag gag tca gga cct gag ctg aag aag cct gga gag aca        48
Val Lys Leu Gln Glu Ser Gly Pro Glu Leu Lys Lys Pro Gly Glu Thr
1               5                   10                  15 gtc aag atc tcc tgc aag gct tct gga tat acc ttc aca aac tat gga        96
Val Lys Ile Ser Cys Lys Ala Ser Gly Tyr Thr Phe Thr Asn Tyr Gly
            20                  25                  30 atg aac tgg gtg aag cag gct cca gga aag ggt tta aag tgg atg ggc       144
Met Asn Trp Val Lys Gln Ala Pro Gly Lys Gly Leu Lys Trp Met Gly
        35                  40                  45 tgg ata aac acc tac act gga gag cca aca tat act gat gac ttc aag       192
Trp Ile Asn Thr Tyr Thr Gly Glu Pro Thr Tyr Thr Asp Asp Phe Lys
    50                  55                  60 gga cgg ttt gcc ttc tct ttg gaa acc tct gcc acc act gcc tat ttg       240
Gly Arg Phe Ala Phe Ser Leu Glu Thr Ser Ala Thr Thr Ala Tyr Leu
65                  70                  75                  80 cag atc aac aac ctc aaa agt gag gac atg gct aca tat ttc tgt gca       288
Gln Ile Asn Asn Leu Lys Ser Glu Asp Met Ala Thr Tyr Phe Cys Ala
                85                  90                  95 aga ggg ggg ttc ggt agt agc tac tgg tac ttc gat gtc tgg ggc caa       336
Arg Gly Gly Phe Gly Ser Ser Tyr Trp Tyr Phe Asp Val Trp Gly Gln
            100                 105                 110 ggg acc acg gtc acc gtc tcc tca                                        360
Gly Thr Thr Val Thr Val Ser Ser
        115                 120
```

```
<210> SEQ ID NO 4
<211> LENGTH: 120
<212> TYPE: PRT
<213> ORGANISM: Mus sp.

<400> SEQUENCE: 4

Val Lys Leu Gln Glu Ser Gly Pro Glu Leu Lys Lys Pro Gly Glu Thr
1               5                   10                  15

Val Lys Ile Ser Cys Lys Ala Ser Gly Tyr Thr Phe Thr Asn Tyr Gly
            20                  25                  30

Met Asn Trp Val Lys Gln Ala Pro Gly Lys Gly Leu Lys Trp Met Gly
        35                  40                  45

Trp Ile Asn Thr Tyr Thr Gly Glu Pro Thr Tyr Thr Asp Asp Phe Lys
    50                  55                  60

Gly Arg Phe Ala Phe Ser Leu Glu Thr Ser Ala Thr Thr Ala Tyr Leu
65                  70                  75                  80

Gln Ile Asn Asn Leu Lys Ser Glu Asp Met Ala Thr Tyr Phe Cys Ala
                85                  90                  95

Arg Gly Gly Phe Gly Ser Ser Tyr Trp Tyr Phe Asp Val Trp Gly Gln
            100                 105                 110

Gly Thr Thr Val Thr Val Ser Ser
            115                 120

<210> SEQ ID NO 5
<211> LENGTH: 106
<212> TYPE: PRT
<213> ORGANISM: Homo sapiens

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile
            100                 105

<210> SEQ ID NO 6
<211> LENGTH: 11
<212> TYPE: PRT
<213> ORGANISM: Homo sapiens

<400> SEQUENCE: 6

Trp Gly Gln Gly Ser Leu Val Thr Val Ser Ser
1               5                   10

<210> SEQ ID NO 7
<211> LENGTH: 108
<212> TYPE: PRT
<213> ORGANISM: Homo sapiens

<400> SEQUENCE: 7
```

Asp Ile Gln Leu Thr Gln Ser Pro Ser Ser Leu Ser Ala Ser Val Gly
1               5                   10                  15

Asp Arg Val Ser Ile Thr Cys Lys Ala Ser Gln Asp Val Ser Ile Ala
            20                  25                  30

Val Ala Trp Tyr Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Val Tyr Tyr Cys Gln Gln His Tyr Ile Thr Pro Leu
                85                  90                  95

Thr Phe Gly Ala Gly Thr Lys Val Glu Ile Lys Arg
            100                 105

<210> SEQ ID NO 8
<211> LENGTH: 108
<212> TYPE: PRT
<213> ORGANISM: Homo sapiens

<400> SEQUENCE: 8

Val Gln Leu Val Gln Ser Gly Ser Glu Leu Lys Lys Pro Gly Ala Ser
1               5                   10                  15

Val Lys Val Ser Cys Lys Ala Ser Gly Tyr Thr Phe Thr Ser Tyr Ala
            20                  25                  30

Met Asn Trp Val Arg Gln Ala Pro Gly Gln Gly Leu Glu Trp Met Gly
        35                  40                  45

Trp Ile Asn Thr Asn Thr Gly Asn Pro Thr Tyr Ala Gln Gly Phe Thr
    50                  55                  60

Gly Arg Phe Val Phe Ser Leu Asp Thr Ser Val Ser Thr Ala Tyr Leu
65              70                  75                  80

Gln Ile Ser Ser Leu Lys Ala Asp Asp Thr Ala Val Tyr Tyr Cys Ala
                85                  90                  95

Arg Glu Asp Ser Asn Gly Tyr Lys Ile Phe Asp Tyr
            100                 105

<210> SEQ ID NO 9
<211> LENGTH: 11
<212> TYPE: PRT
<213> ORGANISM: Mus sp.

<400> SEQUENCE: 9

Trp Gly Gln Gly Thr Thr Val Thr Val Ser Ser
1               5                   10

<210> SEQ ID NO 10
<211> LENGTH: 109
<212> TYPE: PRT
<213> ORGANISM: Homo sapiens

<400> SEQUENCE: 10

Gln Val Gln Leu Gln Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

```
Gly Trp Ile Asn Thr Tyr Thr Gly Glu Pro Thr Tyr Thr Asp Asp Phe
            50                  55                  60

Lys Gly Arg Phe Ala Phe Ser Leu Asp Thr Ser Val Ser Thr Ala Tyr
 65                  70                  75                  80

Leu Gln Ile Ser Ser Leu Lys Ala Asp Asp Thr Ala Val Tyr Phe Cys
                 85                  90                  95

Ala Arg Gly Gly Phe Gly Ser Ser Tyr Trp Tyr Phe Val
            100                 105

<210> SEQ ID NO 11
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 11 gac atc cag ctg acc cag tct cca tcc tcc ctg tct gca tct gta gga    48
Asp Ile Gln Leu Thr Gln Ser Pro Ser Ser Leu Ser Ala Ser Val Gly
 1               5                  10                  15 gac aga gtc agc atc acc tgc aag gcc agt cag gat gtg agt att gct    96
Asp Arg Val Ser Ile Thr Cys Lys Ala Ser Gln Asp Val Ser Ile Ala
             20                  25                  30 gta gcc tgg tat cag cag aaa cca ggg aaa gcc cct aag ctc ctg atc   144
Val Ala Trp Tyr Gln Gln Lys Pro Gly Lys Ala Pro Lys Leu Leu Ile
         35                  40                  45 tac tcg gca tcc tac cgg tac act gga gtc cct gat agg ttc agt ggc   192
Tyr Ser Ala Ser Tyr Arg Tyr Thr Gly Val Pro Asp Arg Phe Ser Gly
     50                  55                  60 agt gga tct ggg aca gat ttc act ctc acc atc agc agt ctg caa cct   240
Ser Gly Ser Gly Thr Asp Phe Thr Leu Thr Ile Ser Ser Leu Gln Pro
 65                  70                  75                  80 gaa gat ttt gca gtt tat tac tgt cag caa cat tat att act ccg ctc   288
Glu Asp Phe Ala Val Tyr Tyr Cys Gln Gln His Tyr Ile Thr Pro Leu
                 85                  90                  95 acg ttc ggt gct ggg acc aag gtg gag atc aaa cgt                   324
Thr Phe Gly Ala Gly Thr Lys Val Glu Ile Lys Arg
            100                 105

<210> SEQ ID NO 12
<211> LENGTH: 108
<212> TYPE: PRT
<213> ORGANISM: Homo sapiens

<400> SEQUENCE: 12

Asp Ile Gln Leu Thr Gln Ser Pro Ser Ser Leu Ser Ala Ser Val Gly
 1               5                  10                  15

Asp Arg Val Ser Ile Thr Cys Lys Ala Ser Gln Asp Val Ser Ile Ala
             20                  25                  30

Val Ala Trp Tyr Gln Gln Lys Pro Gly Lys Ala Pro Lys Leu Leu Ile
         35                  40                  45

Tyr Ser Ala Ser Tyr Arg Tyr Thr Gly Val Pro Asp Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Val Tyr Tyr Cys Gln Gln His Tyr Ile Thr Pro Leu
                 85                  90                  95

Thr Phe Gly Ala Gly Thr Lys Val Glu Ile Lys Arg
            100                 105
```

```
<210> SEQ ID NO 13
<211> LENGTH: 363
<212> TYPE: DNA
<213> ORGANISM: Homo sapiens
<220> FEATURE:
<221> NAME/KEY: CDS
<222> LOCATION: (1)..(363)

<400> SEQUENCE: 13 cag gtc caa ctg cag caa tct ggg tct gag ttg aag aag cct ggg gcc      48
Gln Val Gln Leu Gln Gln Ser Gly Ser Glu Leu Lys Lys Pro Gly Ala
1               5                   10                  15 tca gtg aag gtt tcc tgc aag gct tct gga tac acc ttc aca aac tat      96
Ser Val Lys Val Ser Cys Lys Ala Ser Gly Tyr Thr Phe Thr Asn Tyr
            20                  25                  30 gga atg aac tgg gtg aag cag gcc cct gga caa ggg ctt aaa tgg atg     144
Gly Met Asn Trp Val Lys Gln Ala Pro Gly Gln Gly Leu Lys Trp Met
        35                  40                  45 ggc tgg ata aac acc tac act gga gag cca aca tat act gat gac ttc     192
Gly Trp Ile Asn Thr Tyr Thr Gly Glu Pro Thr Tyr Thr Asp Asp Phe
    50                  55                  60 aag gga cgg ttt gcc ttc tcc ttg gac acc tct gtc agc acg gca tat     240
Lys Gly Arg Phe Ala Phe Ser Leu Asp Thr Ser Val Ser Thr Ala Tyr
65                  70                  75                  80 ctc cag atc agc agc cta aag gct gac gac act gcc gtg tat ttc tgt     288
Leu Gln Ile Ser Ser Leu Lys Ala Asp Asp Thr Ala Val Tyr Phe Cys
                85                  90                  95 gca aga ggg ggg ttc ggt agt agc tac tgg tac ttc gat gtc tgg ggc     336
Ala Arg Gly Gly Phe Gly Ser Ser Tyr Trp Tyr Phe Asp Val Trp Gly
            100                 105                 110 caa ggg tcc ctg gtc acc gtc tcc tca                                 363
Gln Gly Ser Leu Val Thr Val Ser Ser
        115                 120

<210> SEQ ID NO 14
<211> LENGTH: 121
<212> TYPE: PRT
<213> ORGANISM: Homo sapiens

<400> SEQUENCE: 14

Gln Val Gln Leu Gln Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Thr Asp Asp Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Asp Asp Thr Ala Val Tyr Phe Cys
                85                  90                  95

Ala Arg Gly Gly Phe Gly Ser Ser Tyr Trp Tyr Phe Asp Val Trp Gly
            100                 105                 110

Gln Gly Ser Leu Val Thr Val Ser Ser
        115                 120

<210> SEQ ID NO 15
<211> LENGTH: 702
```

```
<212> TYPE: DNA
<213> ORGANISM: Homo sapiens
<220> FEATURE:
<221> NAME/KEY: CDS
<222> LOCATION: (1)..(702)

<400> SEQUENCE: 15 atg gga tgg agc tgt atc atc ctc ttc ttg gta gca aca gct aca ggt      48
Met Gly Trp Ser Cys Ile Ile Leu Phe Leu Val Ala Thr Ala Thr Gly
1               5                   10                  15 gtc cac tcc gac atc cag ctg acc cag tct cca tcc tcc ctg tct gca      96
Val His Ser Asp Ile Gln Leu Thr Gln Ser Pro Ser Ser Leu Ser Ala
            20                  25                  30 tct gta gga gac aga gtc agc atc acc tgc aag gcc agt cag gat gtg     144
Ser Val Gly Asp Arg Val Ser Ile Thr Cys Lys Ala Ser Gln Asp Val
        35                  40                  45 agt att gct gta gcc tgg tat cag cag aaa cca ggg aaa gcc cct aag     192
Ser Ile Ala Val Ala Trp Tyr Gln Gln Lys Pro Gly Lys Ala Pro Lys
    50                  55                  60 ctc ctg atc tac tcg gca tcc tac cgg tac act gga gtc cct gat agg     240
Leu Leu Ile Tyr Ser Ala Ser Tyr Arg Tyr Thr Gly Val Pro Asp Arg
65                  70                  75                  80 ttc agt ggc agt gga tct ggg aca gat ttc act ctc acc atc agc agt     288
Phe Ser Gly Ser Gly Ser Gly Thr Asp Phe Thr Leu Thr Ile Ser Ser
                85                  90                  95 ctg caa cct gaa gat ttt gca gtt tat tac tgt cag caa cat tat att     336
Leu Gln Pro Glu Asp Phe Ala Val Tyr Tyr Cys Gln Gln His Tyr Ile
            100                 105                 110 act ccg ctc acg ttc ggt gct ggg acc aag gtg gag atc aaa cgt act     384
Thr Pro Leu Thr Phe Gly Ala Gly Thr Lys Val Glu Ile Lys Arg Thr
        115                 120                 125 gtg gct gca cca tct gtc ttc atc ttc ccg cca tct gat gag cag ttg     432
Val Ala Ala Pro Ser Val Phe Ile Phe Pro Pro Ser Asp Glu Gln Leu
    130                 135                 140 aaa tct gga act gcc tct gtt gtg tgc ctg ctg aat aac ttc tat ccc     480
Lys Ser Gly Thr Ala Ser Val Val Cys Leu Leu Asn Asn Phe Tyr Pro
145                 150                 155                 160 aga gag gcc aaa gta cag tgg aag gtg gat aac gcc ctc caa tcg ggt     528
Arg Glu Ala Lys Val Gln Trp Lys Val Asp Asn Ala Leu Gln Ser Gly
                165                 170                 175 aac tcc cag gag agt gtc aca gag cag gac agc aag gac agc acc tac     576
Asn Ser Gln Glu Ser Val Thr Glu Gln Asp Ser Lys Asp Ser Thr Tyr
            180                 185                 190 agc ctc agc agc acc ctg acg ctg agc aaa gca gac tac gag aaa cac     624
Ser Leu Ser Ser Thr Leu Thr Leu Ser Lys Ala Asp Tyr Glu Lys His
        195                 200                 205 aaa gtc tac gcc tgc gaa gtc acc cat cag ggc ctg agc tcg ccc gtc     672
Lys Val Tyr Ala Cys Glu Val Thr His Gln Gly Leu Ser Ser Pro Val
    210                 215                 220 aca aag agc ttc aac agg gga gag tgt tag                             702
Thr Lys Ser Phe Asn Arg Gly Glu Cys
225                 230

<210> SEQ ID NO 16
<211> LENGTH: 233
<212> TYPE: PRT
<213> ORGANISM: Homo sapiens

<400> SEQUENCE: 16

Met Gly Trp Ser Cys Ile Ile Leu Phe Leu Val Ala Thr Ala Thr Gly
1               5                   10                  15
```

```
Val His Ser Asp Ile Gln Leu Thr Gln Ser Pro Ser Ser Leu Ser Ala
         20                  25                  30

Ser Val Gly Asp Arg Val Ser Ile Thr Cys Lys Ala Ser Gln Asp Val
     35                  40                  45

Ser Ile Ala Val Ala Trp Tyr Gln Gln Lys Pro Gly Lys Ala Pro Lys
 50                  55                  60

Leu Leu Ile Tyr Ser Ala Ser Tyr Arg Tyr Thr Gly Val Pro Asp Arg
65                  70                  75                  80

Phe Ser Gly Ser Gly Ser Gly Thr Asp Phe Thr Leu Thr Ile Ser Ser
                 85                  90                  95

Leu Gln Pro Glu Asp Phe Ala Val Tyr Tyr Cys Gln Gln His Tyr Ile
            100                 105                 110

Thr Pro Leu Thr Phe Gly Ala Gly Thr Lys Val Glu Ile Lys Arg Thr
        115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
210                 215                 220

Thr Lys Ser Phe Asn Arg Gly Glu Cys
225                 230

<210> SEQ ID NO 17
<211> LENGTH: 1410
<212> TYPE: DNA
<213> ORGANISM: Homo sapiens
<220> FEATURE:
<221> NAME/KEY: CDS
<222> LOCATION: (1)..(1410)

<400> SEQUENCE: 17 atg gga tgg agc tgt atc atc ctc ttc ttg gta gca aca gct aca ggt      48
Met Gly Trp Ser Cys Ile Ile Leu Phe Leu Val Ala Thr Ala Thr Gly
1               5                   10                  15 gtc cac tcc gtc caa ctg cag caa tct ggg tct gag ttg aag aag cct      96
Val His Ser Val Gln Leu Gln Gln Ser Gly Ser Glu Leu Lys Lys Pro
            20                  25                  30 ggg gcc tca gtg aag gtt tcc tgc aag gct tct gga tac acc ttc aca     144
Gly Ala Ser Val Lys Val Ser Cys Lys Ala Ser Gly Tyr Thr Phe Thr
        35                  40                  45 aac tat gga atg aac tgg gtg aag cag gcc cct gga caa ggg ctt aaa     192
Asn Tyr Gly Met Asn Trp Val Lys Gln Ala Pro Gly Gln Gly Leu Lys
 50                  55                  60 tgg atg ggc tgg ata aac acc tac act gga gag cca aca tat act gat     240
Trp Met Gly Trp Ile Asn Thr Tyr Thr Gly Glu Pro Thr Tyr Thr Asp
65                  70                  75                  80 gac ttc aag gga cgg ttt gcc ttc tcc ttg gac acc tct gtc agc acg     288
Asp Phe Lys Gly Arg Phe Ala Phe Ser Leu Asp Thr Ser Val Ser Thr
                 85                  90                  95 gca tat ctc cag atc agc agc cta aag gct gac gac act gcc gtg tat     336
Ala Tyr Leu Gln Ile Ser Ser Leu Lys Ala Asp Asp Thr Ala Val Tyr
```

-continued

```
                100                 105                 110
ttc tgt gca aga ggg ggg ttc ggt agt agc tac tgg tac ttc gat gtc        384
Phe Cys Ala Arg Gly Gly Phe Gly Ser Ser Tyr Trp Tyr Phe Asp Val
            115                 120                 125 tgg ggc caa ggg tcc ctg gtc acc gtc tcc tca gcc tcc acc aag ggc        432
Trp Gly Gln Gly Ser Leu Val Thr Val Ser Ser Ala Ser Thr Lys Gly
        130                 135                 140 cca tcg gtc ttc ccc ctg gca ccc tcc tcc aag agc acc tct ggg ggc        480
Pro Ser Val Phe Pro Leu Ala Pro Ser Ser Lys Ser Thr Ser Gly Gly
145                 150                 155                 160 aca gcg gcc ctg ggc tgc ctg gtc aag gac tac ttc ccc gaa ccg gtg        528
Thr Ala Ala Leu Gly Cys Leu Val Lys Asp Tyr Phe Pro Glu Pro Val
                165                 170                 175 acg gtg tcg tgg aac tca ggc gcc ctg acc agc ggc gtg cac acc ttc        576
Thr Val Ser Trp Asn Ser Gly Ala Leu Thr Ser Gly Val His Thr Phe
            180                 185                 190 ccg gct gtc cta cag tcc tca gga ctc tac tcc ctc agc agc gtg gtg        624
Pro Ala Val Leu Gln Ser Ser Gly Leu Tyr Ser Leu Ser Ser Val Val
        195                 200                 205 acc gtg ccc tcc agc agc ttg ggc acc cag acc tac atc tgc aac gtg        672
Thr Val Pro Ser Ser Ser Leu Gly Thr Gln Thr Tyr Ile Cys Asn Val
    210                 215                 220 aat cac aag ccc agc aac acc aag gtg gac aag aga gtt gag ccc aaa        720
Asn His Lys Pro Ser Asn Thr Lys Val Asp Lys Arg Val Glu Pro Lys
225                 230                 235                 240 tct tgt gac aaa act cac aca tgc cca ccg tgc cca gca cct gaa ctc        768
Ser Cys Asp Lys Thr His Thr Cys Pro Pro Cys Pro Ala Pro Glu Leu
                245                 250                 255 ctg ggg gga ccg tca gtc ttc ctc ttc ccc cca aaa ccc aag gac acc        816
Leu Gly Gly Pro Ser Val Phe Leu Phe Pro Pro Lys Pro Lys Asp Thr
            260                 265                 270 ctc atg atc tcc cgg acc cct gag gtc aca tgc gtg gtg gtg gac gtg        864
Leu Met Ile Ser Arg Thr Pro Glu Val Thr Cys Val Val Val Asp Val
        275                 280                 285 agc cac gaa gac cct gag gtc aag ttc aac tgg tac gtg gac ggc gtg        912
Ser His Glu Asp Pro Glu Val Lys Phe Asn Trp Tyr Val Asp Gly Val
    290                 295                 300 gag gtg cat aat gcc aag aca aag ccg cgg gag gag cag tac aac agc        960
Glu Val His Asn Ala Lys Thr Lys Pro Arg Glu Glu Gln Tyr Asn Ser
305                 310                 315                 320 acg tac cgt gtg gtc agc gtc ctc acc gtc ctg cac cag gac tgg ctg       1008
Thr Tyr Arg Val Val Ser Val Leu Thr Val Leu His Gln Asp Trp Leu
                325                 330                 335 aat ggc aag gag tac aag tgc aag gtc tcc aac aaa gcc ctc cca gcc       1056
Asn Gly Lys Glu Tyr Lys Cys Lys Val Ser Asn Lys Ala Leu Pro Ala
            340                 345                 350 ccc atc gag aaa acc atc tcc aaa gcc aaa ggg cag ccc cga gaa cca       1104
Pro Ile Glu Lys Thr Ile Ser Lys Ala Lys Gly Gln Pro Arg Glu Pro
        355                 360                 365 cag gtg tac acc ctg ccc cca tcc cgg gag gag atg acc aag aac cag       1152
Gln Val Tyr Thr Leu Pro Pro Ser Arg Glu Glu Met Thr Lys Asn Gln
    370                 375                 380 gtc agc ctg acc tgc ctg gtc aaa ggc ttc tat ccc agc gac atc gcc       1200
Val Ser Leu Thr Cys Leu Val Lys Gly Phe Tyr Pro Ser Asp Ile Ala
385                 390                 395                 400 gtg gag tgg gag agc aat ggg cag ccg gag aac aac tac aag acc acg       1248
Val Glu Trp Glu Ser Asn Gly Gln Pro Glu Asn Asn Tyr Lys Thr Thr
                405                 410                 415 cct ccc gtg ctg gac tcc gac ggc tcc ttc ttc ctc tat agc aag ctc       1296
```

```
            Pro Pro Val Leu Asp Ser Asp Gly Ser Phe Phe Leu Tyr Ser Lys Leu
                        420                 425                 430 acc gtg gac aag agc agg tgg cag cag ggg aac gtc ttc tca tgc tcc        1344
Thr Val Asp Lys Ser Arg Trp Gln Gln Gly Asn Val Phe Ser Cys Ser
            435                 440                 445 gtg atg cat gag gct ctg cac aac cac tac acg cag aag agc ctc tcc        1392
Val Met His Glu Ala Leu His Asn His Tyr Thr Gln Lys Ser Leu Ser
450                 455                 460 ctg tct ccg ggt aaa tga                                                1410
Leu Ser Pro Gly Lys
465

<210> SEQ ID NO 18
<211> LENGTH: 469
<212> TYPE: PRT
<213> ORGANISM: Homo sapiens

<400> SEQUENCE: 18

Met Gly Trp Ser Cys Ile Ile Leu Phe Leu Val Ala Thr Ala Thr Gly
1               5                   10                  15

Val His Ser Val Gln Leu Gln Gln Ser Gly Ser Glu Leu Lys Lys Pro
            20                  25                  30

Gly Ala Ser Val Lys Val Ser Cys Lys Ala Ser Gly Tyr Thr Phe Thr
        35                  40                  45

Asn Tyr Gly Met Asn Trp Val Lys Gln Ala Pro Gly Gln Gly Leu Lys
    50                  55                  60

Trp Met Gly Trp Ile Asn Thr Tyr Thr Gly Glu Pro Thr Tyr Thr Asp
65                  70                  75                  80

Asp Phe Lys Gly Arg Phe Ala Phe Ser Leu Asp Thr Ser Val Ser Thr
                85                  90                  95

Ala Tyr Leu Gln Ile Ser Ser Leu Lys Ala Asp Asp Thr Ala Val Tyr
            100                 105                 110

Phe Cys Ala Arg Gly Gly Phe Gly Ser Ser Tyr Trp Tyr Phe Asp Val
        115                 120                 125

Trp Gly Gln Gly Ser Leu Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300
```

Glu Val His Asn Ala Lys Thr Lys Pro Arg Glu Gln Tyr Asn Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
        340                 345                 350

Pro Ile Glu Lys Thr Ile Ser Lys Ala Lys Gly Gln Pro Arg Glu Pro
    355                 360                 365

Gln Val Tyr Thr Leu Pro Pro Ser Arg Glu Glu Met Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
        420                 425                 430

Thr Val Asp Lys Ser Arg Trp Gln Gln Gly Asn Val Phe Ser Cys Ser
    435                 440                 445

Val Met His Glu Ala Leu His Asn His Tyr Thr Gln Lys Ser Leu Ser
450                 455                 460

Leu Ser Pro Gly Lys
465

<210> SEQ ID NO 19
<211> LENGTH: 176
<212> TYPE: DNA
<213> ORGANISM: Artificial
<220> FEATURE:
<223> OTHER INFORMATION: Description of Artificial Sequence: Synthetic
      oligonucleotide

<400> SEQUENCE: 19
ggtctgagtt gaagaagcct ggggcctcag tgaaggtttc ctgcaaggct tctggataca      60
ccttcacaaa ctatggaatg aactgggtga agcaggcccc tggacaaggg cttaaatgga     120
tgggctggat aaacacctac actggagagc caacatatac tgatgacttc aaggga         176

<210> SEQ ID NO 20
<211> LENGTH: 168
<212> TYPE: DNA
<213> ORGANISM: Artificial
<220> FEATURE:
<223> OTHER INFORMATION: Description of Artificial Sequence: Synthetic
      Oligonucelotide

<400> SEQUENCE: 20
acccttggcc ccagacatcg aagtaccagt agctactacc gaaccccct cttgcacaga       60 aatacacggc agtgtcgtca gcctttaggc tgctgatctg agatatgcc gtgctgacag      120 aggtgtccaa ggagaaggca aaccgtccct tgaagtcatc agtatatg                  168

<210> SEQ ID NO 21
<211> LENGTH: 38
<212> TYPE: DNA
<213> ORGANISM: Artificial
<220> FEATURE:
<223> OTHER INFORMATION: Description of Artificial Sequence: Synthetic
      oligonucleotide

<400> SEQUENCE: 21
gtggtgctgc agcaatctgg gtctgagttg aagaagcc        38

<210> SEQ ID NO 22
<211> LENGTH: 38
<212> TYPE: DNA
<213> ORGANISM: Artificial
<220> FEATURE:
<223> OTHER INFORMATION: Description of Artificial Sequence: Synthetic
      Oligonucleotide

<400> SEQUENCE: 22
tgaggagacg gtgaccaggg acccttggcc ccagacat       38

<210> SEQ ID NO 23
<211> LENGTH: 156
<212> TYPE: DNA
<213> ORGANISM: Artificial
<220> FEATURE:
<223> OTHER INFORMATION: Description of Artificial Sequence: Synthetic
      oligonucleotide

<400> SEQUENCE: 23
ctccatcctc cctgtctgca tctgtaggag acagagtcag catcacctgc aaggccagtc      60
aggatgtgag tattgctgta gcctggtatc agcagaaacc agggaaagcc cctaagctcc     120
tgatctactc ggcatcctac cggtacactg gagtcc        156

<210> SEQ ID NO 24
<211> LENGTH: 155
<212> TYPE: DNA
<213> ORGANISM: Artificial
<220> FEATURE:
<223> OTHER INFORMATION: Description of Artificial Sequence: Synthetic
      oligonucleotide

<400> SEQUENCE: 24
ccttggtccc agcaccgaac gtgagcggag taatataatg ttgctgacag taataaactg      60
caaaatcttc aggttgcaga ctgctgatgg tgagagtgaa atctgtccca gatccactgc     120
cactgaacct atcagggact ccagtgtacc ggtag         155

<210> SEQ ID NO 25
<211> LENGTH: 37
<212> TYPE: DNA
<213> ORGANISM: Artificial
<220> FEATURE:
<223> OTHER INFORMATION: Description of Artificial Sequence: Synthetic
      oligonucleotide

<400> SEQUENCE: 25
gacattcagc tgacccagtc tccatcctcc ctgtctg        37

<210> SEQ ID NO 26
<211> LENGTH: 31
<212> TYPE: DNA
<213> ORGANISM: Artificial
<220> FEATURE:
<223> OTHER INFORMATION: Description of Artificial Sequence: Synthetic
      oligonucleotide

<400> SEQUENCE: 26
acgttagatc tccaccttgg tcccagcacc g         31

<210> SEQ ID NO 27
<211> LENGTH: 11
<212> TYPE: PRT

-continued

```
<213> ORGANISM: Homo sapiens

<400> SEQUENCE: 27

Trp Gly Gln Gly Ser Leu Val Thr Val Ser Ser
1               5                   10

<210> SEQ ID NO 28
<211> LENGTH: 11
<212> TYPE: PRT
<213> ORGANISM: Mus sp.

<400> SEQUENCE: 28

Lys Ala Ser Gln Asp Val Ser Ile Ala Val Ala
1               5                   10

<210> SEQ ID NO 29
<211> LENGTH: 7
<212> TYPE: PRT
<213> ORGANISM: Mus sp.

<400> SEQUENCE: 29

Ser Ala Ser Tyr Arg Tyr Thr
1               5

<210> SEQ ID NO 30
<211> LENGTH: 9
<212> TYPE: PRT
<213> ORGANISM: Mus sp.

<400> SEQUENCE: 30

Gln Gln His Tyr Ile Thr Pro Leu Thr
1               5

<210> SEQ ID NO 31
<211> LENGTH: 5
<212> TYPE: PRT
<213> ORGANISM: Mus sp.

<400> SEQUENCE: 31

Asn Tyr Gly Met Asn
1               5

<210> SEQ ID NO 32
<211> LENGTH: 17
<212> TYPE: PRT
<213> ORGANISM: Mus sp.

<400> SEQUENCE: 32

Trp Ile Asn Thr Tyr Thr Gly Glu Pro Thr Tyr Thr Asp Asp Phe Lys
1               5                   10                  15

Gly

<210> SEQ ID NO 33
<211> LENGTH: 12
<212> TYPE: PRT
<213> ORGANISM: Mus sp.

<400> SEQUENCE: 33

Gly Gly Phe Gly Ser Ser Tyr Trp Tyr Phe Asp Val
1               5                   10
```